(12) United States Patent
Mizuguchi et al.

(10) Patent No.: US 7,709,240 B2
(45) Date of Patent: May 4, 2010

(54) AMP DEAMINASE ORIGINATING STREPTOMYCES AND UTILIZATION THEREOF

(75) Inventors: Ryoko Mizuguchi, Nagahama (JP); Shigeharu Mori, Nagoya (JP); Atsuki Toumoto, Kakamigahara (JP); Kei-ichi Ando, Nagoya (JP); Kensuke Yuuki, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 652 days.

(21) Appl. No.: 11/587,947

(22) PCT Filed: Apr. 26, 2005

(86) PCT No.: PCT/JP2005/007892

§ 371 (c)(1), (2), (4) Date: Oct. 27, 2006

(87) PCT Pub. No.: WO2005/105991

PCT Pub. Date: Nov. 10, 2005

(65) Prior Publication Data

US 2008/0248524 A1 Oct. 9, 2008

(30) Foreign Application Priority Data

Apr. 28, 2004 (JP) ............................. 2004-134464

(51) Int. Cl.
| | |
|---|---|
| *C12N 9/14* | (2006.01) |
| *C12Q 1/00* | (2006.01) |
| *C12Q 1/68* | (2006.01) |
| *C12Q 1/34* | (2006.01) |
| *C12N 1/20* | (2006.01) |
| *C12N 15/00* | (2006.01) |
| *C12P 21/04* | (2006.01) |
| *C07H 21/04* | (2006.01) |

(52) U.S. Cl. .............................. 435/195; 435/4; 435/6; 435/18; 435/69.1; 435/71.1; 435/252.3; 435/320.1; 435/440; 536/23.2

(58) Field of Classification Search ................ None
See application file for complete search history.

(56) References Cited

U.S. PATENT DOCUMENTS 6,392,126 B1 * 5/2002 Mahajan ..................... 800/295

FOREIGN PATENT DOCUMENTS

| JP | 55-120788 | 9/1980 |
|---|---|---|
| WO | WO-01/09305 | 2/2001 |

OTHER PUBLICATIONS

Branden et al. Introduction to Protein Structure, Garland Publishing Inc., New York, p. 247, 1991.*
T. Fujishima, et al.; "Studies on Adenyldeaminase Produced by Molds;" *Amino Acid-Nucleic Acid*; vol. 16; 1967; pp. 45-55./Discussed in the specification./Partial translation.
M. Rosinová, et al.; "Adenosine Aminohydrolase from *Streptomyces aureofaciens;*" *Collection Czechoslov. Chem. Commun.*; vol. 43; 1978; pp. 2324-2329./Discussed in the specification.
Supplementary European Search Report dated Nov. 20, 2008, issued on the corresponding European application No. 05 73 7266.6.

* cited by examiner

*Primary Examiner*—Yong D. Pak
(74) *Attorney, Agent, or Firm*—Edwards Angell Palmer & Dodge LLP

(57) ABSTRACT

It is intended to provide a thermostable AMP deaminase originating in a microorganism. Namely, an AMP deaminase having the following characteristics. (1) Catalyzing the reaction: 5'-adenylic acid+$H_2O$→5'-inosinic acid+$NH_3$; (2) being stable at a temperature of 65° C. or below (in an acetate buffer (pH 5.6)); (3) having a molecular weight of 48,000±2,000 in gel filtration; and (4) having the optimum pH value at around 5.6 (in McIlvaine buffer).

6 Claims, 29 Drawing Sheets

FIG. 2

| | phosphatase / deaminase (mU) |
|---|---|
| *Asp.melleus* | 0.97 |
| *Str.murinus* | below detection limit of phosphatase |

(a)

(b)

(a)

elution with Butyl Sepharose (b)

elution with Superose 12

(a)

| Step | total activity($10^6$u) | total protein (mg) | specific activity ($10^6$u/mg) | yield (%) |
|---|---|---|---|---|
| crude enzyme | 105 | 592 | 0.177 | 100 |
| ammonium sulfate fraction | 89.9 | 150 | 0.598 | 85.9 |
| Butyl Sepharose (Frc.45-48) | 11.1 | 2.13 | 5.22 | 10.6 |
| Superose12 (Frc.15-16) | 1.91 | 0.112 | 17.0 | 1.82 |

| substrate | relative activity (%) |
|---|---|
| 5'AMP | 100 |
| 3'AMP | 18 |
| 2'AMP | 0 |
| 5'dAMP | 42 |
| ADP | 84 |
| ATP | 74 |
| Adenosine | 9 |
| Adenine | 0 |
| 3'5'cyclic AMP | 12 |
| 5'GMP | 0 |
| 5'UMP | 0 |
| 5'CMP | 0 |

FIG. 11

| | nuclease "AMANO" G<br>Penicillium citrinum | Deamizyme<br>Aspergillus melleus | deaminase<br>Streptomyces murinus |
|---|---|---|---|
| molecular weight gel filtration | | 275,000 | 48,000 |
| SDS-PAGE | | 75,000 | 60,000 |
| optimum pH | 5.0 | 5.6 | 5.6 |
| optimum temperature | 70°C | 50°C | 65°C |
| isoelectric point | | | 8.12 |
| Km Value | | 1.0mM | 0.95mM |
| Vmax | | $2.5 \times 10^8$ μ mol/min/mg | $3.5 \times 10^7$ μ mol/min/mg |

FIG. 12

| strain | treatment at 65° C | specificity to adenosine |
|---|---|---|
| | residual activity (%) | relative activity (%) ※ |
| Streptomyces griseus subsp. griseus | 11 | 13 |
| Streptomyces griseus | 6 | 24 |
| Streptomyces celluloflavus | 32 | 12 |
| Streptomyces murinus | 94 | 9 |
| Aspergillus melleus | 0 | 63 |

FIG. 13

N-terminal amino acid sequence 2nd candidate  N-terminus — A P P E E Q A T D A E E R T D — C-terminus
　　　　　　　　　　　　　　　　　　　　　　　　　　　　　T D　　　　　　D A G Y L internal amino acid sequence frc. 14  N-terminus — E A D D G D A E F R — C-terminus frc. 18  N-terminus — F G E V T A R H R G — C-terminus

FIG. 17

| | enzyme activity of culture supernatant (cultured for five days) |
|---|---|
| S. lividans TK24 | ND |
| pSVSAD/S. lividans TK24 (SAD-1) | 2912 U/μl |

FIG. 19

| substrate | relative activity (%) |
|---|---|
| 5'AMP | 100 |
| 3'AMP | 16 |
| 2'AMP | 0 |
| 5'dAMP | 74 |
| ADP | 101 |
| ATP | 71 |
| Adenosine | 16 |
| Adenine | 0 |
| 3'5'cyclicAMP | 10 |
| 5'GMP | 0 |
| 5'UMP | 0 |
| 5'CMP | 0 |

FIG. 21

Sequence Range: 1 to 3822

```
            10         20         30         40         50         60         70         80         90        100        110        120
     GCGGCCGCCG TTCGTGCTCA GTGGTGCCCG TGGTTCCCCG CGAGCCGGTG CAGGACCGCC CCCGCCATGG CCTCCTCGCC CCGGGCGTTG GGGTGCGCCG GGGCCGCGGG CGCGGCCGGC 130        140        150        160        170        180        190        200        210        220        230        240
     TGGAGCGGCT CGATCCAGCG GTCCGCGGGC GCCTTGCACA TGTCGTGGCC CACGGTCGGA CCGTATGTGT CCACGTACTC GGCGCGGTTG CGCCCGGCCA CCGTGCGCAG CATCAGGTTC 250        260        270        280        290        300        310        320        330        340        350        360
     AGCCCCTTCT CGGTGTCCCG CAGATAGGCG AAGTCGCCCT GTGCCGAAGGG GACCTGCGGG AAGCAGCCCA CCCCGTCGTC GGGCAGCAGA TCGGGGTAGC CGACGACCAC GACCCGGCCG 370        380        390        400        410        420        430        440        450        460        470        480
     TGCGGCGCCC GCGCGTGCAC GGCCGGCAGC ACCTCGGTGA CCTTCGGCGC GGTCCGCCGT ACCGCGAGCG CCAGCGCGTC CTGCCCGGAC GCCTCGTAGG AGCGCTCGCA GGGACTGCCC 490        500        510        520        530        540        550        560        570        580        590        600
     GTCGGGTCCT GGACACCGAG CCGGGCGCAG GTGGCGATGA TGGTGCCGAA CCCGACGTCG TTGCCGCCTA TTTGGAGCCGT CACCAGGTCC GTGTTCCGTG AAACGGCGTC CAGCTGGGGC 610        620        630        640        650        660        670        680        690        700        710        720
     CCGTTGGTGC CCTGGGCCTG CCACATCTGC ACGGTCGTCG CGCCCGAGCA GCTGACGTCG GTGAACGTCG TCGCCCTCGC CCGCCGCGCC ACCAGCGACG GGTAATTCCG GTCGGAGCGG 730        740        750        760        770        780        790        800        810        820        830        840
     GCGCAGTCGG CATCCACCTG GGTGGGTATG CCCGGGCCCG AGGTGTAGGA GTCGCCGAGC GCCACGTAGT CCAGGCGGTG GCCGCGGCCC GCCGGATGCC CGGCGGCCGG AGTGGTGGCG 850        860        870        880        890        900        910        920        930        940        950        960
     GCGGCGACCA GGGCGCAGCC GCCCACCACC GCCGCCAGGA CCGCCGCCCG CCGCCGGGCT CTCGCCCCGT CCGCCGGACG CCTGTCGTTC GTCATGGTTC CCCCCTGGGA CCGGTACACG 970        980        990       1000       1010       1020       1030       1040       1050       1060       1070       1080
     GCGGCGGACGG CGCCGGCCCT GAGCGGCCCT CACGCGATCG ACTGGGTCTG TATACCGTCC GGTAGGTCCC GCCGACCAGA AGCGCGAGCC CATGAGTTCG GGGGAGAACG CGGCGGGGAG 1090       1100       1110       1120       1130       1140       1150       1160       1170       1180       1190       1200
     CCGCCGGCGG GGCGCGGTGC CGGCGGCCGT GCCGACCCC CGCCCCGGC CTCAGGCGCC GGACCCGCGC ACGGCCGGCC CGGGCTCCTG GAGCAGCGAG TCGTCCTCCG GCCGGGCCCC 1210       1220       1230       1240       1250       1260       1270       1280       1290       1300       1310       1320
     GGACAGCCGG TGGCGTGCCG CGATCAGGGC CATGTCGACA TCCCGCGTCC CGGTGGCCAC GCACAGCGTG TACGAGATGT CCGCGAGCCG CTGCTGCGCG CTCGGGGTGC TCTCCTCGGC 1330       1340       1350       1360       1370       1380       1390       1400       1410       1420       1430       1440
     GCCGAGCAGC GCGAGGGTCT CGTACTGGGT GATGAGGTCC TTCAGCACGG CGGGGTGTGC CATCAGCATG GGGTCGGCCT CCTGGTGTCT CGCCGATCTA CGACGTCACA GGCGCGACTA 1450       1460       1470       1480       1490       1500       1510       1520       1530       1540       1550       1560
     CCCCGGCCGG CGCCCCGCAT GCCACCCCGG TGGTCCCCGG TCCCGCGCGC ACCGCCCTTT CCGGACAGGA AGACGGACAC GTCACCCGCA CGGGTGCTCT CCGGCCGGTA TGCGCCGGTC 1570       1580       1590       1600       1610       1620       1630       1640       1650       1660       1670
     GGGCCCCCGT CGCCGCCCTC CGTCGCTGAT CATGCACCTG TGAGTCTGCA CACCCGAAGT GCCGTACCGC GCCGGGTCGT TCCGGCC GTG CTC GGC ACC CTC AGT GTC CTG TCC
                                                                                                   M   L   G   T   L   S   V   L   S>

1680       1690       1700       1710       1720       1730       1740       1750       1760       1770
     CTG CTG TCC GCC CTG CCC GCC GCC GCG CAG CCC GCG CGT GCC GCG GCC CGG CCC GCC GCG CCG CCG CCC CGG CAG GCC ACG GCC GCC GAG GCG CGG ACC
      L   L   S   A   L   P   A   A   A   Q   P   A   R   A   A   A   R   P   A   A   P   P   P   R   Q   A   T   A   A   E   A   R   T>

1780       1790       1800       1810       1820       1830       1840       1850       1860       1870
     GAC GCC TAC CTC CGC TCG GTC AAG GAC CGG CCC GCG GCC CTG CGG GCC TTC TTC CGG CAG CTC CCC AAG GGC GGG GAC CTG CAC AAC CAC CTC TCC GGA
      D   A   Y   L   R   S   V   K   D   R   P   A   A   L   R   A   F   F   R   Q   L   P   K   G   G   D   L   H   N   H   L   S   G>

1880       1890       1900       1910       1920       1930       1940       1950       1960       1970
     GCG GTG AAC ACG GAC TAC CTC ATC GAG CTG GCC GCC GAG GAC GGC CTG TGC ATC GAC GCG ACG ATG ACC GCC GTC CCC TCG CCC TGC GGC CCC GGC ACG
      A   V   N   T   D   Y   L   I   E   L   A   A   E   D   G   L   C   I   D   A   T   M   T   A   V   P   S   P   C   G   P   G   T>

1980       1990       2000       2010       2020       2030       2040       2050       2060       2070
     CGC CCC GCC GCC GAC GCC CGC ACC GAC CGC GCC TTC CAC GAC GCG ATC GTG CGC GCC TGG TCC ATG CAG GAC TTC CCG CCC GAC GAG AAC GGG CAC GAC
      R   P   A   A   D   A   R   T   D   R   A   F   H   D   A   I   V   R   A   W   S   M   Q   D   F   P   P   D   E   N   G   H   D>

2080       2090       2100       2110       2120       2130       2140       2150       2160
     CAC TTC TTC GAC ACC TTC GGC AAG TTC GGC GAG GTC ACC TGG CGG CAC CGG GGC AAG CTG CTC GCG CAG GTC GCC GAC ACC GTC GTC GCC AAC AAC CAG
      H   F   F   D   T   F   G   K   F   G   E   V   T   W   R   H   R   G   K   L   L   A   Q   V   A   D   T   V   V   A   N   N   Q>

2170       2180       2190       2200       2210       2220       2230       2240       2250       2260
     TCG TAC CTG GAG ACG ATG GTC ACC CCC GCC TCC GAC GGC GCC AAG CAA CTC GCC GAC CAG GTG GGC TGG GAC GCC GAT CTG ACC GCC CTG CAC CGC AAG
      S   Y   L   E   T   M   V   T   P   A   S   D   G   A   K   Q   L   A   D   Q   V   G   W   D   A   D   L   T   A   L   H   R   K>

2270       2280       2290       2300       2310       2320       2330       2340       2350       2360
     CTG GCC GCG GGC GGC AAG CTG GAC AAG CTG GTC GCC GAC GCC CGC AAG GAC GCC GAC GGC GAC GCC GAG TTC CGC GAC ACC GAG CAC TGC GGC ACC
      L   A   A   G   G   K   L   D   K   L   V   A   D   A   R   K   E   A   D   D   G   D   A   E   F   R   A   T   E   H   C   G   T>

2370       2380       2390       2400       2410       2420       2430       2440       2450       2460
     GCG AAG GCC CGG CCC GCC TGC GGG CTC ACG GTC CGC TGG ATC TCC CAG GCC AGC CGG GGC AGT TCA CCG GTG CGG GTC TTC ACC CAG GTG GAC CTC GGC
      A   K   A   R   P   A   C   G   L   T   V   R   W   I   S   Q   A   S   R   G   S   S   P   V   R   V   F   T   Q   L   D   L   G>

2470       2480       2490       2500       2510       2520       2530       2540       2550       2560
     ATG CGG CTC GCC GAG GCG GAC TCC CGC TTC GTC GCC GTC AAC CTG GTG CAG CCG GAG GAC TGG GAC AGC TCG CTG GAG AAC TAC AGC CTC CAG ATG CGC
      M   R   L   A   E   A   D   S   R   F   V   A   V   N   L   V   Q   P   E   D   W   D   S   S   L   E   N   Y   S   L   Q   M   R>

2570       2580       2590       2600       2610       2620       2630       2640       2650       2660
     ATG GTC GGC TAT CTG CGC ACC GTG TAC CCG AAG GCC CAT GTC ACC CTG CAC GCG GGC GAG TTG TGG CCC GGA CTG GTC AAG CCC GAG GCG CTG AAG TTC
      M   V   G   Y   L   R   T   V   Y   P   K   A   H   V   T   L   H   A   G   E   L   W   P   G   L   V   K   P   E   A   L   K   F>

2670       2680       2690       2700       2710       2720       2730       2740       2750       2760
     CAT ATC GCC GAG GCC GTG GAC ATC GCG CAC ACC CAG CGC GTC GGA CAC CGT GTC GAC CTC GTC CAC GAG GAC AAC TGG CAG GCC GCC GCC ACC ATG
      H   I   A   E   A   V   D   I   A   H   T   Q   R   V   G   H   G   V   D   L   V   H   E   D   N   W   Q   R   T   A   R   T   M>

2770       2780       2790       2800       2810       2820       2830       2840       2850       2860
     GCG GCC CGG CAG ATC GCC GTC GAG GTG CCC TTC TCC AGC AAC GCC CAG ATC CTC GGC GTC AAG GGT GCC GAG CAC CCC TTC ACG ACC TAC CGC CGC TAC
      A   A   R   Q   I   A   V   E   V   P   F   S   S   N   A   Q   I   L   G   V   K   G   A   E   H   P   F   T   T   Y   R   R   Y>

2870       2880       2890       2900       2910       2920       2930       2940       2950       2960
     GGC GTC CCG GTC GTC CTC GCC ACC GAC GAC CCC GGT GTC TCG CGC ATC GAC ATC AGC CAC GAG TAC CAG TAC GCC GCC GCC ACC TAC GGC CTC GGC TAC
      G   V   P   V   V   L   A   T   D   D   P   G   V   S   R   I   D   I   S   H   E   Y   Q   Y   A   A   A   T   Y   G   L   G   Y>

2970       2980       2990       3000       3010       3020       3030       3040       3050       3060
     CCG GAG CTG AAG GAC CTG GCC CGC GCC TCC CTC CAG GCC TTC CTG CCC GGC GCG AGC CTG TCG CAG GGC AAC CCC ACC GCG GGC TAC CAC CCG
      P   E   L   K   D   L   A   R   A   S   L   Q   Y   A   F   L   P   G   A   S   L   W   Q   G   N   P   T   A   G   Y   H   P>
```

FIG. 22

```
        3070        3080        3090        3100        3110        3120        3130        3140        3150
GTC GCG GCC TGC CGC GAG CGC GGA CAG CCC GTG CAC AGC CCC GCC TGC CGT CGG CTC CTC GAC GGC AGC GCG GCC CGG GCC CTC GAG TGG CGC
 V   A   A   C   R   E   R   P   G   Q   P   V   H   S   P   A   C   R   R   L   L   D   G   S   A   R   A   R   L   E   W   R>

3160        3170        3180        3190        3200        3210        3220        3230        3240        3250        3260
CAG GAG GCG GCC TTC GCG GCG TTC GAG CGG GCG CAC GCC CGG GGG TGA CCC GGT TCC GGC GCG GCC GTG C GGA CGG CCG C GGC CGG AAT C CAT CGA TTG G
 Q   E   A   A   F   A   A   F   E   R   A   H   A   R   G   *>

3270        3280        3290        3300        3310        3320        3330        3340        3350        3360        3370        3380
CCGAGAAGTA CGAGGTCATA CAACCGGATG ACCCGATTCC GTGCGGGAGC GCGGGTCGGG TCTTCGCCAT TACCCGGGCT TTGCGACGAC GTTTCCGGTA ACCCCACGCA CCCCCGTCGT 3390        3400        3410        3420        3430        3440        3450        3460        3470        3480        3490        3500
CACGGCCCGT ACCGTGCAGG GATGCCTCTC CCTTAAGATC ATCACATCGT CATCACATAG CCTTCACGGA ACGACCACTT TCGGCCGATC GGGTTCCGGG TCCTCGTGAC GGGGCAGACG 3510        3520        3530        3540        3550        3560        3570        3580        3590        3600        3610        3620
CGGTACGCGC CCCGCGCCTA GCCTCCCGGG CCATGCGATC ACCTCTGCTG AGACGGCCTC GTCTCACCGC CGTCCTCGCC CGTCCTCCTG CCGGTCCTCG CTTCAGCACC ATCGCCAGCG 3630        3640        3650        3660        3670        3680        3690        3700        3710        3720        3730        3740
CGGACCCGGA CCCGGCCGCC CTCACCTTCA GCACCGACAG CGCCACCACC ACCCCCGGTG GTTCGGTCAA GCTGTCGATG ACGGCTGACC ACAACAAGAC GTACGACGTC CTGTTCGTGT 3750        3760        3770        3780        3790        3800        3810        3820
ACCAGACGAT CGATCCGACC TGGCTGACCA CCCAGCGGTCC GGACCTGAAG TACAGCTTCG CCGGCTGCAC CCTGGCGGCC GC
```

FIG. 23

APPPRQATAEEARTDAYLRSVKDRPAALRAFFRQLPKGGDLHNHLSGAVNTDYLIELAAEDGLCIDATMTAVPSPCGPGT

RPAADARTDRAFHDAIVRAWSMQDFPPDENGHDHFFDTFGKFGEVTWRHRGKLLAQVADTVVANNQSYLETMVTPASDGA

KQLADQVGWDADLTALHRKLAAGGKLDKLVADARKEADDGDAEFRATEHCGTAKARPACGLTVRWISQASRGSSPVRVFT

QLDLGMRLAEADSRFVAVNLVQPEDWDSSLENYSLQMRMVGYLRTVYPKAHVTLHAGELWPGLVKPEALKFHIAEAVDIA

HTQRVGHGVDLVHEDNWQRTARTMAARQIAVEVPFSSNAQILGVKGAEHPFTYRRYGVPVVLATDDPGVSRIDISHEYQ

YAAATYGLGYPELKDLARASLQYAFLPGASLWQGNPTAQGYHPVAACRAERPGQPVHSAACRRLLDGSARARLEWRQEAA

FAAFERAHARG*

FIG. 24

MLGTLSVLSLLSALPAAAQPARAAARPAAPPPRQATAAEARTDAYLRSVKDRPAALRAFFRQLPKGGDLHNHLSGAVNTD

YLIELAAEDGLCIDATMTAVPSPCGPGTRPAADARTDRAFHDAIVRAWSMQDFPPDENGHDHFFDTFGKFGEVTWRHRGK

LLAQVADTVVANNQSYLETMVTPASDGAKQLADQVGWDADLTALHRKLAAGGKLDKLVADARKEADDGDAEFRATEHCGT

AKARPACGLTVRWISQASRGSSPVRVFTQLDLGMRLAEADSRFVAVNLVQPEDWDSSLENYSLQMRMVGYLRTVYPKAHV

TLHAGELWPGLVKPEALKFHIAEAVDIAHTQRVGHGVDLVHEDNWQRTARTMAARQIAVEVPFSSNAQILGVKGAEHPFT

TYRRYGVPVVLATDDPGVSRIDISHEYQYAAATYGLGYPELKDLARASLQYAFLPGASLWQGNPTAQGYHPVAACRAERP

GQPVHSAACRRLLDGSARARLEWRQEAAFAAFERAHARG*

FIG. 25

```
GCGGCCGCCGTTCGTGCTCAGTGGTGCCCGTGGTTCCCCGCGAGCCGGTGCAGGACCGCCCCCGCCATGGCCTCCTCGCC
CCGGGCGTTGGGGTGCGCCGGGGCCGCGGGCGCGGCCGGCTGGAGCGGCTCGATCCAGCGGTCCGCGGGCGCCTTGCACA
TGTCGTGGCCCACGGTCGGACCGTATGTGTCCACGTACTCGGCGCGGTTGCGCCCGGCCACCGTGCGCAGCATCAGGTTC
AGCCGCTTCTCGGTGTCCCGCAGATAGGCGAAGTCGCCCTGTGCGAAGGGGACCTGCGGGAAGCAGCCCACCCCGTCGTC
GGGCAGCAGATCGGGGTAGCCGACGACCACGACCCGGGCGTGCGGCGCCCGCGCGTGCACGGCCCGCAGCACCTCGGTGA
CCTTCGGCGCGGTCCGCCGTACCGCGAGCGCCAGCGCGTCCTGCCCGGACGCCTCGTAGGAGCGCTCGCAGGGACTGCCC
GTCGGGTCCTGGACACCGAGCCGGGCGCAGGTGGCGATGATGGTGCCGAACCCGACGTCGTTGCCGCCTATTTGGAGCGT
CACCAGGTCCGTGTTCCGTGAAACGGCGTCCAGCTGGGGCCCGTTGGTGCCCTGGGCCTGCCACATCTGCACGGTCGTCG
CGCCCGAGCAGCTGACGTCGGTGAACGTCGTCGCCCTCGCCCGCCGCGCCACCAGCGACGGGTAATTCCGGTCGGAGCGG
GCGCAGTCGGCATCCACCTGGGTGGGTATGCCCGGGCCCGAGGTGTAGGAGTCGCCGAGCGCCACGTAGTCCAGGCGGTG
GCCGCGGCCCGCCGGATGCGCGGCGGCCGGAGTGGTGGCGGCGGCGACCAGGGCGCAGCCGCCCACCACCGCCGCCAGGA
CCGCCGCCCGCCGCGGGCTCTCGCCCCGTCCGCCGGACGCCTGTCGTTCGTCATGGTTCCCCCCTGGGACCGGTACACG
GCGCGGACGGCGCCGCCCTGGAGCGGCCCTCACGCGATCGACTGGGTCTGTATACCGTCCGGTAGGTCCCGCCGACCAGA
AGCGCGAGCCCATGAGTTCGGGGGAGAACGCGGCGGGGAGCCGCCGGCGGGGCGCGGTGCCGGCGGCGGTGCGCGACCCC
GCGCCCCGGCCTCAGGCGCCGGACGCGGCGACGGCCGGCGCGGGCTCCTGGAGCAGCGAGTCGTCCTCCGGCCGGGCCCC
GGACAGCCGGTGGCGTGCCGCGATCAGGGCCATGTCGACATCCCGCGTCCCGGTGGCCACGCACAGCGTGTACGAGATGT
CCGCGAGCCGCTGCTGCGCCCTCGGGGTGCTCTCCTCGGCGCCGAGCAGCGCGAGGGTCTCGTACTGGGTGATGAGGTCC
TTCAGCACGGCGGGGTGTGCCATCAGCATGGGGTCGGCCTCCTGGTGTCTCGCCGATCTACGACGTCACAGGCGCGACTA
CCCGGGCCGGCGCCCCGCATGCCACCCCGGTGGTCCCCGGTCCCGCGCGCACCGCCCCTTTCCGGACAGGAAGACGGACAC
GTCACCCGCACGGGTGCTCTCCGGCCGGTATGCGCCGGTCGGGCCCCCGTCGCCGCCCTCCGTCGCTGATCATGCACCTG
TGAGTCTGCACACCCGAAGTGCCGTACCGCGCCGGGTCGTTCCGGCCGTGCTCGGCACCCTCAGTGTCCTGTCCCTGCTG
TCCGCCCTGCCCGCCGCCGCGCAGCCCGCGCGTGCCGCGGCCCGGCCCGCCGCGCCGCCGCCCCGGCAGGCCACGGCCGC
CGAGGCGCGGACCGACGCCTACCTCCGCTCGGTCAAGGACCGGCCCGCGGCCCTGCGGGCCTTCTTCCGGCAGCTCCCCA
AGGGCGGGGACCTGCACAACCACCTCTCCGGAGCGGTGAACACGGACTACCTCATCGAGCTGGCCGCCGAGGACGGCCTG
TGCATCGACGCGACGATGACCGCCGTCCCCTCGCCCTGCGGCCCCGGCACGCGCCCCGCCGCCGACGCCCGCACCGACCG
CGCCTTCCACGACGCGATCGTGCGCGCCTGGTCCATGCAGGACTTCCCGCCCGACGAGAACGGGCACGACCACTTCTTCG
ACACCTTCGGCAAGTTCGGCGAGGTCACCTGGCGGCACCGGGGCAAGCTGCTCGCGCAGGTCGCCGACACCGTCGTCGCC
AACAACCAGTCGTACCTGGAGACGATGGTCACCCCCGCCTCCGACGGCGCCAAGCAACTCGCCGACCAGGTGGGCTGGGA
CGCCGATCTGACCGCCCTGCACCGCAAGCTGGCCGCGGGCGGCAAGCTGGACAAGCTGGTCGCGGACGCCCGCAAGGAGG
CCGACGACGGCGACGCCGAGTTCCGCGCCACCGAGCACTGCGGCACCGCGAAGGCCCGGCCCGCCTGCGGGCTCACGGTC
CGCTGGATCTCCCAGGCGTCCCGGGGCAGTTCACCGGTGCGGGTCTTCACCCAGCTGGACCTCGGCATGCGGCTCGCCGA
GGCGGACTCCCGCTTCGTCGCCGTCAACCTGGTGCAGCCGGAGGACTGGGACAGCTCGCTGGAGAACTACAGCCTCCAGA
TGCGCATGGTCGGCTATCTGCGCACCGTGTACCCGAAGGCCCATGTCACCCTGCACGCGGGCGAGTTGTGGCCCGGACTG
GTCAAGCCCGAGGCGCTGAAGTTCCATATCGCCCGAGGCGGTGGACATCGCGCACACCCAGCGCGTCGGACACGGTGTCGA
```

FIG. 26

CCTCGTCCACGAGGACAACTGGCAGCGCACGGCCCGCACCATGGGGCCGGCAGATGCCGTCGAGGTGCCCTTCTCCA

GCAACGCCCAGATCCTCGGCGTCAAGGGTGCCGAGCACCCCTCAGCGACGTACCGCCGCTACGGGTCCCGGTCGTCCTC

GCCACCGACGACCCCGGTGTCTCGGCGCATCGACATCAGCCACGAGTACCCAGTACGCCGCCACCTACGGCCTCGGCTA

CCCGGAGCTGAAGGACCTGGCCCGCGCTCCCCTGCCGCCCTTCCTGCCGGCGAGCCTGTGGCAGGCAACCCCA

CCGCCCAGGGCTACCACCCGGTCGCGGCCCTGCCGCCCGACAGCCCGTGCACAGCGGCCTGCCGTCGG

CTCCTCGACGGGCAGCGGCCCGTGCGGGCCCGGTTCGGGCGTTCGGGCGTCGAGCGGGCCACGCCCG

GGGGTGACCCGGTTCCGGGCCGGGGAGCGCGGGTCGGGTCTTCGCCATTACCCGGGCTTTGCCGACGACGTTCCGGTA

CAACCGGATGACCCGATTCCGTGCGGGGAGCGCGGGTCGGGTCTTCGCCATTACCCGGGCTTTGCCGACGACGTTCCGGTA

ACCCCACGCACCCCGTCGTCACGGCCCGTACCGTGCAGGGATGCCTCTCCCTTAAGATCATCACATGTCATCACATAG

CCTTCACGGAACGACCACTTTCGGCCGATCGCTTCCGGTCCTCGTGACGGGCAGACGCGGTACGCCCGCGCCTA

GCCTCCCGGGCCATGCCGATCACCCTCTGCTGAGACGCCTCGGTCTCACCGCCCTCGTCCTCCGCCGTCTTCGG

CTTCAGCACCATCGCCAGCGGGACCCGCCCCTCACCTTCAGCACCGACCAGCGCCACCACCCCCGGTG

GTTCGGTCAAGCTGTCGATGACGCTGACCAACAAGACGTACGACGTCCTGTTCGTTGTACCAGACGATCCGACC

TGGCTGACCACCCAGGTCCGGACCTGAAGTACAGCTTCGCCGGCTGCACCCTGGCGGCCGC

FIG. 27

```
GCGGCCGCCGTTCGTGCTCAGTGGTGCCCGTGGTTCCCCGCGAGCCGGTGCAGGACCGCCCCCGCCATGGCCTCCTCGCC
CCGGGCGTTGGGGTGCGCCGGGGCCGCGGGCGCGGCCGGCTGGAGCGGCTCGATCCAGCGGTCCGCGGGCGCCTTGCACA
TGTCGTGGCCCACGGTCGGACCGTATGTGTCCACGTACTCGGCGCGGTTGCGCCCGGCCACCGTGCGCAGCATCAGGTTC
AGCCGCTTCTCGGTGTCCCGCAGATAGGCGAAGTCGCCCTGTGCGAAGGGGACCTGCGGGAAGCAGCCCACCCCGTCGTC
GGGCAGCAGATCGGGGTAGCCGACGACCACGACCCGGGCGTGCGGCGCCCGCGCGTGCACGGCCCGCAGCACCTCGGTGA
CCTTCGGCGCGGTCCGCCGTACCGCGAGCGCCAGCGCGTCCTGCCCGGACGCCTCGTAGGAGCGCTCGCAGGGACTGCCC
GTCGGGTCCTGGACACCGAGCCGGGCGCAGGTGGCGATGATGGTGCCGAACCCGACGTCGTTGCCGCCTATTTGGAGCGT
CACCAGGTCCGTGTTCCGTGAAACGGCGTCCAGCTGGGGCCCGTTGGTGCCCTGGGCCTGCCACATCTGCACGGTCGTCG
CGCCCGAGCAGCTGACGTCGGTGAACGTCGTCGCCCTCGCCCGCCGCGCCACCAGCGACGGGTAATTCCGGTCGGAGCGG
GCGCAGTCGGCATCCACCTGGGTGGGTATGCCCGGGCCCGAGGTGTAGGAGTCGCCGAGCGCCACGTAGTCCAGGCGGTG
GCCGCGGCCCGCCGGATGCGCGGCGGCCGGAGTGGTGGCGGCGGCGACCAGGGCGCAGCCGCCCACCACCGCCGCCAGGA
CCGCCGCCCGCCGCCGGGCTCTCGCCCCGTCCGCCGGACGCCTGTCGTTCGTCATGGTTCCCCCCTGGGACCGGTACACG
GCGCGGACGGCGCCGCCCTGGAGCGGCCCTCACGCGATCGACTGGGTCTGTATACCGTCCGGTAGGTCCCGCCGACCAGA
AGCGCGAGCCCATGAGTTCGGGGGAGAACGCGGCGGGGAGCCGCCGGCGGGGCGCGGTGCCGGCGGCGGTGCGCGACCCC
GCGCCCCGGCCTCAGGCGCCGGACGCGGCGACGGCCGGCGCGGGCTCCTGGAGCAGCGAGTCGTCCTCCGGCCGGGCCCC
GGACAGCCGGTGGCGTGCCGCGATCAGGGCCATGTCGACATCCCGCGTCCCGGTGGCCACGCACAGCGTGTACGAGATGT
CCGCGAGCCGCTGCTGCGCCCTCGGGGTGCTCTCCTCGGCGCCGAGCAGCGCGAGGGTCTCGTACTGGGTGATGAGGTCC
TTCAGCACGGCGGGGTGTGCCATCAGCATGGGGTCGGCCTCCTGGTGTCTCGCCGATCTACGACGTCACAGGCGCGACTA
CCCGGGCCGGCGCCCCGCATGCCACCCCGGTGGTCCCCGGTCCCGCGCGCACCGCCCTTTCCGGACAGGAAGACGGACAC
GTCACCCGCACGGGTGCTCTCCGGCCGGTATGCGCCGGTCGGGCCCCCGTCGCCGCCCTCCGTCGCTGATCATGCACCTG
TGAGTCTGCACACCCGAAGTGCCGTACCGCGCCGGGTCGTTCCGGCC
```

FIG. 28

```
GTGCTGGGCACCCTCAGTGTCCTGTCCTGTCCGCCCTGCTGTCCGCCGCCCTGCCCGCCGGCAGCCCGCGCGTGCCGGCGGCCCGGCC
CGCCGCGCCGCCGGCAGCCCACGGCCCCGGAGGCGCGGACCGACGCCTACCTCCGCTCGTCAAGGACCGGCCCG
CGGCCCTGCGGGCCTTCTCCGGCAGCTCCCCAAGGGCGGGACCTGCACAACCACCTCTCCGAGCGGTGAACACGGAC
TACCTCATCGAGCTGGCCGCCGAGGACGGCCTGTGCATCGACGATGACCGCGTCCCCTCGCCTGCGGCCCCGG
CACGGCGCCCCGCCCGACGCCCGCACCCGACGGCCCTTCCACGACGGATCGTGCGGCGCCTGTCCATGCAGGACTTCC
CGCCCGACGAGAACGGGCACGACCACTTCTTCGACACCTTCGGCCAAGTTCGGCGAGGTCACCTGCCGCCACCGGGGCAAG
CTGCTCGCGCAGGTCGCCGACACCGTCGTCCAACAACCAGTCGTACCTGGAGACGATGGTCACCCCCGCCTCCGACGG
CGCCAAGCAACTCGCCGACCAGGTGGGCTGGACGCCGATCTGACCCGCTGCACCGCAAGCTGGCCGCGGGCGGCAAGC
TGGACAAGCTGTCGCGGACGCCCGCAAGGAGCCCGACGCCGAGTTCGGCCCACCGAGCACTGCGGCACC
GCGAAGGCCCGCCCTGCGGCTCACGGTCGCGCTGGATCTCCCAGGCGTCCCGGGCAGTTCACCGGTGCGGGTCTT
CACCCAGCTGGACCTCGGCATGCGGCTCGCCCGAGGCGGACTCGTTGTCGCGCTGAACCTGGTGCAGCCGGAGGACT
GGGACAGCTCGCTGGAGAACTACAGCCTCAGATGCGCATGTGTCGGCTATCTCGCACCGTGTACCGAAGGCCCATGTC
ACCCTGCACGCGGGCGAGTTGTGCCAGCCTGGTCAAGCCCGAGGCGCTGAAGTTCCATATCGCCGAGGCGGTGGACAT
CGGCACACCCAGCGCGTCGAGGTGTGTCGACCTGCTCCACGAGGACAACTGGCACCCCCGACCACCATGGCGG
CCGGGCAGATCGCCGTCGAGGTGCCCTTCTCCAGCAACGCCCAGATCCTCGGCGTCAAGGTGCCGAGCACCCCTTCACG
ACGTACCGCGCTACGGCCTCCCGGTGTCCTGGCCACCGAGCCTGTCTCGGCATGACATCAGCCACGAGTA
CCAGTACCGCCCGCCCACCTACGGCCTCGGGCTACCGGCAGCTGAAGGACCTGGCCCGGAGCCTCCCTCCAGTACGCCTTCC
TGCCCGGGGAGCCTGTGCAGGGCAATCCCACCCACCCCGGCCGGGCCTACCACCCGGTGCCGCGGCCTGCCGGCCGAGCGCCCC
GGACAGCCCGTGCACAGCGGCCTGCCGTCCTGCAGGCGCCCTGGGGCCCGGGCCTGAGTGGCCCAGGAGGC
CGCGTTCGCGGGGCGTTCGAGCGGGCACGCCCGGGGTGA
```

FIG. 29

CCGGTTCCGGCCGGCCGTGCGGACGGCCGGGCCGGAATGCATCGATTGGCCGAGAAGTACGAGGTCATACAACCGG

ATGACCCGATTCCGTGCGGGAGCGCGGGTCGGGTCTTCGCCATTACCCGGGCTTTGCGACGACGTTTCCGGTAACCCCAC

GCACCCCGTCGTCACGGCCCGTGCAGGGATGCCTCCCTTAAGATCATCATCACATCGTCATCACATAGCCTTCAC

GGAACGACCACTTTCGGCGATCGCGTTCCGGGTCCTCGTGACGGGCAGACGCGGTACGCCCCGCCCTAGCCTCCC

GGGCCATGCGATCACCTCTGCTGAGACGCCTCGGTCCTCCACCGCGTCCTCGCCGTCTTCGGCTTCAGC

ACCATCGCCAGCGGGACCCGGACCCCTCACCTTCAGCACCACAGGCCACCACCCCGGTGTTCGGT

CAAGCTGTCGATGACGCTGACCAACAACAAGACGTACGACGTCCTGTTCGTGTACCAGACGATCCGACCTGGCTGA

CCACCCAGGCTCCGGACCTGAAGTACAGCTTCGCCGGCTGCACCCTGGGGCCGC

SEQUENCE LISTING

<160> NUMBER OF SEQ ID NOS: 41

<210> SEQ ID NO 1
<211> LENGTH: 491
<212> TYPE: PRT
<213> ORGANISM: Streptomyces murinus

<400> SEQUENCE: 1

```
Ala Pro Pro Pro Arg Gln Ala Thr Ala Ala Glu Ala Arg Thr Asp Ala
1               5                   10                  15

Tyr Leu Arg Ser Val Lys Asp Arg Pro Ala Ala Leu Arg Ala Phe Phe
            20                  25                  30

Arg Gln Leu Pro Lys Gly Gly Asp Leu His Asn His Leu Ser Gly Ala
        35                  40                  45

Val Asn Thr Asp Tyr Leu Ile Glu Leu Ala Ala Glu Asp Gly Leu Cys
    50                  55                  60

Ile Asp Ala Thr Met Thr Ala Val Pro Ser Pro Cys Gly Pro Gly Thr
65                  70                  75                  80

Arg Pro Ala Ala Asp Ala Arg Thr Asp Arg Ala Phe His Asp Ala Ile
                85                  90                  95

Val Arg Ala Trp Ser Met Gln Asp Phe Pro Pro Asp Glu Asn Gly His
            100                 105                 110

Asp His Phe Phe Asp Thr Phe Gly Lys Phe Gly Glu Val Thr Trp Arg
        115                 120                 125

His Arg Gly Lys Leu Leu Ala Gln Val Ala Asp Thr Val Val Ala Asn
    130                 135                 140

Asn Gln Ser Tyr Leu Glu Thr Met Val Thr Pro Ala Ser Asp Gly Ala
145                 150                 155                 160

Lys Gln Leu Ala Asp Gln Val Gly Trp Asp Ala Asp Leu Thr Ala Leu
                165                 170                 175

His Arg Lys Leu Ala Ala Gly Gly Lys Leu Asp Lys Leu Val Ala Asp
            180                 185                 190

Ala Arg Lys Glu Ala Asp Asp Gly Asp Ala Glu Phe Arg Ala Thr Glu
        195                 200                 205

His Cys Gly Thr Ala Lys Ala Arg Pro Ala Cys Gly Leu Thr Val Arg
    210                 215                 220

Trp Ile Ser Gln Ala Ser Arg Gly Ser Ser Pro Val Arg Val Phe Thr
225                 230                 235                 240

Gln Leu Asp Leu Gly Met Arg Leu Ala Glu Ala Asp Ser Arg Phe Val
                245                 250                 255

Ala Val Asn Leu Val Gln Pro Glu Asp Trp Asp Ser Ser Leu Glu Asn
            260                 265                 270

Tyr Ser Leu Gln Met Arg Met Val Gly Tyr Leu Arg Thr Val Tyr Pro
        275                 280                 285

Lys Ala His Val Thr Leu His Ala Gly Glu Leu Trp Pro Gly Leu Val
    290                 295                 300

Lys Pro Glu Ala Leu Lys Phe His Ile Ala Glu Ala Val Asp Ile Ala
305                 310                 315                 320

His Thr Gln Arg Val Gly His Gly Val Asp Leu Val His Glu Asp Asn
                325                 330                 335

Trp Gln Arg Thr Ala Arg Thr Met Ala Ala Arg Gln Ile Ala Val Glu
            340                 345                 350

Val Pro Phe Ser Ser Asn Ala Gln Ile Leu Gly Val Lys Gly Ala Glu
```

```
              355                 360                 365
His Pro Phe Thr Thr Tyr Arg Arg Tyr Gly Val Pro Val Val Leu Ala
    370                 375                 380

Thr Asp Asp Pro Gly Val Ser Arg Ile Asp Ile Ser His Glu Tyr Gln
385                 390                 395                 400

Tyr Ala Ala Ala Thr Tyr Gly Leu Gly Tyr Pro Glu Leu Lys Asp Leu
                405                 410                 415

Ala Arg Ala Ser Leu Gln Tyr Ala Phe Leu Pro Gly Ala Ser Leu Trp
            420                 425                 430

Gln Gly Asn Pro Thr Ala Gln Gly Tyr His Pro Val Ala Ala Cys Arg
        435                 440                 445

Ala Glu Arg Pro Gly Gln Pro Val His Ser Ala Ala Cys Arg Arg Leu
    450                 455                 460

Leu Asp Gly Ser Ala Arg Ala Arg Leu Glu Trp Arg Gln Glu Ala Ala
465                 470                 475                 480

Phe Ala Ala Phe Glu Arg Ala His Ala Arg Gly
                485                 490

<210> SEQ ID NO 2
<211> LENGTH: 519
<212> TYPE: PRT
<213> ORGANISM: Streptomyces murinus

<400> SEQUENCE: 2

Met Leu Gly Thr Leu Ser Val Leu Ser Leu Leu Ser Ala Leu Pro Ala
1               5                   10                  15

Ala Ala Gln Pro Ala Arg Ala Ala Arg Pro Ala Ala Pro Pro Pro
                20                  25                  30

Arg Gln Ala Thr Ala Ala Glu Ala Arg Thr Asp Ala Tyr Leu Arg Ser
            35                  40                  45

Val Lys Asp Arg Pro Ala Ala Leu Arg Ala Phe Phe Arg Gln Leu Pro
    50                  55                  60

Lys Gly Gly Asp Leu His Asn His Leu Ser Gly Ala Val Asn Thr Asp
65                  70                  75                  80

Tyr Leu Ile Glu Leu Ala Ala Glu Asp Gly Leu Cys Ile Asp Ala Thr
                85                  90                  95

Met Thr Ala Val Pro Ser Pro Cys Gly Pro Gly Thr Arg Pro Ala Ala
                100                 105                 110

Asp Ala Arg Thr Asp Arg Ala Phe His Asp Ala Ile Val Arg Ala Trp
            115                 120                 125

Ser Met Gln Asp Phe Pro Pro Asp Glu Asn Gly His Asp His Phe Phe
    130                 135                 140

Asp Thr Phe Gly Lys Phe Gly Glu Val Thr Trp Arg His Arg Gly Lys
145                 150                 155                 160

Leu Leu Ala Gln Val Ala Asp Thr Val Val Ala Asn Asn Gln Ser Tyr
                165                 170                 175

Leu Glu Thr Met Val Thr Pro Ala Ser Asp Gly Ala Lys Gln Leu Ala
                180                 185                 190

Asp Gln Val Gly Trp Asp Ala Asp Leu Thr Ala Leu His Arg Lys Leu
        195                 200                 205

Ala Ala Gly Gly Lys Leu Asp Lys Leu Val Ala Asp Ala Arg Lys Glu
    210                 215                 220

Ala Asp Asp Gly Asp Ala Glu Phe Arg Ala Thr Glu His Cys Gly Thr
225                 230                 235                 240
```

```
Ala Lys Ala Arg Pro Ala Cys Gly Leu Thr Val Arg Trp Ile Ser Gln
            245                 250                 255
Ala Ser Arg Gly Ser Ser Pro Val Arg Val Phe Thr Gln Leu Asp Leu
        260                 265                 270
Gly Met Arg Leu Ala Glu Ala Asp Ser Arg Phe Val Ala Val Asn Leu
    275                 280                 285
Val Gln Pro Glu Asp Trp Asp Ser Ser Leu Glu Asn Tyr Ser Leu Gln
290                 295                 300
Met Arg Met Val Gly Tyr Leu Arg Thr Val Tyr Pro Lys Ala His Val
305                 310                 315                 320
Thr Leu His Ala Gly Glu Leu Trp Pro Gly Leu Val Lys Pro Glu Ala
            325                 330                 335
Leu Lys Phe His Ile Ala Glu Ala Val Asp Ile Ala His Thr Gln Arg
            340                 345                 350
Val Gly His Gly Val Asp Leu Val His Glu Asp Asn Trp Gln Arg Thr
        355                 360                 365
Ala Arg Thr Met Ala Ala Arg Gln Ile Ala Val Glu Val Pro Phe Ser
    370                 375                 380
Ser Asn Ala Gln Ile Leu Gly Val Lys Gly Ala Glu His Pro Phe Thr
385                 390                 395                 400
Thr Tyr Arg Arg Tyr Gly Val Pro Val Val Leu Ala Thr Asp Asp Pro
            405                 410                 415
Gly Val Ser Arg Ile Asp Ile Ser His Glu Tyr Gln Tyr Ala Ala Ala
            420                 425                 430
Thr Tyr Gly Leu Gly Tyr Pro Glu Leu Lys Asp Leu Ala Arg Ala Ser
        435                 440                 445
Leu Gln Tyr Ala Phe Leu Pro Gly Ala Ser Leu Trp Gln Gly Asn Pro
    450                 455                 460
Thr Ala Gln Gly Tyr His Pro Val Ala Ala Cys Arg Ala Glu Arg Pro
465                 470                 475                 480
Gly Gln Pro Val His Ser Ala Ala Cys Arg Arg Leu Leu Asp Gly Ser
            485                 490                 495
Ala Arg Ala Arg Leu Glu Trp Arg Gln Glu Ala Ala Phe Ala Ala Phe
            500                 505                 510
Glu Arg Ala His Ala Arg Gly
        515

<210> SEQ ID NO 3
<211> LENGTH: 3822
<212> TYPE: DNA
<213> ORGANISM: Streptomyces murinus

<400> SEQUENCE: 3
gcggccgccg ttcgtgctca gtggtgcccg tggttccccg cgagccggtg caggaccgcc        60
cccgccatgg cctcctcgcc ccgggcgttg gggtgcgccg gggccgcggg cgcggccggc       120
tggagcggct cgatccagcg gtccgcgggc gccttgcaca tgtcgtggcc cacggtcgga       180
ccgtatgtgt ccacgtactc ggcgcggttg cgcccggcca ccgtgcgcag catcaggttc       240
agccgcttct cggtgtcccg cagataggcg aagtcgccct gtgcgaaggg gacctgcggg       300
aagcagccca cccgtcgtc gggcagcaga tcggggtagc cgacgaccac gacccgggcg       360
tgcggcgccc gcgcgtgcac ggcccgcagc acctcggtga ccttcggcgc ggtccgccgt       420
accgcgagcg ccagcgcgtc ctgcccggac gcctcgtagg agcgctcgca gggactgccc       480
gtcgggtcct ggacaccgag ccgggcgcag gtggcgatga tggtgccgaa cccgacgtcg       540
```

-continued

| | |
|---|---|
| ttgccgccta tttggagcgt caccaggtcc gtgttccgtg aaacggcgtc cagctggggc | 600 |
| ccgttggtgc cctgggcctg ccacatctgc acggtcgtcg cgcccgagca gctgacgtcg | 660 |
| gtgaacgtcg tcgccctcgc ccgcgcgcc accagcgacg ggtaattccg gtcggagcgg | 720 |
| gcgcagtcgg catccacctg ggtgggtatg cccgggcccg aggtgtagga gtcgccgagc | 780 |
| gccacgtagt ccaggcggtg gccgcggccc gccggatgcg cggcggccgg agtggtggcg | 840 |
| gcggcgacca gggcgcagcc gcccaccacc gccgccagga ccgccgcccg ccgccgggct | 900 |
| ctcgccccgt ccgccggacg cctgtcgttc gtcatggttc cccccctggga ccggtacacg | 960 |
| gcgcggacgg cgccgccctg gagcggccct cacgcgatcg actgggtctg tataccgtcc | 1020 |
| ggtaggtccc gccgaccaga agcgcgagcc catgagttcg ggggagaacg cggcggggag | 1080 |
| ccgccggcgg ggcgcggtgc cggcggcggt gcgcgacccc gcgccccggc ctcaggcgcc | 1140 |
| ggacgcggcg acggccggcg cgggctcctg gagcagcgag tcgtcctccg gccgggcccc | 1200 |
| ggacagccgg tggcgtgccg cgatcagggc catgtcgaca tcccgcgtcc cggtggccac | 1260 |
| gcacagcgtg tacgagatgt ccgcgagccg ctgctgcgcc ctcggggtgc tctcctcggc | 1320 |
| gccgagcagc gcgagggtct cgtactgggt gatgaggtcc ttcagcacgg cggggtgtgc | 1380 |
| catcagcatg gggtcggcct cctggtgtct cgccgatcta cgacgtcaca ggcgcgacta | 1440 |
| cccgggccgg cgccccgcat gccaccccgg tggtccccgg tcccgcgcgc accgcccttt | 1500 |
| ccggacagga agacggacac gtcacccgca cgggtgctct ccggccggta tgcgccggtc | 1560 |
| gggcccccgt cgccgccctc cgtcgctgat catgcacctg tgagtctgca cacccgaagt | 1620 |
| gccgtaccgc gccgggtcgt tccggccgtg ctcggcaccc tcagtgtcct gtccctgctg | 1680 |
| tccgccctgc ccgccgccgc gcagcccgcg cgtgccgcgg cccggcccgc cgcgccgccg | 1740 |
| ccccggcagg ccacggccgc cgaggcgcgg accgacgcct acctccgctc ggtcaaggac | 1800 |
| cggcccgcgg ccctgcgggc cttcttccgg cagctcccca agggcgggga cctgcacaac | 1860 |
| cacctctccg gagcggtgaa cacggactac ctcatcgagc tggccgccga ggacggcctg | 1920 |
| tgcatcgacg cgacgatgac cgccgtcccc tcgccctgcg gccccggcac gcgccccgcc | 1980 |
| gccgacgccc gcaccgaccg cgccttccac gacgcgatcg tgcgcgcctg gtccatgcag | 2040 |
| gacttcccgc ccgacgagaa cgggcacgac cacttcttcg acaccttcgg caagttcggc | 2100 |
| gaggtcacct ggcggcaccg gggcaagctg ctcgcgcagg tcgccgacac cgtcgtcgcc | 2160 |
| aacaaccagt cgtacctgga gacgatggtc acccccgcct ccgacggcgc caagcaactc | 2220 |
| gccgaccagg tgggctggga cgccgatctg accgccctgc accgcaagct ggccgcgggc | 2280 |
| ggcaagctgg acaagctggt cgcggacgcc cgcaaggagg ccgacgacgg cgacgccgag | 2340 |
| ttccgcgcca ccgagcactg cggcaccgcg aaggcccggc ccgcctgcgg gctcacggtc | 2400 |
| cgctggatct cccaggcgtc ccggggcagt tcaccggtgc gggtcttcac ccagctggac | 2460 |
| ctcggcatgc ggctcgccga gcggactcc cgcttcgtcg ccgtcaacct ggtgcagccg | 2520 |
| gaggactggg acagctcgct ggagaactac agcctccaga tgcgcatggt cggctatctg | 2580 |
| cgcaccgtgt acccgaaggc ccatgtcacc ctgcacgcgg gcgagttgtg gcccggactg | 2640 |
| gtcaagcccg aggcgctgaa gttccatatc gccgaggcgg tggacatcgc gcacacccag | 2700 |
| cgcgtcggac acggtgtcga cctcgtccac gaggacaact ggcagcgcac cgcccgcacc | 2760 |
| atggcggccc ggcagatcgc cgtcgaggtg cccttctcca gcaacgccca gatcctcggc | 2820 |
| gtcaagggtg ccgagcaccc cttcacgacg taccgccgct acggcgtccc ggtcgtcctc | 2880 |

-continued

| | |
|---|---|
| gccaccgacg accccggtgt ctcgcgcatc gacatcagcc acgagtacca gtacgccgcc | 2940 |
| gccacctacg gcctcggcta cccggagctg aaggacctgg cccgcgcctc cctccagtac | 3000 |
| gccttcctgc ccggcgcgag cctgtggcag ggcaacccca ccgcccaggg ctaccacccg | 3060 |
| gtcgcggcct gccgcgccga gcgccccgga cagcccgtgc acagcgcggc ctgccgtcgg | 3120 |
| ctcctcgacg gcagcgcccg ggcgcgcctg gagtggcgcc aggaggccgc gttcgcggcg | 3180 |
| ttcgagcggg cgcacgcccg ggggtgaccc ggttccggcc gcggccgtgc ggacggccgc | 3240 |
| ggccggaatg catcgattgg ccgagaagta cgaggtcata caaccggatg acccgattcc | 3300 |
| gtgcgggagc gcgggtcggg tcttcgccat tacccgggct tgcgacgac gtttccggta | 3360 |
| accccacgca cccccgtcgt cacggcccgt accgtgcagg gatgcctctc ccttaagatc | 3420 |
| atcacatcgt catcacatag ccttcacgga acgaccactt tcggccgatc gcgttccggg | 3480 |
| tcctcgtgac ggggcagacg cggtacgcgc cccgcgccta gcctcccggg ccatgcgatc | 3540 |
| acctctgctg agacgcctcg gtctcaccgc cgtcctcgcc gtcgtcctcg ccgtcttcgg | 3600 |
| cttcagcacc atcgccagcg cggacccgga cccggccgcc ctcaccttca gcaccgacag | 3660 |
| cgccaccacc accccggtg gttcggtcaa gctgtcgatg acgctgacca acaacaagac | 3720 |
| gtacgacgtc ctgttcgtgt accagacgat cgatccgacc tggctgacca cccagcgtcc | 3780 |
| ggacctgaag tacagcttcg ccggctgcac cctggcggcc gc | 3822 |

<210> SEQ ID NO 4
<211> LENGTH: 1560
<212> TYPE: DNA
<213> ORGANISM: Streptomyces murinus

<400> SEQUENCE: 4

| | |
|---|---|
| gtgctcggca ccctcagtgt cctgtccctg ctgtccgccc tgcccgccgc cgcgcagccc | 60 |
| gcgcgtgccg cggcccggcc cgccgcgccg ccgccccggc aggccacggc cgccgaggcg | 120 |
| cggaccgacg cctacctccg ctcggtcaag gaccggcccg cggccctgcg ggccttcttc | 180 |
| cggcagctcc ccaagggcgg ggacctgcac aaccacctct ccggagcggt gaacacggac | 240 |
| tacctcatcg agctggccgc cgaggacggc ctgtgcatcg acgcgacgat gaccgccgtc | 300 |
| ccctcgccct gcggccccgg cacgcgcccc gccgccgacg cccgcaccga ccgcgccttc | 360 |
| cacgacgcga tcgtgcgcgc ctggtccatg caggacttcc cgcccgacga gaacgggcac | 420 |
| gaccacttct tcgacacctt cggcaagttc ggcgaggtca cctggcggca ccggggcaag | 480 |
| ctgctcgcgc aggtcgccga caccgtcgtc gccaacaacc agtcgtacct ggagacgatg | 540 |
| gtcacccccg cctccgacgg cgccaagcaa ctcgccgacc aggtgggctg ggacgccgat | 600 |
| ctgaccgccc tgcaccgcaa gctggccgcg gcgggcaagc tggacaagct ggtcgcggac | 660 |
| gcccgcaagg aggccgacga cggcgacgcc gagttccgcg ccaccgagca ctgcggcacc | 720 |
| gcgaaggccc ggcccgcctg cgggctcacg gtccgctgga tctcccaggc gtcccgggc | 780 |
| agttcaccgg tgcgggtctt cacccagctg gacctcggca tgcggctcgc cgaggcggac | 840 |
| tcccgcttcg tcgccgtcaa cctggtgcag ccggaggact gggacagctc gctggagaac | 900 |
| tacagcctcc agatgcgcat ggtcggctat ctgcgcaccg tgtacccgaa ggcccatgtc | 960 |
| accctgcacg cgggcgagtt gtggcccgga ctggtcaagc ccgaggcgct gaagttccat | 1020 |
| atcgccgagg cggtggacat cgcgcacacc cagcgcgtcg acacggtgt cgacctcgtc | 1080 |
| cacgaggaca actggcagcg caccgcccgc accatggcgg cccggcagat cgccgtcgag | 1140 |
| gtgcccttct ccagcaacgc ccagatcctc ggcgtcaagg gtgccgagca cccccttcacg | 1200 |

| acgtaccgcc | gctacggcgt | cccggtcgtc | ctcgccaccg | acgacccegg | tgtctcgcgc | 1260 |
| atcgacatca | gccacgagta | ccagtacgcc | gccgccacct | acggcctcgg | ctacccggag | 1320 |
| ctgaaggacc | tggcccgcgc | ctccctccag | tacgccttcc | tgcccggcgc | gagcctgtgg | 1380 |
| cagggcaacc | ccaccgccca | gggctaccac | ccggtcgcgg | cctgccgcgc | cgagcgcccc | 1440 |
| ggacagcccg | tgcacagcgc | ggcctgccgt | cggctcctcg | acggcagcgc | ccgggcgcgc | 1500 |
| ctggagtggc | gccaggaggc | cgcgttcgcg | gcgttcgagc | gggcgcacgc | ccgggggtga | 1560 |

<210> SEQ ID NO 5
<211> LENGTH: 1476
<212> TYPE: DNA
<213> ORGANISM: Streptomyces murinus

<400> SEQUENCE: 5

| gcgccgccgc | cccggcaggc | cacggccgcc | gaggcgcgga | ccgacgccta | cctccgctcg | 60 |
| gtcaaggacc | ggcccgcggc | cctgcgggcc | ttcttccggc | agctccccaa | gggcggggac | 120 |
| ctgcacaacc | acctctccgg | agcggtgaac | acggactacc | tcatcgagct | ggccgccgag | 180 |
| gacggcctgt | gcatcgacgc | gacgatgacc | gccgtcccct | cgccctgcgg | ccccggcacg | 240 |
| cgccccgccg | ccgacgcccg | caccgaccgc | gccttccacg | acgcgatcgt | gcgcgcctgg | 300 |
| tccatgcagg | acttcccgcc | cgacgagaac | gggcacgacc | acttcttcga | caccttcggc | 360 |
| aagttcggcg | aggtcaccctg | gcggcaccgg | ggcaagctgc | tcgcgcaggt | cgccgacacc | 420 |
| gtcgtcgcca | caaccagtc | gtacctggag | acgatggtca | ccccgcctc | cgacggcgcc | 480 |
| aagcaactcg | ccgaccaggt | gggctgggac | gccgatctga | ccgccctgca | ccgcaagctg | 540 |
| gccgcgggcg | gcaagctgga | caagctggtc | gcggacgccc | gcaaggaggc | cgacgacggc | 600 |
| gacgccgagt | ccgcgccac | cgagcactgc | ggcaccgcga | aggcccggcc | cgcctgcggg | 660 |
| ctcacggtcc | gctggatctc | ccaggcgtcc | cggggcagtt | caccggtgcg | ggtcttcacc | 720 |
| cagctggacc | tcggcatgcg | gctcgccgag | gcggactccc | gcttcgtcgc | cgtcaacctg | 780 |
| gtgcagccgg | aggactggga | cagctcgctg | gagaactaca | gcctccagat | gcgcatggtc | 840 |
| ggctatctgc | gcaccgtgta | cccgaaggcc | catgtcaccc | tgcacgcggg | cgagttgtgg | 900 |
| cccggactgg | tcaagcccga | ggcgctgaag | ttccatatcg | ccgaggcggt | ggacatcgcg | 960 |
| cacacccagc | gcgtcggaca | cggtgtcgac | ctcgtccacg | aggacaactg | gcagcgcacc | 1020 |
| gcccgcacca | tggcggcccg | gcagatcgcc | gtcgaggtgc | ccttctccag | caacgcccag | 1080 |
| atcctcggcg | tcaagggtgc | cgagcacccc | ttcacgacgt | accgccgcta | cggcgtcccg | 1140 |
| gtcgtcctcg | ccaccgacga | ccccggtgtc | tcgcgcatcg | acatcagcca | cgagtaccag | 1200 |
| tacgccgccg | ccacctacgg | cctcggctac | ccggagctga | aggacctggc | ccgcgcctcc | 1260 |
| ctccagtacg | ccttcctgcc | cggcgcgagc | ctgtggcagg | gcaacccccac | cgcccagggc | 1320 |
| taccacccgg | tcgcggcctg | ccgcgccgag | cgccccggac | agcccgtgca | cagcgcggcc | 1380 |
| tgccgtcggc | tcctcgacgg | cagcgcccgg | gcgcgcctgg | agtggcgcca | ggaggccgcg | 1440 |
| ttcgcggcgt | tcgagcgggc | gcacgcccgg | gggtga | | | 1476 |

<210> SEQ ID NO 6
<211> LENGTH: 26
<212> TYPE: DNA
<213> ORGANISM: Artificial
<220> FEATURE:
<223> OTHER INFORMATION: primer IS-F
<220> FEATURE:

```
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (18)..(18)
<223> OTHER INFORMATION: n stands for inosine
<220> FEATURE:
<221> NAME/KEY: misc_feature
<222> LOCATION: (21)..(21)
<223> OTHER INFORMATION: n stands for inosine

<400> SEQUENCE: 6
ttcggngagg tnacngcncg ncaymg                                  26

<210> SEQ ID NO 7
<211> LENGTH: 26
<212> TYPE: DNA
<213> ORGANISM: Artificial
<220> FEATURE:
<223> OTHER INFORMATION: Primer IS-R
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (21)..(21)
<223> OTHER INFORMATION: n stands for inosine

<400> SEQUENCE: 7
aactcngcgt cnccgtcrtc ngcytc                                  26

<210> SEQ ID NO 8
<211> LENGTH: 18
<212> TYPE: DNA
<213> ORGANISM: Artificial
<220> FEATURE:
<223> OTHER INFORMATION: Primer MAD-F1

<400> SEQUENCE: 8
aagcaactcg ccgaccag                                           18

<210> SEQ ID NO 9
<211> LENGTH: 18
<212> TYPE: DNA
<213> ORGANISM: Artificial
<220> FEATURE:
<223> OTHER INFORMATION: Primer MAD-F2

<400> SEQUENCE: 9
tggtccatgc aggacttc                                           18

<210> SEQ ID NO 10
<211> LENGTH: 18
<212> TYPE: DNA
<213> ORGANISM: Artificial
<220> FEATURE:
<223> OTHER INFORMATION: Primer MAD-F3
```

```
<400> SEQUENCE: 10
ctggagaact acagcctc                                               18

<210> SEQ ID NO 11
<211> LENGTH: 18
<212> TYPE: DNA
<213> ORGANISM: Artificial
<220> FEATURE:
<223> OTHER INFORMATION: Primer MAD-F4

<400> SEQUENCE: 11
cagatcctcg gcgtcaag                                               18

<210> SEQ ID NO 12
<211> LENGTH: 18
<212> TYPE: DNA
<213> ORGANISM: Artificial
<220> FEATURE:
<223> OTHER INFORMATION: Primer MAD-F5

<400> SEQUENCE: 12
ctccagtacg ccttcctg                                               18

<210> SEQ ID NO 13
<211> LENGTH: 18
<212> TYPE: DNA
<213> ORGANISM: Artificial
<220> FEATURE:
<223> OTHER INFORMATION: Primer MAD-F6

<400> SEQUENCE: 13
gtcgggtcct ggacaccg                                               18

<210> SEQ ID NO 14
<211> LENGTH: 18
<212> TYPE: DNA
<213> ORGANISM: Artificial
<220> FEATURE:
<223> OTHER INFORMATION: Primer MAD-F7

<400> SEQUENCE: 14
tataccgtcc ggtaggtc                                               18

<210> SEQ ID NO 15
<211> LENGTH: 18
<212> TYPE: DNA
<213> ORGANISM: Artificial
<220> FEATURE:
<223> OTHER INFORMATION: Primer MAD-F8

<400> SEQUENCE: 15
ggacaggaag acggacac                                               18

<210> SEQ ID NO 16
<211> LENGTH: 18
<212> TYPE: DNA
<213> ORGANISM: Artificial
<220> FEATURE:
<223> OTHER INFORMATION: Primer MAD-F9

<400> SEQUENCE: 16
gattggccga gaagtacg                                               18

<210> SEQ ID NO 17
```

```
<211> LENGTH: 18
<212> TYPE: DNA
<213> ORGANISM: Artificial
<220> FEATURE:
<223> OTHER INFORMATION: Primer MAD-R1

<400> SEQUENCE: 17
tggtcggcga gttgcttg                                               18

<210> SEQ ID NO 18
<211> LENGTH: 18
<212> TYPE: DNA
<213> ORGANISM: Artificial
<220> FEATURE:
<223> OTHER INFORMATION: Primer MAD-R2

<400> SEQUENCE: 18
cagggacagg acactgag                                               18

<210> SEQ ID NO 19
<211> LENGTH: 18
<212> TYPE: DNA
<213> ORGANISM: Artificial
<220> FEATURE:
<223> OTHER INFORMATION: Primer MAD-R3

<400> SEQUENCE: 19
gatgtcgaca tggccctg                                               18

<210> SEQ ID NO 20
<211> LENGTH: 18
<212> TYPE: DNA
<213> ORGANISM: Artificial
<220> FEATURE:
<223> OTHER INFORMATION: Primer MAD-R4

<400> SEQUENCE: 20
cccagtcgat cgcgtgag                                               18

<210> SEQ ID NO 21
<211> LENGTH: 18
<212> TYPE: DNA
<213> ORGANISM: Artificial
<220> FEATURE:
<223> OTHER INFORMATION: Primer MAD-R5

<400> SEQUENCE: 21
tggtcgttcc gtgaaggc                                               18

<210> SEQ ID NO 22
<211> LENGTH: 18
<212> TYPE: DNA
<213> ORGANISM: Artificial
<220> FEATURE:
<223> OTHER INFORMATION: Primer MAD-R6

<400> SEQUENCE: 22
ctcgaacgcc gcgaacgc                                               18

<210> SEQ ID NO 23
<211> LENGTH: 18
<212> TYPE: DNA
<213> ORGANISM: Artificial
<220> FEATURE:
<223> OTHER INFORMATION: Primer MAD-R7

<400> SEQUENCE: 23
```

```
ctgggtgtgc gcgatgtc                                                    18
```

<210> SEQ ID NO 24
<211> LENGTH: 18
<212> TYPE: DNA
<213> ORGANISM: Artificial
<220> FEATURE:
<223> OTHER INFORMATION: Primer MAD-R8

<400> SEQUENCE: 24

```
caccatcatc gccacctg                                                    18
```

<210> SEQ ID NO 25
<211> LENGTH: 10
<212> TYPE: PRT
<213> ORGANISM: Streptomyces murinus

<400> SEQUENCE: 25

```
Phe Gly Glu Val Thr Ala Arg His Arg Gly
1               5                   10
```

<210> SEQ ID NO 26
<211> LENGTH: 10
<212> TYPE: PRT
<213> ORGANISM: Streptomyces murinus

<400> SEQUENCE: 26

```
Glu Ala Asp Asp Gly Asp Ala Glu Phe Arg
1               5                   10
```

<210> SEQ ID NO 27
<211> LENGTH: 15
<212> TYPE: PRT
<213> ORGANISM: Streptomyces murinus

<400> SEQUENCE: 27

```
Ala Pro Pro Glu Glu Gln Ala Thr Asp Ala Glu Glu Arg Thr Asp
1               5                   10                  15
```

<210> SEQ ID NO 28
<211> LENGTH: 7
<212> TYPE: PRT
<213> ORGANISM: Streptomyces murinus

<400> SEQUENCE: 28

```
Thr Asp Asp Ala Gly Tyr Leu
1               5
```

<210> SEQ ID NO 29
<211> LENGTH: 10
<212> TYPE: PRT
<213> ORGANISM: Streptomyces murinus

<400> SEQUENCE: 29

```
Glu Ala Asp Asp Gly Asp Ala Glu Phe Arg
1               5                   10
```

<210> SEQ ID NO 30
<211> LENGTH: 10
<212> TYPE: PRT
<213> ORGANISM: Streptomyces murinus

<400> SEQUENCE: 30

```
Phe Gly Glu Val Thr Ala Arg His Arg Gly
```

<210> SEQ ID NO 31
<211> LENGTH: 3060
<212> TYPE: DNA
<213> ORGANISM: Streptomyces murinus

<400> SEQUENCE: 31

| | | | | | |
|---|---|---|---|---|---|
| gcggccgccg | ttcgtgctca | gtggtgcccg | tggttccccg | cgagccggtg | caggaccgcc | 60 |
| cccgccatgg | cctcctcgcc | ccgggcgttg | gggtgcgccg | gggccgcggg | cgcggccggc | 120 |
| tggagcggct | cgatccagcg | gtccgcgggc | gccttgcaca | tgtcgtggcc | cacggtcgga | 180 |
| ccgtatgtgt | ccacgtactc | ggcgcggttg | cgcccggcca | ccgtgcgcag | catcaggttc | 240 |
| agccgcttct | cggtgtcccg | cagataggcg | aagtcgccct | gtgcgaaggg | gacctgcggg | 300 |
| aagcagccca | ccccgtcgtc | gggcagcaga | tcggggtagc | cgacgaccac | gacccgggcg | 360 |
| tgcggcgccc | gcgcgtgcac | ggcccgcagc | acctcggtga | ccttcggcgc | ggtccgccgt | 420 |
| accgcgagcg | ccagcgcgtc | ctgcccggac | gcctcgtagg | agcgctcgca | gggactgccc | 480 |
| gtcgggtcct | ggacaccgag | ccgggcgcag | gtggcgatga | tggtgccgaa | cccgacgtcg | 540 |
| ttgccgccta | tttggagcgt | caccaggtcc | gtgttccgtg | aaacggcgtc | cagctggggc | 600 |
| ccgttggtgc | cctgggcctg | ccacatctgc | acggtcgtcg | cgcccgagca | gctgacgtcg | 660 |
| gtgaacgtcg | tcgccctcgc | ccgccgcgcc | accagcgacg | ggtaattccg | gtcggagcgg | 720 |
| gcgcagtcgg | catccacctg | ggtgggtatg | cccgggcccg | aggtgtagga | gtcgccgagc | 780 |
| gccacgtagt | ccaggcggtg | gccgcggccc | gccggatgcg | cggcggccgg | agtggtggcg | 840 |
| gcggcgacca | gggcgcagcc | gcccaccacc | gccgccagga | ccgccgcccg | ccgcgggct | 900 |
| ctcgccccgt | ccgccggacg | cctgtcgttc | gtcatggttc | cccctgggga | ccggtacacg | 960 |
| gcgcggacgg | cgccgccctg | gagcggccct | cacgcgatcg | actgggtctg | tataccgtcc | 1020 |
| ggtaggtccc | gccgaccaga | agcgcgagcc | catgagttcg | ggggagaacg | cggcggggag | 1080 |
| ccgccggcgg | ggcgcggtgc | cggcggccggt | gcgcgacccc | gcgccccggc | ctcaggcgcc | 1140 |
| ggacgcggcg | acggccggcg | cgggctcctg | gagcagcgag | tcgtcctccg | gccgggcccc | 1200 |
| ggacagccgg | tggcgtgccg | cgatcagggc | catgtcgaca | tcccgcgtcc | cggtggccac | 1260 |
| gcacagcgtg | tacgagatgt | ccgcgagccg | ctgctgcgcc | ctcggggtgc | tctcctcggc | 1320 |
| gccgagcagc | gcgagggtct | cgtactgggt | gatgaggtcc | ttcagcacgg | cggggtgtgc | 1380 |
| catcagcatg | gggtcggcct | cctggtgtct | cgccgatcta | cgacgtcaca | ggcgcgacta | 1440 |
| cccgggccgg | cgccccgcat | gccaccccg | tggtccccgg | tcccgcgcgc | accgcccttt | 1500 |
| ccggacagga | agacgacac | gtcacccgca | cgggtgctct | ccggccggta | tgcgccggtc | 1560 |
| gggcccccgt | cgccgccctc | cgtcgctgat | catgcacctg | tgagtctgca | cacccgaagt | 1620 |
| gccgtaccgc | gccgggtcgt | tccggccgtg | ctcggcaccc | tcagtgtcct | gtccctgctg | 1680 |
| tccgccctgc | ccgccgccgc | gcagcccgcg | cgtgccgcgg | cccggccccgc | cgcgccgccg | 1740 |
| ccccggcagg | ccacggccgc | cgaggcgcgg | accgacgcct | acctccgctc | ggtcaaggac | 1800 |
| cggcccgcgg | ccctgcgggc | cttcttccgg | cagctcccca | agggcgggga | cctgcacaac | 1860 |
| cacctctccg | gagcggtgaa | cacgactac | ctcatcgagc | tggccgccga | ggacggcctg | 1920 |
| tgcatcgacg | cgacgatgac | cgccgtcccc | tcgccctgcg | gccccggcac | gcgccccgcc | 1980 |
| gccgacgccc | gcaccgaccg | cgccttccac | gacgcgatcg | tgcgcgcctg | gtccatgcag | 2040 |
| gacttcccgc | ccgacgagaa | cgggcacgac | cacttcttcg | acaccttcgg | caagttcggc | 2100 |

```
gaggtcacct ggcggcaccg gggcaagctg ctcgcgcagg tcgccgacac cgtcgtcgcc    2160
aacaaccagt cgtacctgga gacgatggtc accccgcct ccgacggcgc caagcaactc     2220
gccgaccagg tgggctggga cgccgatctg accgccctgc accgaagct ggccgcgggc     2280 ggcaagctgg acaagctggt cgcggacgcc cgcaaggagg ccgacgacgg cgacgccgag    2340
ttccgcgcca ccgagcactg cggcaccgcg aaggcccggc ccgcctgcgg gctcacggtc    2400
cgctggatct cccaggcgtc ccggggcagt tcaccggtgc gggtcttcac ccagctggac    2460
ctcggcatgc ggctcgccga gcggactcc cgcttcgtcg ccgtcaacct ggtgcagccg     2520
gaggactggg acagctcgct ggagaactac agcctccaga tgcgcatggt cggctatctg    2580
cgcaccgtgt acccgaaggc ccatgtcacc ctgcacgcgg cgagttgtg cccggactg      2640 gtcaagcccg aggcgctgaa gttccatatc gccgaggcgg tggacatcgc gcacacccag    2700
cgcgtcggac acggtgtcga cctcgtccac gaggacaact ggcagcgcac cgcccgcacc    2760
atggcggccc ggcagatcgc cgtcgaggtg cccttctcca gcaacgccca gatcctcggc    2820
gtcaagggtg ccgagcaccc cttcacgacg taccgccgct acggcgtccc ggtcgtcctc    2880
gccaccgacg accccggtgt ctcgcgcatc gacatcagcc acgagtacca gtacgccgcc    2940
gccacctacg gcctcggcta cccggagctg aaggacctgg cccgcgcctc cctccagtac    3000
gccttcctgc ccggcgcgag cctgtggcag ggcaaccca ccgcccaggg ctaccacccg      3060
```

<210> SEQ ID NO 32
<211> LENGTH: 471
<212> TYPE: PRT
<213> ORGANISM: Streptomyces murinus

<400> SEQUENCE: 32

```
Met Leu Gly Thr Leu Ser Val Leu Ser Leu Ser Ala Leu Pro Ala
1               5                   10                  15

Ala Ala Gln Pro Ala Arg Ala Ala Arg Pro Ala Ala Pro Pro
            20                  25                  30

Arg Gln Ala Thr Ala Ala Glu Ala Arg Thr Asp Ala Tyr Leu Arg Ser
        35                  40                  45

Val Lys Asp Arg Pro Ala Ala Leu Arg Ala Phe Phe Arg Gln Leu Pro
    50                  55                  60

Lys Gly Gly Asp Leu His Asn His Leu Ser Gly Ala Val Asn Thr Asp
65                  70                  75                  80

Tyr Leu Ile Glu Leu Ala Ala Glu Asp Gly Leu Cys Ile Asp Ala Thr
                85                  90                  95

Met Thr Ala Val Pro Ser Pro Cys Gly Pro Gly Thr Arg Pro Ala Ala
            100                 105                 110

Asp Ala Arg Thr Asp Arg Ala Phe His Asp Ala Ile Val Arg Ala Trp
        115                 120                 125

Ser Met Gln Asp Phe Pro Pro Asp Glu Asn Gly His Asp His Phe Phe
    130                 135                 140

Asp Thr Phe Gly Lys Phe Gly Glu Val Thr Trp Arg His Arg Gly Lys
145                 150                 155                 160

Leu Leu Ala Gln Val Ala Asp Thr Val Val Ala Asn Asn Gln Ser Tyr
                165                 170                 175

Leu Glu Thr Met Val Thr Pro Ala Ser Asp Gly Ala Lys Gln Leu Ala
            180                 185                 190

Asp Gln Val Gly Trp Asp Ala Asp Leu Thr Ala Leu His Arg Lys Leu
        195                 200                 205
```

-continued

```
Ala Ala Gly Gly Lys Leu Asp Lys Leu Val Ala Asp Ala Arg Lys Glu
    210                 215                 220
Ala Asp Asp Gly Asp Ala Glu Phe Arg Ala Thr Glu His Cys Gly Thr
225                 230                 235                 240
Ala Lys Ala Arg Pro Ala Cys Gly Leu Thr Val Arg Trp Ile Ser Gln
                245                 250                 255
Ala Ser Arg Gly Ser Ser Pro Val Arg Val Phe Thr Gln Leu Asp Leu
            260                 265                 270
Gly Met Arg Leu Ala Glu Ala Asp Ser Arg Phe Val Ala Val Asn Leu
        275                 280                 285
Val Gln Pro Glu Asp Trp Asp Ser Ser Leu Glu Asn Tyr Ser Leu Gln
    290                 295                 300
Met Arg Met Val Gly Tyr Leu Arg Thr Val Tyr Pro Lys Ala His Val
305                 310                 315                 320
Thr Leu His Ala Gly Glu Leu Trp Pro Gly Leu Val Lys Pro Glu Ala
                325                 330                 335
Leu Lys Phe His Ile Ala Glu Ala Val Asp Ile Ala His Thr Gln Arg
            340                 345                 350
Val Gly His Gly Val Asp Leu Val His Glu Asp Asn Trp Gln Arg Thr
        355                 360                 365
Ala Arg Thr Met Ala Ala Arg Gln Ile Ala Val Glu Val Pro Phe Ser
    370                 375                 380
Ser Asn Ala Gln Ile Leu Gly Val Lys Gly Ala Glu His Pro Phe Thr
385                 390                 395                 400
Thr Tyr Arg Arg Tyr Gly Val Pro Val Val Leu Ala Thr Asp Asp Pro
                405                 410                 415
Gly Val Ser Arg Ile Asp Ile Ser His Glu Tyr Gln Tyr Ala Ala Ala
            420                 425                 430
Thr Tyr Gly Leu Gly Tyr Pro Glu Leu Lys Asp Leu Ala Arg Ala Ser
        435                 440                 445
Leu Gln Tyr Ala Phe Leu Pro Gly Ala Ser Leu Trp Gln Gly Asn Pro
    450                 455                 460
Thr Ala Gln Gly Tyr His Pro
465                 470
```

<210> SEQ ID NO 33
<211> LENGTH: 762
<212> TYPE: DNA
<213> ORGANISM: Streptomyces murinus

<400> SEQUENCE: 33

| | | | | | |
|---|---|---|---|---|---|
| gtcgcggcct | gccgcgccga | gcgccccgga | cagcccgtgc | acagcgcggc | ctgccgtcgg | 60 |
| ctcctcgacg | gcagcgcccg | ggcgcgcctg | gagtggcgcc | aggaggccgc | gttcgcggcg | 120 |
| ttcgagcggg | cgcacgcccg | ggggtgaccc | ggttccggcc | gcggccgtgc | ggacggccgc | 180 |
| ggccggaatg | catcgattgg | ccgagaagta | cgaggtcata | caaccggatg | acccgattcc | 240 |
| gtgcgggagc | gcgggtcggg | tcttcgccat | tacccgggct | tgcgacgac | gtttccggta | 300 |
| accccacgca | cccccgtcgt | cacggcccgt | accgtgcagg | gatgcctctc | ccttaagatc | 360 |
| atcacatcgt | catcacatag | ccttcacgga | acgaccactt | tcggccgatc | gcgttccggg | 420 |
| tcctcgtgac | ggggcagacg | cggtacgcgc | ccgcgccta | gcctcccggg | ccatgcgatc | 480 |
| acctctgctg | agacgcctcg | gtctcaccgc | cgtcctcgcc | gtcgtcctcg | ccgtcttcgg | 540 |
| cttcagcacc | atcgccagcg | cggacccgga | cccggccgcc | ctcaccttca | gcaccgacag | 600 |

```
cgccaccacc accccggtg gttcggtcaa gctgtcgatg acgctgacca acaacaagac    660
gtacgacgtc ctgttcgtgt accagacgat cgatccgacc tggctgacca cccagcgtcc    720
ggacctgaag tacagcttcg ccggctgcac cctggcggcc gc                        762
```

<210> SEQ ID NO 34
<211> LENGTH: 48
<212> TYPE: PRT
<213> ORGANISM: Streptomyces murinus

<400> SEQUENCE: 34

Val Ala Ala Cys Arg Ala Glu Arg Pro Gly Gln Pro Val His Ser Ala
1               5                   10                  15

Ala Cys Arg Arg Leu Leu Asp Gly Ser Ala Arg Ala Arg Leu Glu Trp
            20                  25                  30

Arg Gln Glu Ala Ala Phe Ala Ala Phe Glu Arg Ala His Ala Arg Gly
        35                  40                  45

<210> SEQ ID NO 35
<211> LENGTH: 491
<212> TYPE: PRT
<213> ORGANISM: Streptomyces murinus

<400> SEQUENCE: 35

Ala Pro Pro Pro Arg Gln Ala Thr Ala Ala Glu Ala Arg Thr Asp Ala
1               5                   10                  15

Tyr Leu Arg Ser Val Lys Asp Arg Pro Ala Ala Leu Arg Ala Phe Phe
            20                  25                  30

Arg Gln Leu Pro Lys Gly Gly Asp Leu His Asn His Leu Ser Gly Ala
        35                  40                  45

Val Asn Thr Asp Tyr Leu Ile Glu Leu Ala Ala Glu Asp Gly Leu Cys
    50                  55                  60

Ile Asp Ala Thr Met Thr Ala Val Pro Ser Pro Cys Gly Pro Gly Thr
65                  70                  75                  80

Arg Pro Ala Ala Asp Ala Arg Thr Asp Arg Ala Phe His Asp Ala Ile
                85                  90                  95

Val Arg Ala Trp Ser Met Gln Asp Phe Pro Pro Asp Glu Asn Gly His
            100                 105                 110

Asp His Phe Phe Asp Thr Phe Gly Lys Phe Gly Glu Val Thr Trp Arg
        115                 120                 125

His Arg Gly Lys Leu Leu Ala Gln Val Ala Asp Thr Val Val Ala Asn
    130                 135                 140

Asn Gln Ser Tyr Leu Glu Thr Met Val Thr Pro Ala Ser Asp Gly Ala
145                 150                 155                 160

Lys Gln Leu Ala Asp Gln Val Gly Trp Asp Ala Asp Leu Thr Ala Leu
                165                 170                 175

His Arg Lys Leu Ala Ala Gly Gly Lys Leu Asp Lys Leu Val Ala Asp
            180                 185                 190

Ala Arg Lys Glu Ala Asp Asp Gly Asp Ala Glu Phe Arg Ala Thr Glu
        195                 200                 205

His Cys Gly Thr Ala Lys Ala Arg Pro Ala Cys Gly Leu Thr Val Arg
    210                 215                 220

Trp Ile Ser Gln Ala Ser Arg Gly Ser Ser Pro Val Arg Val Phe Thr
225                 230                 235                 240

Gln Leu Asp Leu Gly Met Arg Leu Ala Glu Ala Asp Ser Arg Phe Val
                245                 250                 255

```
Ala Val Asn Leu Val Gln Pro Glu Asp Trp Asp Ser Ser Leu Glu Asn
            260                 265                 270

Tyr Ser Leu Gln Met Arg Met Val Gly Tyr Leu Arg Thr Val Tyr Pro
        275                 280                 285

Lys Ala His Val Thr Leu His Ala Gly Glu Leu Trp Pro Gly Leu Val
    290                 295                 300

Lys Pro Glu Ala Leu Lys Phe His Ile Ala Glu Ala Val Asp Ile Ala
305                 310                 315                 320

His Thr Gln Arg Val Gly His Gly Val Asp Leu Val His Glu Asp Asn
                325                 330                 335

Trp Gln Arg Thr Ala Arg Thr Met Ala Ala Arg Gln Ile Ala Val Glu
            340                 345                 350

Val Pro Phe Ser Ser Asn Ala Gln Ile Leu Gly Val Lys Gly Ala Glu
        355                 360                 365

His Pro Phe Thr Thr Tyr Arg Arg Tyr Gly Val Pro Val Val Leu Ala
    370                 375                 380

Thr Asp Asp Pro Gly Val Ser Arg Ile Asp Ile Ser His Glu Tyr Gln
385                 390                 395                 400

Tyr Ala Ala Thr Tyr Gly Leu Gly Tyr Pro Glu Leu Lys Asp Leu
                405                 410                 415

Ala Arg Ala Ser Leu Gln Tyr Ala Phe Leu Pro Gly Ala Ser Leu Trp
            420                 425                 430

Gln Gly Asn Pro Thr Ala Gln Gly Tyr His Pro Val Ala Ala Cys Arg
        435                 440                 445

Ala Glu Arg Pro Gly Gln Pro Val His Ser Ala Ala Cys Arg Arg Leu
    450                 455                 460

Leu Asp Gly Ser Ala Arg Ala Arg Leu Glu Trp Arg Gln Glu Ala Ala
465                 470                 475                 480

Phe Ala Ala Phe Glu Arg Ala His Ala Arg Gly
                485                 490

<210> SEQ ID NO 36
<211> LENGTH: 519
<212> TYPE: PRT
<213> ORGANISM: Streptomyces murinus

<400> SEQUENCE: 36

Met Leu Gly Thr Leu Ser Val Leu Ser Leu Leu Ser Ala Leu Pro Ala
1               5                   10                  15

Ala Ala Gln Pro Ala Arg Ala Ala Arg Pro Ala Ala Pro Pro
            20                  25                  30

Arg Gln Ala Thr Ala Ala Glu Ala Arg Thr Asp Ala Tyr Leu Arg Ser
        35                  40                  45

Val Lys Asp Arg Pro Ala Ala Leu Arg Ala Phe Phe Arg Gln Leu Pro
    50                  55                  60

Lys Gly Gly Asp Leu His Asn His Leu Ser Gly Ala Val Asn Thr Asp
65                  70                  75                  80

Tyr Leu Ile Glu Leu Ala Ala Glu Asp Gly Leu Cys Ile Asp Ala Thr
                85                  90                  95

Met Thr Ala Val Pro Ser Pro Cys Gly Pro Gly Thr Arg Pro Ala Ala
            100                 105                 110

Asp Ala Arg Thr Asp Arg Ala Phe His Asp Ala Ile Val Arg Ala Trp
        115                 120                 125

Ser Met Gln Asp Phe Pro Pro Asp Glu Asn Gly His Asp His Phe Phe
```

```
            130                 135                 140
Asp Thr Phe Gly Lys Phe Gly Glu Val Thr Trp Arg His Arg Gly Lys
145                 150                 155                 160

Leu Leu Ala Gln Val Ala Asp Thr Val Ala Asn Asn Gln Ser Tyr
                165                 170                 175

Leu Glu Thr Met Val Thr Pro Ala Ser Asp Gly Ala Lys Gln Leu Ala
                180                 185                 190

Asp Gln Val Gly Trp Asp Ala Asp Leu Thr Ala Leu His Arg Lys Leu
                195                 200                 205

Ala Ala Gly Gly Lys Leu Asp Lys Leu Val Ala Asp Ala Arg Lys Glu
210                 215                 220

Ala Asp Gly Asp Ala Glu Phe Arg Ala Thr Glu His Cys Gly Thr
225                 230                 235                 240

Ala Lys Ala Arg Pro Ala Cys Gly Leu Thr Val Arg Trp Ile Ser Gln
                245                 250                 255

Ala Ser Arg Gly Ser Ser Pro Val Arg Val Phe Thr Gln Leu Asp Leu
                260                 265                 270

Gly Met Arg Leu Ala Glu Ala Asp Ser Arg Phe Val Ala Val Asn Leu
                275                 280                 285

Val Gln Pro Glu Asp Trp Asp Ser Ser Leu Glu Asn Tyr Ser Leu Gln
                290                 295                 300

Met Arg Met Val Gly Tyr Leu Arg Thr Val Tyr Pro Lys Ala His Val
305                 310                 315                 320

Thr Leu His Ala Gly Glu Leu Trp Pro Gly Leu Val Lys Pro Glu Ala
                325                 330                 335

Leu Lys Phe His Ile Ala Glu Ala Val Asp Ile Ala His Thr Gln Arg
                340                 345                 350

Val Gly His Gly Val Asp Leu Val His Glu Asp Asn Trp Gln Arg Thr
                355                 360                 365

Ala Arg Thr Met Ala Ala Arg Gln Ile Ala Val Glu Val Pro Phe Ser
370                 375                 380

Ser Asn Ala Gln Ile Leu Gly Val Lys Gly Ala Glu His Pro Phe Thr
385                 390                 395                 400

Thr Tyr Arg Arg Tyr Gly Val Pro Val Leu Ala Thr Asp Asp Pro
                405                 410                 415

Gly Val Ser Arg Ile Asp Ile Ser His Glu Tyr Gln Tyr Ala Ala Ala
                420                 425                 430

Thr Tyr Gly Leu Gly Tyr Pro Glu Leu Lys Asp Leu Ala Arg Ala Ser
                435                 440                 445

Leu Gln Tyr Ala Phe Leu Pro Gly Ala Ser Leu Trp Gln Gly Asn Pro
450                 455                 460

Thr Ala Gln Gly Tyr His Pro Val Ala Ala Cys Arg Ala Glu Arg Pro
465                 470                 475                 480

Gly Gln Pro Val His Ser Ala Ala Cys Arg Leu Leu Asp Gly Ser
                485                 490                 495

Ala Arg Ala Arg Leu Glu Trp Arg Gln Glu Ala Ala Phe Ala Ala Phe
                500                 505                 510

Glu Arg Ala His Ala Arg Gly
            515

<210> SEQ ID NO 37
<211> LENGTH: 2720
<212> TYPE: DNA
<213> ORGANISM: Streptomyces murinus
```

<400> SEQUENCE: 37

```
gcggccgccg ttcgtgctca gtggtgcccg tggttccccg cgagccggtg caggaccgcc      60
cccgccatgg cctcctcgcc ccgggcgttg gggtgcgccg gggccgcggg cgcggccggc     120
tggagcggct cgatccagcg gtccgcgggc gccttgcaca tgtcgtggcc cacggtcgga     180
ccgtatgtgt ccacgtactc ggcgcggttg cgcccggcca ccgtgcgcag catcaggttc     240
agccgcttct cggtgtcccg cagataggcg aagtcgccct gtgcgaaggg gacctgcggg     300
aagcagccca ccccgtcgtc gggcagcaga tcggggtagc cgacgaccac gacccgggcg     360
tgcggcgccc gcgcgtgcac ggcccgcagc acctcggtga ccttcggcgc ggtccgccgt     420
accgcgagcg ccagcgcgtc ctgcccggac gcctcgtagg agcgctcgca gggactgccc     480
gtcgggtcct ggacaccgag ccgggcgcag gtggcgatga tggtgccgaa cccgacgtcg     540
ttgccgccta tttggagcgt caccaggtcc gtgttccgtg aaacggcgtc cagctggggc     600
ccgttggtgc cctgggcctg ccacatctgc acggtcgtcg cgcccgagca gctgacgtcg     660
gtgaacgtcg tcgccctcgc ccgccgcgcc accagcgacg ggtaattccg gtcggagcgg     720
gcgcagtcgg catccacctg ggtgggtatg cccgggcccg aggtgtagga gtcgccgagc     780
gccacgtagt ccaggcggtg gccgcggccc gccggatgcg cggcggccgg agtggtggcg     840
gcggcgacca gggcgcagcc gcccaccacc gccgccagga ccgccgcccg ccgccgggct     900
ctcgccccgt ccgccggacg cctgtcgttc gtcatggttc cccccctggga ccggtacacg     960
gcgcggacgg cgccgccctg gagcggccct cacgcgatcg actgggtctg tataccgtcc    1020
ggtaggtccc gccgaccaga agcgcgagcc catgagttcg ggggagaacg cggcggggag    1080
ccgccggcg ggcgcggtgc cggcggcggt gcgcgacccc gcgccccggc tcaggcgcc    1140
ggacgcggcg acggccggcg cgggctcctg gagcagcgag tcgtcctccg gccgggcccc    1200
ggacagccgg tggcgtgccg cgatcagggc catgtcgaca tcccgcgtcc cggtggccac    1260
gcacagcgtg tacgagatgt ccgcgagccg ctgctgcgcc ctcggggtgc tctcctcggc    1320
gccgagcagc gcgagggtct cgtactgggt gatgaggtcc ttcagcacgg cggggtgtgc    1380
catcagcatg gggtcggcct cctggtgtct cgccgatcta cgacgtcaca ggcgcgacta    1440
cccgggccgc cgccccgcat gccacccccgg tggtccccgg tcccgcgcgc accgcccttt    1500
ccggacagga agacggacac gtcacccgca cgggtgctct ccggccggta tgcgccggtc    1560
gggcccccgt cgccgccctc cgtcgctgat catgcacctg tgagtctgca cacccgaagt    1620
gccgtaccgc gccgggtcgt tccggccgtg ctcggcaccc tcagtgtcct gtccctgctg    1680
tccgccctgc ccgccgccgc gcagcccgcg cgtgccgcgg cccggcccgc cgcgccgccg    1740
ccccggcagg ccacggccgc cgaggcgcgg accgacgcct acctccgctc ggtcaaggac    1800
cggcccgcgg ccctgcgggc cttcttccgg cagctcccca agggcgggga cctgcacaac    1860
cacctctccg gagcggtgaa cacggactac ctcatcgagc tggccgccga ggacggcctg    1920
tgcatcgacg cgacgatgac cgccgtcccc tcgccctgcg gccccggcac gcgccccgcc    1980
gccgacgccc gcaccgaccg cgccttccac gacgcgatcg tgcgcgcctg gtccatgcag    2040
gacttcccgc ccgacgagaa cgggcacgac cacttcttcg acaccttcgg caagttcggc    2100
gaggtcacct ggcggcaccg gggcaagctg ctcgcgcagg tcgccgacac cgtcgtcgcc    2160
aacaaccagt cgtacctgga gacgatggtc accccgcct ccgacggcgc caagcaactc    2220
gccgaccagg tgggctggga cgccgatctg accgccctgc accgcaagct ggccgcgggc    2280
```

```
ggcaagctgg acaagctggt cgcggacgcc cgcaaggagg ccgacgacgg cgacgccgag    2340
ttccgcgcca ccgagcactg cggcaccgcg aaggcccggc ccgcctgcgg gctcacggtc    2400
cgctggatct cccaggcgtc ccggggcagt tcaccggtgc gggtcttcac ccagctggac    2460
ctcggcatgc ggctcgccga ggcggactcc cgcttcgtcg ccgtcaacct ggtgcagccg    2520
gaggactggg acagctcgct ggagaactac agcctccaga tgcgcatggt cggctatctg    2580
cgcaccgtgt acccgaaggc ccatgtcacc ctgcacgcgg gcgagttgtg gcccggactg    2640
gtcaagcccg aggcgctgaa gttccatatc gccgaggcgg tggacatcgc gcacacccag    2700
cgcgtcggac acggtgtcga                                                2720

<210> SEQ ID NO 38
<211> LENGTH: 1102
<212> TYPE: DNA
<213> ORGANISM: Streptomyces murinus

<400> SEQUENCE: 38
cctcgtccac gaggacaact ggcagcgcac cgcccgcacc atggcggccc ggcagatcgc      60
cgtcgaggtg cccttctcca gcaacgccca gatcctcggc gtcaagggtg ccgagcaccc     120
cttcacgacg taccgccgct acggcgtccc ggtcgtcctc gccaccgacg accccggtgt     180
ctcgcgcatc gacatcagcc acgagtacca gtacgccgcc gccacctacg gcctcggcta     240
cccggagctg aaggacctgg cccgcgcctc cctccagtac gccttcctgc ccggcgcgag     300
cctgtggcag ggcaaccccca ccgcccaggg ctaccaccg gtcgcggcct gccgcgccga     360
gcgccccgga cagcccgtgc acagcgcggc ctgccgtcgg ctcctcgacg gcagcgcccg     420
ggcgcgcctg gagtggcgcc aggaggccgc gttcgcggcg ttcgagcggg cgcacgcccg     480
ggggtgaccc ggttccggcc gcggccgtgc ggacggccgc ggccggaatg catcgattgg     540
ccgagaagta cgaggtcata caaccggatg acccgattcc gtgcgggagc gcgggtcggg     600
tcttcgccat tacccgggct ttgcgacgac gtttccggta accccacgca ccccgtcgt     660 cacggcccgt accgtgcagg gatgcctctc ccttaagatc atcacatcgt catcacatag     720
ccttcacgga acgaccactt tcggccgatc gcgttccggg tcctcgtgac ggggcagacg     780
cggtacgcgc cccgcgccta gcctcccggg ccatgcgatc acctctgctg agacgcctcg     840
gtctcaccgc cgtcctcgcc gtcgtcctcg ccgtcttcgg cttcagcacc atcgccagcg     900
cggacccgga cccggccgcc ctcaccttca gcaccgacag cgccaccacc accccggtg     960 gttcggtcaa gctgtcgatg acgctgacca acaacaagac gtacgacgtc ctgttcgtgt    1020
accagacgat cgatccgacc tggctgacca cccagcgtcc ggacctgaag tacagcttcg    1080
ccggctgcac cctggcggcc gc                                              1102

<210> SEQ ID NO 39
<211> LENGTH: 1647
<212> TYPE: DNA
<213> ORGANISM: Streptomyces murinus

<400> SEQUENCE: 39
gcggccgccg ttcgtgctca gtggtgcccg tggttccccg cgagccggtg caggaccgcc      60
cccgccatgg cctcctcgcc ccgggcgttg gggtgcgccg gggccgcggg cgcggccggc     120
tggagcggct cgatccagcg gtccgcgggc gccttgcaca tgtcgtggcc cacggtcgga     180
ccgtatgtgt ccacgtactc ggcgcggttg cgcccggcca ccgtgcgcag catcaggttc     240
agccgcttct cggtgtcccg cagataggcg aagtcgccct gtgcgaaggg gacctgcggg     300
```

-continued

```
aagcagccca ccccgtcgtc gggcagcaga tcggggtagc cgacgaccac gacccgggcg    360
tgcggcgccc gcgcgtgcac ggcccgcagc acctcggtga ccttcggcgc ggtccgccgt    420
accgcgagcg ccagcgcgtc ctgcccggac gcctcgtagg agcgctcgca gggactgccc    480
gtcgggtcct ggacaccgag ccgggcgcag gtggcgatga tggtgccgaa cccgacgtcg    540
ttgccgccta tttggagcgt caccaggtcc gtgttccgtg aaacggcgtc cagctggggc    600
ccgttggtgc cctgggcctg ccacatctgc acggtcgtcg cgcccgagca gctgacgtcg    660
gtgaacgtcg tcgccctcgc ccgccgcgcc accagcgacg ggtaattccg gtcggagcgg    720
gcgcagtcgg catccacctg ggtgggtatg cccgggcccg aggtgtagga gtcgccgagc    780
gccacgtagt ccaggcggtg gccgcggccc gccggatgcg cggcggccgg agtggtggcg    840
gcggcgacca gggcgcagcc gcccaccacc gccgccagga ccgccgcccg ccgccgggct    900
ctcgccccgt ccgccggacg cctgtcgttc gtcatggttc cccctgggga ccggtacacg    960
gcgcggacgg cgccgccctg gagcggccct cacgcgatcg actgggtctg tataccgtcc   1020
ggtaggtccc gccgaccaga agcgcgagcc catgagttcg ggggagaacg cggcggggag   1080
ccgccggcgg ggcgcggtgc cggcggcggt gcgcgacccc gcgccccggc ctcaggcgcc   1140
ggacgcggcg acggccggcg cgggctcctg gagcagcgag tcgtcctccg gccgggcccc   1200
ggacagccgg tggcgtgccg cgatcagggc catgtcgaca tcccgcgtcc ggtggccac   1260 gcacagcgtg tacgagatgt ccgcgagccg ctgctgcgcc ctcggggtgc tctcctcggc   1320
gccgagcagc gcgagggtct cgtactgggt gatgaggtcc ttcagcacgg cggggtgtgc   1380
catcagcatg gggtcggcct cctggtgtct cgccgatcta cgacgtcaca ggcgcgacta   1440
cccggggccg cgccccgcat gccacccccgg tggtccccgg tcccgcgcgc accgcccttt   1500
ccggacagga agacggacac gtcacccgca cgggtgctct ccggccggta tgcgccggtc   1560
gggcccccgt cgccgccctc cgtcgctgat catgcacctg tgagtctgca cacccgaagt   1620
gccgtaccgc gccgggtcgt tccggcc                                      1647
```

<210> SEQ ID NO 40
<211> LENGTH: 1560
<212> TYPE: DNA
<213> ORGANISM: Streptomyces murinus

<400> SEQUENCE: 40

```
gtgctcggca ccctcagtgt cctgtccctg ctgtccgccc tgcccgccgc cgcgcagccc     60
gcgcgtgccg cggcccggcc cgccgcgccg ccgcccggc aggccacggc cgccgaggcg    120
cggaccgacg cctacctccg ctcggtcaag gaccggcccg cggccctgcg ggccttcttc    180
cggcagctcc ccaagggcgg ggacctgcac aaccacctct ccggagcggt gaacacggac    240
tacctcatcg agctggccgc cgaggacggc ctgtgcatcg acgcgacgat gaccgccgtc    300
ccctcgccct gcggccccgg cacgcgcccc gccgccgacg cccgcaccga ccgcgccttc    360
cacgacgcga tcgtgcgcgc ctggtccatg caggacttcc cgcccgacga gaacgggcac    420
gaccacttct tcgacacctt cggcaagttc ggcgaggtca cctggcggca ccggggcaag    480 ctgtcgcgc aggtcgccga caccgtcgtc gccaacaacc agtcgtacct ggagacgatg    540 gtcaccccg cctccgacgg cgccaagcaa tcgccgacc aggtgggctg ggacgccgat    600
ctgaccgccc tgcaccgcaa gctgccgcg ggcggcaagc tggacaagct ggtcgcggac    660 gccccgcaagg aggccgacga cggcgacgcc gagttccgcg ccaccgagca ctgcggcacc    720
```

-continued

```
gcgaaggccc ggcccgcctg cgggctcacg gtccgctgga tctcccaggc gtcccggggc      780
agttcaccgg tgcgggtctt cacccagctg gacctcggca tgcggctcgc cgaggcggac      840
tcccgcttcg tcgccgtcaa cctggtgcag ccggaggact gggacagctc gctggagaac      900
tacagcctcc agatgcgcat ggtcggctat ctgcgcaccg tgtacccgaa ggcccatgtc      960
accctgcacg cgggcgagtt gtggcccgga ctggtcaagc ccgaggcgct gaagttccat     1020
atcgccgagg cggtggacat cgcgcacacc cagcgcgtcg gacacggtgt cgacctcgtc     1080
cacgaggaca actggcagcg caccgcccgc accatggcgg cccggcagat cgccgtcgag     1140
gtgcccttct ccagcaacgc ccagatcctc ggcgtcaagg gtgccgagca ccccttcacg     1200
acgtaccgcc gctacggcgt cccggtcgtc ctcgccaccg acgacccggt tgtctcgcgc     1260
atcgacatca gccacgagta ccagtacgcc gccgccacct acggcctcgg ctacccggag     1320
ctgaaggacc tggcccgcgc ctccctccag tacgccttcc tgcccggcgc gagcctgtgg     1380
cagggcaacc ccaccgccca gggctaccac ccggtcgcgg cctgccgcgc cgagcgcccc     1440
ggacagcccg tgcacagcgc ggcctgccgt cggctcctcg acggcagcgc ccgggcgcgc     1500
ctggagtggc gccaggaggc cgcgttcgcg gcgttcgagc gggcgcacgc ccgggggtga     1560
```

<210> SEQ ID NO 41
<211> LENGTH: 615
<212> TYPE: DNA
<213> ORGANISM: Streptomyces murinus

<400> SEQUENCE: 41

```
cccggttccg gccgcggccg tgcggacggc cgcggccgga atgcatcgat tggccgagaa       60
gtacgaggtc atacaaccgg atgacccgat tccgtgcggg agcgcgggtc gggtcttcgc      120
cattacccgg gctttgcgac gacgtttccg gtaacccccac gcaccccgt cgtcacggcc      180
cgtaccgtgc agggatgcct ctcccttaag atcatcacat cgtcatcaca tagccttcac      240
ggaacgacca ctttcggccg atcgcgttcc gggtcctcgt gacggggcag acgcggtacg      300
cgccccgcgc ctagcctccc gggccatgcg atcacctctg ctgagacgcc tcggtctcac      360
cgccgtcctc gccgtcgtcc tcgccgtctt cggcttcagc accatcgcca gcgcggaccc      420
ggacccggcc gccctcacct tcagcaccga cagcgccacc accaccccg gtggttcggt       480
caagctgtcg atgacgctga ccaacaacaa gacgtacgac gtcctgttcg tgtaccagac      540
gatcgatccg acctggctga ccacccagcg tccggacctg aagtacagct tcgccggctg      600
caccctggcg gccgc                                                       615
```

AMP DEAMINASE ORIGINATING STREPTOMYCES AND UTILIZATION THEREOF

CROSS-REFERENCE TO RELATED APPLICATIONS

This application is a national phase application filed under 35 U.S.C. §371 from PCT Application No. PCT/JP2005/007892, filed Apr. 26, 2005, which claims priority to Japanese Patent Application No. JP 2004-134464, filed Apr. 28, 2004, the contents of which are incorporated herein by reference.

TECHNICAL FIELD

The present invention relates to AMP deaminase. More particularly, the present invention relates to AMP deaminase derived from a microorganism.

BACKGROUND ART

AMP deaminase is also called adenyl deaminase, AMP aminohydrolase, and the like, and catalyzes a reaction of allowing adenylic acid to hydrolytically deaminate to generate inosinic acid and ammonia. It has been reported that AMP deaminase has been widely found in living animal tissues and separated from various tissues from various species to date (Fujishima T. and Yoshino H., Amino Acid-Nucleic Acid, Vol. 16, pp 45-55 (1967): non-patent document 1, Magdale'na Rosinova' et al., Collection Czechoslov. Chem. Commun. Vol. 43, pp 2324-2329 (1978): non-patent document 2, Japanese Patent Unexamined Publication No. S55-120788: patent document 1). Meanwhile, mainly from the viewpoint of industrial utilization, search for AMP deaminases derived from microorganism has been extensively carried out. Particularly, many studies have been done on AMP deaminase derived from filamentous bacterium. Some AMP deaminases, for example, AMP deaminase derived from *Aspergillus melleus* have been attempted to be industrially used aiming at increasing taste in production of yeast extract.

Patent document 1: Japanese Patent Unexamined Publication No. S55-120788
Non-patent document 1: Fujishima T. and Yoshino H., Amino Acid-Nucleic Acid, Vol. 16, pp 45-55 (1967)
Non-patent document 2: Magdale'na Rosinova' et al., Collection Czechoslov. Chem. Commun. Vol. 43, pp 2324-2329 (1978)

DISCLOSURE OF INVENTION

Problems to be Solved by the Invention

At present, in the production of yeast extract, in order to increase taste, nuclease and AMP deaminase are generally used. In general, the optimum temperature of nuclease is about 65° C. On the other hand, the optimum temperature of a currently used AMP deaminase from *Aspergillus melleus* is about 50° C. Therefore, in production, it is impossible to allow two enzymes to act simultaneously at high temperature. Treatment with nuclease and treatment with AMP deaminase had to be carried out separately. If AMP deaminase has an excellent thermal resistance property, it can be allowed to act together with nuclease. Thus, production process can be shortened. Furthermore, since treatment with these two enzymes can be carried out at high temperatures, it is not necessary to once reduce the treatment temperature to about 50° C. that is a reaction temperature of AMP deaminase. Thus, it is possible to prevent contamination effectively. Thus, in the industrial utilization, a thermal resistant AMP deaminase has many advantageous and it has been demanded to be found.

Means to Solve the Problems

Under the above-mentioned circumferences, the present inventors have carried out a screening for searching microorganisms for a novel AMP deaminase. As a result, the present inventors have found that *Streptomyces* of the genus *Streptomyces* produces AMP deaminase having a high thermostability. Furthermore, they have obtained the findings that AMP deaminase produced by *Streptomyces murinus* has an excellent thermostability.

After the present inventors obtained the above-mentioned findings, they attempted to identify the enzyme (AMP deaminase derived from *Streptomyces murinus*). As a result, as shown below, they succeeded in identifying the enzyme and clarified the amino acid sequence and nucleotide sequence thereof, which has enabled the production of the enzyme as a recombinant protein. Furthermore, the use of a technique such as gene recombination has enabled the productivity of the enzyme to be enhanced and the enzyme itself to be improved.

The present invention was made based on the above-mentioned findings, and provides the following configurations.

[1] AMP deaminase comprising the following characteristics:

(1) catalyzing a reaction: 5'-adenylic acid+$H_2O \to$ 5'-inosinic acid+$NH_3$;

(2) being stable at a temperature of 65° C. or less (in an acetate buffer solution (pH 5.6));

(3) having a molecular weight of 48,000±2,000 in gel filtration and 60,000±3,000 in SDS-PAGE; and (4) having an optimum pH of around 5.6 (in a McIlvaine buffer solution).

[2] AMP deaminase derived from *Streptomyces*, comprising the following characteristics:

(1) catalyzing a reaction: 5'-adenylic acid+$H_2O \to$ 5'-inosinic acid+$NH_3$; and (2) being stable at a temperature of 65° C. or less (in an acetate buffer solution (pH 5.6)).

[3] The AMP deaminase described in [2], wherein the *Streptomyces* belongs to the genus *Streptomyces*.

[4] The AMP deaminase described in [2], wherein the *Streptomyces* is selected from the group consisting of *Streptomyces murinus*, *Streptomyces celluloflavus*, and *Streptomyces griseus*.

[5] A method of producing yeast extract, the method comprising a step of allowing the AMP deaminase described in any one of [1] to [4] to act.

[6] A method of producing a taste substance by allowing the AMP deaminase described in any one of [1] to [4] to act on 5'-nucleotide so as to deaminate the 5'-nucleotide.

[7] A method of producing AMP deaminase, the method comprising:

culturing *Streptomyces* of the genus *Streptomyces* in a nutrient medium so as to produce the AMP deaminase described in [1]; and collecting the produced AMP deaminase.

[8] The method described in [7], wherein the *Streptomyces* is selected from the group consisting of *Streptomyces murinus*, *Streptomyces celluloflavus*, and *Streptomyces griseus*.

[9] An isolated AMP deaminase consisting of the following (a) or (b):

(a) a protein having an amino acid sequence set forth in SEQ ID NO: 1;

(b) a protein having an amino acid sequence obtained by modifying a part of the amino acid sequence set forth in SEQ ID NO: 1, and functioning as AMP deaminase.

[10] An isolated nucleic acid molecule encoding the AMP deaminase described in [9].

[11] The isolated nucleic acid molecule described in [10], having any one of the following nucleotide sequences (a) to (c):

(a) a nucleotide sequences of any one of SEQ ID NOs: 3 to 5;

(b) a nucleotide sequence obtained by modifying a part of the nucleotide sequence described in (a), and encoding a protein functioning as AMP deaminase; and (c) a nucleotide sequence hybridizing a nucleotide sequence complementary to the nucleotide sequence described in (a) or (b) under stringent conditions, and encoding a protein functioning as AMP deaminase.

[12] A vector carrying the nucleic acid molecule described in any one of [9] to [11].

[13] A transformant in which the nucleic acid molecule described in any one of [9] to [11] is introduced.

[14] A method of producing AMP deaminase, the method comprising the following steps (1) and (2):

(1) culturing the transformant described in [13] in a condition capable of producing a protein encoded by the nucleic acid molecule; and (2) collecting the produced protein.

EFFECT OF THE INVENTION

AMP deaminase of the present invention has excellent thermostability and can act at relatively high temperatures. Therefore, the enzyme reaction can be carried out in the conditions free from contamination. Furthermore, AMP deaminase of the present invention can be acted simultaneously with other enzymes acting at high temperature, for example, nuclease used in the production of yeast extract, and therefore simplification and shortening of the production process can be achieved.

BRIEF DESCRIPTION OF THE DRAWINGS

FIG. 2 is a table showing the comparison of phosphatase activity/deaminase activity (P/D) of AMP deaminases produced by *Aspergillus melleus* and *Streptomyces murinus*.

FIG. 4 (*a*) shows the measurement results in the case where the nuclease treatment and the deaminase treatment are carried out separately as in the present production process. FIG. 4 (*b*) shows the measurement results in the case where the nuclease treatment and the deaminase treatment are carried out simultaneously.

FIG. 5 (*a*) shows a chromatography result by HiPrep™ 16/10 ButylFF, and FIG. 5 (*b*) shows a chromatography result by Superose 12.

FIG. 6 (*b*) shows results of analysis of purified enzyme by SDS-PAGE (CBB staining). Lane I shows bands of protein molecular weight marker. Bands of phosphorylase b (M.W. 97,400), bovine serum albumin (M.W. 66,267), aldolase (M.W. 42,400), carbonic anhydrase (M.W. 30,000), trypsin inhibitor (M.W. 20,100), lysozyme (M.W. 14,400) are shown sequentially from the side of high molecular weight.

FIG. 7 (*a*) shows the relative activity (%) when the activity value in the reaction at 65° C. is defined as 100%. FIG. 7 (*b*) is a graph showing the thermostability of AMP deaminase derived from *Streptomyces murinus*.

FIG. 8 (*a*) shows the relative activity when the activity value in the reaction in pH 5.6 is defined as 100%. FIG. 8 (*b*) is a graph showing the pH stability of AMP deaminase derived from *Streptomyces murinus*.

FIG. 9 is a graph summarizing substrate specificities of AMP deaminase derived from *Streptomyces murinus*. FIG. 9 shows relative activities when the enzyme activity with respect to AMP is defined as 100%.

FIG. 11 is a graph summarizing characteristics of AMP deaminase derived from *Streptomyces murinus*. For comparison, optimum pH, etc. of nuclease derived from *Penicillium citrinum* and AMP deaminase derived from *Aspergillus meleus* are shown.

FIG. 12 is a table showing the comparison of thermostability and substrate specificity of AMP deaminase produced by *Streptomyces griseus* subsp. *griseus*, *Streptomyces griseus*, and *Streptomyces celluloflavus*.

FIG. 13 shows analysis results of the N-terminus amino acid sequence and the internal amino acid sequence of AMP deaminase derived from *Streptomyces murinus* as follows: N-terminus-A P P E E Q A T D A E E R T D-C-terminus (SEQ ID NO:27); TD DAGYL (SEQ ID NO: 28); N-terminus-E A D D G D A E F R-C-terminus (SEQ ID NO: 29); and F G B V T A R H R G-C-terminus (SEQ ID NO: 30).

FIG. 17 is a table showing the measurement result of activity of AMP deaminase produced by transformant SAD-1 into which an AMP deaminase gene is introduced. ND denotes "not detected".

FIG. 19 is a table summarizing substrate specificities of AMP deaminase derived from transformant (SAD-1). FIG. 19 shows relative activities when the enzyme activity with respect to AMP is defined as 100%.

FIG. 21 shows SEQ ID NO: 32 an amino acid sequence or AMP deaminase derived from *Streptomyces* which has been successfully identified and SEQ ID NO: 31 a sequence (including a promoter region and a terminator region) coding therefor.

FIG. 22 is a continuation of FIG. 21 with the nucleotide sequence being SEQ ID NO: 33 and the amino acid sequence being SEQ ID NO: 34.

FIG. 23 shows SEQ ID NO: 35 an amino acid sequence (without including signal peptide) of AMP deaminase derived from *Streptomyces* which has been successfully identified.

FIG. 24 shows SEQ ID NO: 36 an amino acid sequence (including signal peptide) of AMP deaminase derived from *Streptomyces* which has been successfully identified.

FIG. 25 shows SEQ ID NO: 37 a sequence (including a promoter region and a terminator region) encoding AMP deaminase derived from *Streptomyces* which has been successfully identified.

FIG. 26 shows the continuation of FIG. 25 as SEQ ID NO: 38.

FIG. 27 shows SEQ ID NO: 39 a sequence of a promoter region of a gene encoding AMP deaminase derived from *Streptomyces* which has been successfully identified.

FIG. 28 shows SEQ ID NO: 40 a sequence of a structural gene of AMP deaminase derived from *Streptomyces* which has been successfully identified.

FIG. 29 shows SEQ ID NO: 41 a sequence of a terminator region of a gene encoding AMP deaminase derived from *Streptomyces* which has been successfully identified.

BEST MODE FOR CARRYING OUT THE INVENTION

Figure 1:
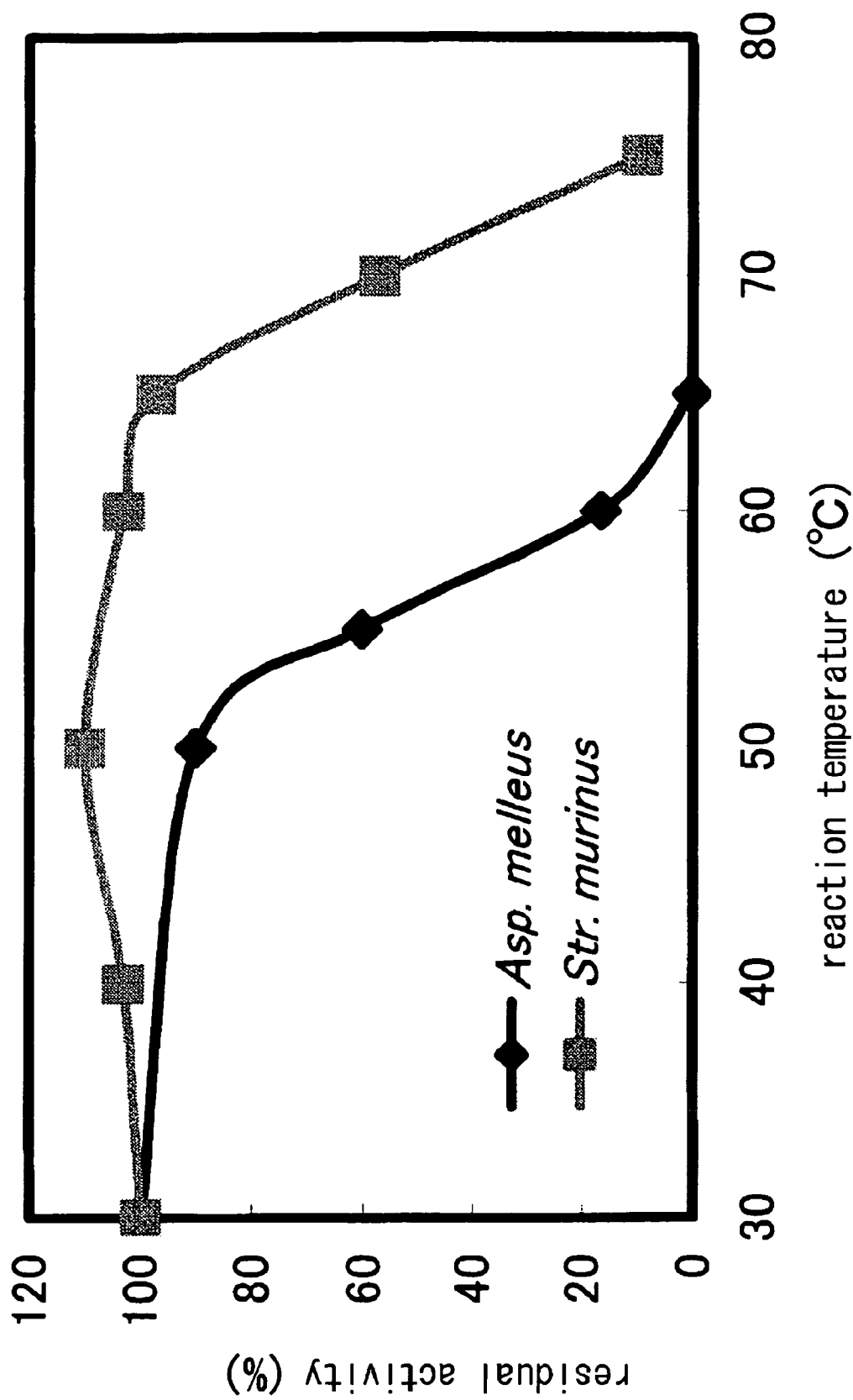
FIG. 1 is a graph showing the comparison of thermostabilities of AMP deaminase produced by *Aspergillus melleus* and *Streptomyces murinus*. In this graph, the abscissa represents a reaction temperature and the ordinate represents the residual deaminase activity (%).

The first aspect of the present invention relates to AMP deaminase. AMP deaminase of the present invention is derived from *Streptomyces*. The origin of AMP deaminase of the present invention is not limited to a particular species of *Streptomyces*. The present inventors have investigated and found that AMP deaminase produced by *Streptomyces murinus*, *Streptomyces celluloflavus* and *Streptomyces griseus* also has a high thermal resistant property.

AMP deaminase of the present invention catalyzes the following reaction: 5'-adenylic acid+$H_2O$→5'-inosinic acid+$NH_3$ (characteristic (1)). Thus, AMP deaminase of the present invention acts on 5'-adenylic acid (AMP). As shown in the below-mentioned Examples, AMP deaminase derived from *Streptomyces murinus* that is one embodiment of the present invention acts on 5'-dAMP (5'-deoxy adenylic acid), ADP (adenosine 5'-diphosphate) and ATP (adenosine 5'-triphosphate) favorably. Therefore, AMP deaminase of the present invention can be applied to not only a reaction using AMP as a substrate but also a reaction using 5'-dAMP, ADP and ATP as a substrate.

Meanwhile, AMP deaminase of the present invention is excellent in thermostability and stable at 65° C. or less (characteristic (2)). Herein, "stable at 65° C. or less" means that when an enzyme solution adjusted to pH 5.6 with an acetate buffer solution is treated at 65° C. for 30 minutes, 5% or more, preferably 10% or more, further preferably 30% or more, more further preferably 50% or more and the most preferably 90% or more of activity remains based on the reference (100%) in the case where the treatment is not carried out (the same treatment is carried out at temperatures of 65° C. or less, the residual activity is generally increased). Since excellent thermostability is provided, AMP deaminase of the present invention can act favorably at high temperatures (for example, 60° C., 65° C., and 70° C.).

As shown in the below-mentioned Examples, the present inventors have found an enzyme produced by *Streptomyces murinus* as one of AMP deaminases having the above-mentioned characteristics and have succeeded in purifying this enzyme. When the obtained AMP deaminase was investigated in detail, it was revealed that AMP deaminase has the following characteristics.

(3) The molecular weight by gel filtration is 48,000±2,000. Note here that the molecular weight by SDS-PAGE is 60,000±3,000.

(4) The optimum pH is around 5.6 (in McIlvaine buffer solution).

(5) The working pH is about 4.5 to about 8.5 (in McIlvaine buffer solution).

(6) The stable pH is about 6.0 to about 8.5 (in McIlvaine buffer solution).

(7) The reaction temperature is about 40° C. to 70° C. (in acetate buffer solution (pH 5.6)).

(8) The optimum temperature is around 65° C. (in acetate buffer solution (pH 5.6)).

(9) The temperature stability is stable at 65° C. or less (in acetate buffer solution (pH 5.6).

The range of the working pH is in the range in which the relative activity is about 50% or more when the AMP deaminase activity at the optimum pH is defined as reference (100%). Meanwhile, the range of the stable pH is in the range in which the residual activity is about 50% or more when the AMP deaminase activity at the optimum pH is defined as reference (100%).

As to the thermostability, when an enzyme solution that is adjusted to pH 5.6 with an acetate buffer solution is treated at 65° C. for 30 minutes, about 90% of residual activity is found with respect to a reference (100%) that is the enzyme activity when no treatment was carried out. When the treatment temperature was raised to 70° C., about 55% of activity was maintained.

Furthermore, the range of the reaction temperature is a range in which the relative activity is about 70% or more when the AMP deaminase activity at the optimum temperature is defined as reference (100%).

Meanwhile, when the substrate specificity was investigated, it was revealed that AMP deaminase derived from *Streptomyces murinus* acted on 3'-AMP, 5'-dAMP, ADP, ATP, Adenosine, and cAMP (cyclic adenosine-3',5'-monophosphate) and that it did not act on 2'-AMP, adenine, 5'-GMP, 5'-UMP, and 5'-CMP. In particular, it was found that AMP deaminase acted on 5'-dAMP, ADP, and ATP favorably. The action on adenosine was weak, which was about 1/10 or less of the action on 5'-AMP.

Furthermore, a phosphatase activity was not detected. On the contrary, in conventional AMP deaminase derived from *Aspergillus melleus*, a contaminated phosphatase activity is detected. Thus, AMP deaminase derived from *Streptomyces murinus* is significantly different from conventional AMP deaminase in that the contaminated phosphatase activity is extremely small.

When phosphatase is contaminated, inosinic acid that is a taste component produced by AMP deaminase effect by 5'-AMP is further decomposed into inosine. As a result, a taste property is lost, so that AMP deaminase derived from *Streptomyces murinus* into which extremely little phosphatase is contaminated is industrially advantageous.

After all, AMP deaminase derived from *Streptomyces murinus* has the above-mentioned characteristics (3) to (8), thermostability, substrate specificity, and extremely small amount of contaminated phosphatase.

Note here that the AMP deaminase activity in various tests such as a thermostability test is measured based on methods described in the below-mentioned Examples.

The second aspect of the present invention relates to a production method (preparation method) of AMP deaminase and the method includes the following steps:

(a) culturing step of culturing *Streptomyces* of the genus *Streptomyces*.

(b) purification step of purifying AMP deaminase from a culture solution after the culturing step.

The kinds of *Streptomyces* used in the step (a) is not particularly limited as long as it is expected to produce AMP deaminase having excellent thermostability. For example, *Streptomyces murinus*, *Streptomyces celluloflavus*, or *Streptomyces griseus* can be used. *Streptomyces* can be cultured by a routine method. As a medium, a medium containing a carbon source such as glucose, sucrose, gentiobiose, soluble starch, glycerin, dextrin, syrup, organic acids, and the like, nitrogen source such as ammonium sulfate, ammonium carbonate, ammonium phosphate, ammonium acetate, or peptone, yeast extract, corn steep liquor, casein hydrolysate, bran, meat extract, and the like, and if necessary, inorganic chlorine (inorganic ion) such as potassium salt, magnesium salt, sodium salt, phosphate salt, manganese salt, iron salt, zinc salt, and the like, can be used. In order to promote the growth of *Streptomyces*, a medium to which vitamin, amino acid, and the like, have been added can be used. The pH of the medium is adjusted to, for example, in the range from 5.0 to 8.0, and preferably, in the range from 5.5 to 7.5. The culturing temperature is, for example, in the range from 15° C. to 50° C., preferably in the range from 20° C. to 40° C., and more preferably in the range from 25° C. to 35° C. The culturing time is not particularly limited and may be, for example, one day or more, three days or more, and five days or more. As a culturing method, for example, a shake culture method, and an aerobic submerged culture method with a jar fermenter can be employed.

The above-mentioned various culturing conditions may be changed appropriately depending upon the subjects to be cultured and the conditions are not particularly limited as long as AMP deaminase of the present invention can be produced.

From a culture solution or fungus body obtained after *Streptomyces* is cultured for a desired time, AMP deaminase can be collected. When AMP deaminase is collected from a culture solution, for example, a culture supernatant is subjected to filtration and centrifugation so as to remove insoluble matters, followed by isolation and purification by combining salting out such as ammonium sulfate precipitation, dialysis and various chromatography, and the like. Thereby, AMP deaminase can be obtained. Preferably, after fraction by salting out such as ammonium sulfate precipitation, hydrophobic chromatography and gel filtration are carried out.

On the other hand, when AMP deaminase is collected from a fungus body, for example, after the fungus body is crushed by pressurizing treatment, ultrasonic treatment, and the like, isolation and purification are carried out as mentioned above. Thereby, AMP deaminase can be obtained. Note here that the above-mentioned series of processes (crushing of fungus bodies, isolation, and purification) may be carried out after fungus bodies are collected from a culture solution in advance by filtration, centrifugation, and the like.

In each purification process, in principle, fraction is carried out by using an AMP deaminase activity as an index and then the following step is carried out.

The third aspect of the present invention relates to use of the above-mentioned AMP deaminase of the present invention. AMP deaminase of the present invention is used for various applications similar to conventional AMP deaminases (that is to say, AMP deaminase derived from *Aspergillus melleus*, which has been used to date). However, from the characteristic of having excellent thermal resistant property, AMP deaminase of the present invention can be suitably used in applications in which a reaction at a high temperature is preferred. Herein, "applications in which a reaction at a high temperature is preferred" means an application in which AMP deaminase is subjected to reaction at a high temperature from the viewpoint of production efficiency, contamination, and the like. A specific example of this application can include production of yeast extract. In the production of yeast extract, in general, taste is increased (taste is improved) by nuclease treatment and AMP deaminase treatment. When AMP deaminase of the present invention having excellent thermostability is used, AMP deaminase treatment can be carried out simultaneously with nuclease treatment that is carried out at a high temperature. This can simplify and shorten the production process and at the same time, can effectively prevent the contamination during the treatment of enzyme.

In the production method of yeast extract using AMP deaminase of the present invention, as a preferable embodiment, the next step, that is, a step of adding nuclease and AMP deaminase to yeast lysate and allowing them to act on yeast lysate at a high temperature is carried out. The yeast lysate can be prepared by a conventional method. For example, a suspension (pH 7.0) of 10% beer yeast, baker's yeast, or the like, is thermally treated and then commercially available lytic enzyme such as YL-NL "AMANO," YL-15, or the like (both are products of Amano Enzyme Inc.) is added and lysed, so that yeast lysate is prepared. Nuclease is commercially available from various manufacturers (for example, Amano Enzyme Inc.) and suitable nuclease can be selected appropriately. Nuclease prepared by a conventional method from a microorganism may be used. Plural kinds of nucleases may be used combination. The addition amount of nuclease and AMP deaminase can be appropriately set taken the kinds or activity values of enzymes to be used into consideration. The working temperature is a temperature at which both nuclease and AMP deaminase can work. They are allowed to react at, for example, in the range from 60° C. to 80° C., preferably in the range from 65° C. to 75° C., and further more preferably 70° C.

(Isolated AMP Deaminase)

As shown in the below-mentioned Examples, the present inventors succeeded in identifying an amino acid sequence of AMP deaminase derived from *Streptomyces murinus* and a sequence of genes coding therefor. This makes it possible to produce AMP deaminase as a recombinant protein.

The further aspect of the present invention relates to an isolated AMP deaminase based on the above-mentioned achievement. AMP deaminase of the present invention includes, for example, a protein having an amino acid sequence set forth in SEQ ID NO: 1. As shown in the below-mentioned Examples, it is confirmed that the protein actually exhibits the AMP deaminase activity. Note here that a sequence including a signal peptide is shown in SEQ ID NO: 2.

One embodiment of the present invention provides AMP deaminase consisting of a protein having the same function as the protein having an amino acid sequence set forth in SEQ ID NO: 1 or 2 but having a difference in a part of the amino acid sequence (hereinafter, also referred to as "homologous protein"). The phrase "having a difference in a part of the amino acid sequence" typically means that the amino acid sequence includes mutation (change) in the amino acid sequence due to deletion, substitution of one to several of the amino acids constituting the amino acid sequence, or addition and insertion of one to several amino acids, or combination thereof. Herein, the difference in the amino acid sequence is acceptable as long as the function of catalyzing AMP deaminase, that is, a reaction: 5'-adenylic acid+$H_2O$→5'-inosinic acid+ $NH_3$ (also referred to as "AMP deaminase activity") is maintained. As long as this condition is satisfied, a position of difference in the amino acid sequence is not particularly limited and also may include differences in a plurality of positions. The plurality herein denotes a number corresponding to, for example, about less than about 30%, preferably less than about 20%, further preferably less than about 10%, further more preferably less than 5%, and most preferably less than about 1% with respect to total amino acids. That is to say, a homologous protein has the identity of about 70% or more, preferably about 80% or more, further preferably about 90% or more, further more preferably about 95% or more, and most preferably about 99% or more with respect to the amino acid sequence set forth in SEQ ID NO: 1 or 2.

Preferably, a homologous protein is obtained by allowing a conservative amino acid substitution to be generated in a nonessential amino acid residue (amino acid residue that is not related to "AMP deaminase activity"). Herein, a "conservative amino acid substitution" is one in which the amino acid residue is replaced with an amino acid residue having a side chain with similar feature. The amino acid residues are divided into some families including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Preferably, the conservative amino acid substitution is a substitution between preferably an amino acid residue of the same family.

The identity (%) of two amino acid sequences or of two nucleic acid sequences (hereinafter, referred to as "two sequences" as a term including these sequences) can be determined by, for example, the following procedures. Firstly, the two sequences are aligned so that two optimum comparison between two sequences can be conducted (e.g., gaps may be introduced in a first sequence for optimum alignment with second sequence). When the molecule (amino acid residue or nucleotide) at the certain position of the first sequence is the same as the molecule at corresponding position of the second sequence, then the molecules are identical at that position. The identity between the two sequences is a function of the number of identical positions shared by the sequences (i.e. identity (%)=number of identical positions/total number of positions×100). Preferably, the number of gaps, and the length of each gap, which need to be introduced for optimum alignment of the two sequences are considered.

The comparison of two sequences and determination of percent identity between two sequences can be accomplished using a mathematical algorithm. A specific example of the mathematical algorithm that can be used for comparison between sequences includes a mathematical algorithm that is described in Karlin and Altschul (1990) Proc. Natl. Acad. Sci. USA 87:2264-68 and that was modified by Karlin and Altschul (1993) Proc. Natl. Acad. Sci. USA 90:5873-77. However, the mathematical algorithm is not particularly limited to this. Such an algorithm is incorporated into NBLAST program and XBLAST program (version 2.0). In order to obtain a nucleotide sequence being homologous to the nucleic acid of the present invention, for example, with NBLAST program, BLAST nucleotide search is carried out with score=100 and wordlength=12. In order to obtain an amino acid sequence being homologous to the protein of the present invention, for example, with XBLAST program, BLAST-polypeptide search is carried out with score=50 and wordlength=3. In order to obtain a gap alignment for comparison, Gapped BLAST described in Altschul et al. (1997) Amino Acids Research 25 (17): 3389-3402 can be used. In the case where BLAST and Gapped BLAST are used, default parameter of the corresponding program (for example, XBLAST and NBLAST) can be used. Another example of a mathematical algorithm that can be used for comparison of sequence includes an algorithm described in Myers and Miller (1988) Comput Appl Biosci. 4:11-17. Such an algorithm is incorporated into an ALIGN program that can be used in, for example, a GENESTREAM network server (IGH Montpellier, France) or an ISREC server. In the case where the ALIGN program is used for comparison of the amino acid sequence, for example, PAM120 residue mass table is used, and gap length penalty can be made to be 12 and gap penalty can be made to be 4.

The identity between two amino acid sequences can be determined using the GAP program in the GCG software package using either a Blossum 62 matrix or a PAM250 matrix with the gap weight of 12, 10, 8, 6, or 4 and the length weight of 2, 3, or 4. Furthermore, the homology between two nucleic acid sequences can be determined using the GAP program in the GCG software package with a gap weight of 50 and a length weight of 3.

In AMP deaminases of the present invention (including homologous protein), AMP deaminase of natural *Streptomyces* can be prepared from the *Streptomyces* by the operations such as extraction, purification, and the like. Furthermore, by using a genetic engineering technique based on this specification and sequence information disclosed in an attached sequence list, AMP deaminase of the present invention (including homologous protein) can be prepared. For example, AMP deaminase of the present invention can be prepared by transforming an appropriate host cell by DNA encoding AMP deaminase and collecting protein expressed by the transformant. The collected protein can be appropriately purified in accordance with the purpose. In the case where AMP deaminase is prepared as recombinant protein, various modifications can be carried out. For example, DNA encoding AMP deaminase of the present invention and other appropriate DNA are inserted into the same vector and the vector is used for producing recombinant protein. Then, a recombinant protein in which other peptide or protein is linked to AMP deaminase of the present invention can be obtained. Furthermore, modification such as addition of sugar chain and/or lipid or processing of N-terminus or C-terminus may be carried out. The above-mentioned modification enables extraction of recombinant protein, simplification of purification, addition of biological functions, or the like.

Herein, "isolated" used with respect to AMP deaminase of the present invention denotes that AMP deaminase exists in a state in which they are taken out from its original environment (for example, natural environment when AMP deaminase is a natural material), that is, in a state in which they are different form from the original form.

Isolated AMP deaminase generally does not contain a fungus body component of a producing strain. Furthermore, it is preferable that the content of the contaminated components (contaminated protein, other components derived from the host when it is produced by a recombination DNA technology, component of a culture solution, and the like) is small. The amount of the contaminated protein in the isolated AMP deaminase of the present invention is, for example 50% or less, preferably 40% or less, further preferably 30% or less, and more preferably 20% or less of the total amount of the protein.

(Nucleic Acid Molecule Encoding AMP Deaminase)

The further aspect of the present invention relates to a nucleic acid molecule encoding AMP deaminase.

The term "nucleic acid" in the present invention includes DNA (including cDNA and genome DNA), RNA (including mRNA), DNA analogs and RNA analogs. The form of the nucleic acid of the present invention is not particularly limited. That is to say, the nucleic acid may be any of a single strand and a double strand. However, a double-stranded DNA is preferable. The degeneration of codon is also taken into consideration. That is to say, the nucleic acid may have any nucleotide sequences as long as the target protein can be obtained as an expressed product.

The term "nucleic acid encoding a specific protein" denotes nucleic acid from which the protein is obtained when it is expressed. It includes not only nucleic acid having a nucleotide sequence corresponding to an amino acid sequence of the protein but also nucleic acid to which a sequence that does not encode an nucleic acid is added to the above-mentioned nucleic acid (for example, DNA containing one or a plurality of introns).

The term "isolated nucleic acid molecule" in this specification includes nucleic acid molecules that are separated from other nucleic acid molecules coexisting in a natural state of the nucleic acid. However, a part of other nucleic acid components such as a nucleic acid sequence neighboring in the natural state may be contained.

In the case of nucleic acid produced by genetic recombination technology, for example, cDNA molecule, the "isolated nucleic acid" denotes nucleic acid in a state in which cell components, culture solution, and the like, are not substantially contained. Similarly, in the case of nucleic acid produced by chemical synthesis, the "isolated nucleic acid" denotes nucleic acid in a state in which a precursor such as dNTP or chemical materials used in the synthesis process is not substantially contained.

Whether nucleic acid is present as a part of a vector or a composition, or nucleic acid is present in a cell as a foreign molecule, the nucleic acid is "isolated nucleic acid" as long as it is present as a result of artificial operation.

Unless otherwise noted, when merely the term "nucleic acid" is used in this specification, it signifies that nucleic acid in a state in which it isolated.

The nucleic acid molecule of the present invention encodes above-mentioned AMP deaminase of the present invention. That is to say, the nucleic acid molecule of the present invention encodes a protein having an amino acid sequence set forth in SEQ ID NO: 1 or 2 or the homologous protein thereof. The specific embodiment of the nucleic acid molecule of the present invention is DNA having a nucleotide sequences of SEQ ID NO: 3. This nucleotide sequence is DNA encoding a successfully identified AMP deaminase gene and includes 5' non-translation region (promoter region) and 3' non-translation region (terminator region). Such a DNA includes a original combination (combination in natural state) of promoter, terminator and structural gene. Therefore, when the DNA is used for producing AMP deaminase, excellent gene expression is expected. Therefore, an efficient AMP deaminase production system can be constructed.

Another embodiment of the present invention provides DNA in which any one or more of 5' non-translation region or a part thereof, and 3' non-translation region or a part thereof are deleted from the nucleotide sequences of SEQ ID NO: 3. Specific examples of such DNA can include DNA having a nucleotide sequences of SEQ ID NO: 4 or 5. DNA having the nucleotide sequences of SEQ ID NO: 4 is DNA encoding a structural gene (including a region encoding signal peptide) of successfully identified AMP deaminase. Similarly, DNA having the nucleotide sequences of SEQ ID NO: 5 is DNA encoding a structural gene (which does not include a region encoding signal peptide) of successfully identified AMP deaminase.

The nucleic acid of the present invention can be prepared in an isolated state by standard genetic engineering technique, molecular biological technique, biochemical technique, and the like, with reference to sequence information disclosed in this specification or attached sequence list.

For example, the nucleic acid of the present invention can be isolated from *Streptomyces* genome DNA library by using a hybridization method using all or a part of the nucleotide sequence of the nucleic acid or the complementary sequence thereof as a probe. Furthermore, by using a nucleic acid amplification reaction (for example, PCR) using a synthesized oligonucleotide primer designed to specifically hybridize a part of a nucleotide sequence of the nucleic acid, the nucleic acid of the present invention can be amplified and isolated from *Streptomyces* genome DNA library or *Streptomyces* genome or *Streptomyces* nucleic acid extract. In general, an oligonucleotide primer can be easily synthesized by using, for example, an automated DNA synthesizer.

In accordance with kinds of libraries to be used, a plaque hybridization method, a colony hybridization method, or the like can be used (see, for example, Molecular Cloning, Third Edition, Cold Spring Harbor Laboratory Press, New York). For example, in the case of a library constructed by using, for example, a plasmid, a colony hybridization method is employed. For selection of a clone having the target nucleic acid, a probe having a sequence specific to the nucleic acid of the present invention is used. When the target clone is selected, by carrying out PCR method and the like using a primer specific to the sequence of the target nucleic acid by using a nucleic acid carried by this clone as a template, the nucleic acid of the present invention can be obtained as an amplified product.

The nucleic acid carried by the obtained clone can be subcloned in an appropriate vector for use in use later. Thus, for example, it is possible to construct a recombinant vector for transformation or a plasmid suitable for decoding a nucleotide sequence.

Another embodiment of the present invention provides nucleic acid that has a nucleotide sequence having the same function as the nucleotide sequences of any of SEQ ID NOs: 3 to 5 but having a difference in a part of the nucleotide sequence (hereinafter, referred to as "homologous nucleic acid"). An example of the homologous nucleic acid can include DNA encoding a protein including a nucleotide sequence in which one or a plurality of nucleotides are substituted, deleted, inserted, added or inverted relative to the nucleotide sequences of SEQ ID NOs: 3 to 5 and having an AMP deaminase activity. Such substitution, deletion, or the like, may be occurred in a plurality of sites. The "plurality" herein differs depending upon the position or kinds of amino acid residues in a three-dimensional structure of a protein encoded by the nucleic acid codes, but the "plurality" of nucleotides includes, for example, 2 to 40 nucleotides, preferably 2 to 20 nucleotides and more preferably 2 to 10 nucleotides.

The above-mentioned mutation such as substitution, deletion, insertion, addition or inversion of nucleotide includes a naturally occurring mutation, for example, difference in individual, species, or genus of microorganism carrying an AMP deaminase gene.

Another example of the homologous nucleic acid can include a nucleic acid having difference in nucleotide as mentioned above due to polymorphism represented by SNP.

The above-mentioned homologous nucleic acid can be obtained by, for example, a treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York); random mutagenesis (Molecular Cloning, Third Edition, Chapter 13, Cold Spring Harbor Laboratory Press, New York), and the like. Furthermore, the homologous nucleic acid can be also obtained by the other method such as ultraviolet irradiation. In addition, the homologous nucleic acid can be also obtained by a well-known method using a mutation treatment, for example, treating *Streptomyces* carrying an AMP deaminase gene with ultraviolet ray, followed by isolating the modified gene.

A specific example of a method for preparing the homologous nucleic acid will be described hereinafter. The method includes: extracting a genome (chromosomal) DNA from naturally occurring *Streptomyces* carrying a homologous nucleic acid; treating the extracted DNA with an appropriate restriction enzyme; and then selecting and isolating a DNA that hybridizes under stringent conditions in a screening using the nucleic acid molecule of the present invention (for example, DNA having a sequence of SEQ ID NO: 3) or a part thereof as a probe. In the case where a genome (chromosomal) DNA library including a clone carrying a modified DNA can be used, the DNA can be obtained by screening the library using the nucleic acid molecule of the present invention (for example, DNA having a sequence of SEQ ID NO: 3) or a part thereof as a probe under stringent conditions.

Another embodiment of the present invention relates to a nucleic acid having a nucleotide sequence complementary to the nucleotide sequences of SEQ ID NOs: 3 to 5.

A further embodiment of the present invention provides nucleic acid having a nucleotide sequence at least 60%, 70%, 80%, 90%, 95%, 99% or 99.9% identical to the nucleotide sequences set forth in SEQ ID NOs: 3 to 5 or a nucleotide sequence complementary to any of them. The identity is preferred to be as high as possible.

A further embodiment of the present invention relates to nucleic acid having a nucleotide sequence that hybridizes, under stringent conditions, to the nucleotide sequence complementary to the nucleotide sequences of SEQ ID NOs: 3 to 5 or the homologous nucleotide sequence thereof. The "stringent conditions" herein denote a condition in which a so-called specific hybrid is formed and a non-specific hybrid is not formed. Such stringent conditions are well known to the person skilled in the art and can be set with reference to Molecular Cloning (Third Edition, Cold Spring Harbor Laboratory Press, New York) or Current protocols in molecular biology (edited by Frederick M. Ausubel et al., 1987). An example of the stringent conditions includes a condition in which a DNA is incubated in a hybridization solution (50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, 50 mM phosphate buffer (pH7.5)) at about 42° C. to about 50° C., followed by washing with 0.1×SSC and 0.1% SDS at about 65° C. to about 70° C. A more preferable example of the stringent conditions can include a condition using a hybridization solution (50% formamide, 5×SSC (0.15 M NaCl, 15 mM sodium citrate, pH 7.0), 1×Denhardt solution, 1% SDS, 10% dextran sulfate, 10 µg/ml denatured salmon sperm DNA, 50 mM phosphate buffer (pH 7.5)).

(Vector)

Another aspect of the present invention relates to a vector containing the nucleic acid of the present invention. The term "vector" in this specification refers to a nucleic acid molecule that can transport a nucleic acid inserted therein to a cell, and the like.

The vector of the present invention can be prepared by introducing the nucleic acid of the present invention (typically, DNA) into an existing vector or a vector obtained by modifying the existing vector. Any vectors may be used as a starting material in principle as long as they can carry the nucleic acid of the present invention, however, an appropriate vector can be selected in accordance with the purpose of use (cloning, expression of polypeptide), and considering the kinds of host cells.

Typically, a vector for transformation contains an AMP deaminase gene (for example, DNA having a sequence of SEQ ID NO: 4), a promoter and a terminator. In order to achieve an appropriate transcription of a structural gene by a promoter, a promoter, an AMP deaminase gene and a terminator are arranged successively from the upper stream toward the lower stream.

The vector of the present invention is preferably an expression vector. The "expression vector" is a vector capable of introducing the nucleic acid inserted into the vector to the inside of the cell (host cell) and capable of expressing in the cell. The expression vector generally includes a promoter sequence necessary for expression of nucleic acid, an enhancer sequence promoting the expression, and the like. An expression vector including a selected marker can be used. In the case where such an expression vector is used, it is possible to confirm the presence (and the extent) of introduction of the expression vector by using the selected marker.

An insertion of the nucleic acid of the present invention into a vector, an insertion of a selected marker gene (if necessary), insertion of a promoter (if necessary), and the like, can be carried out by using a standard recombination DNA technology (for example, Molecular Cloning, Third Edition, 1.84, Cold Spring Harbor Laboratory Press, New York can be referred. A well-known method restriction enzyme and DNA ligase). Note here that when a vector carrying DNA that also includes a promoter region (for example, DNA having a nucleotide sequences of SEQ ID NO: 3) is constructed, the recombinant vector may be constructed by preparing the promoter region of DNA and the other region independently and introducing them into a vector. In such a case, on the condition that a promoter function can be appropriately exhibited, other sequence may be intervened between both regions (promoter region and the other regions) in the vector. Furthermore, firstly, a vector carrying a promoter region may be constructed and then linked to the other regions.

The above-mentioned recombinant vector is used for transformation of a host. That is to say, by using the above-mentioned recombinant vector, transformant into which the nucleic acid molecule of the present invention is introduced can be prepared.

(Transformant and Use thereof)

The vector for transformation can be used for transforming a host. That is to say, by using the above-mentioned vector for transformation, a transformant into which the nucleic acid molecule of the present invention has been introduced can be prepared.

The host used for transformation is not particularly limited. *Streptomyces* such as *Streptomyces murinus* (IFO 14802, etc.), *Streptomyces lividans* (TK24, etc.), *Streptomyces griseus* subsp. *griseus*, *Streptomyces griseus*, *Streptomyces celluloflavus*, *Streptomyces coelicolor*, *Streptomyces mobaraensis*, *Streptomyces avermitilis* can be preferably used as a host. In addition to the above, *Escherichia coli*, *Bacillus subtilis*, *Saccharomyces cerevisiae*, *Saccharomyces pombe*, and the like, can be employed as a host.

The introduction of the vector for transformation into a host (transformation) can be carried out by a well-known method. For example, the transformation can be carried out by a method by D. A. Hopwood et al. (PRACTICAL STREPTOMYCES GENETICS P. 229-252 (The John Innes Foundation, 2000)) using protoplast fungus body.

The transformant can be used for production of AMP deaminase. Specifically, the transformant into which the nucleic acid of the present invention has been introduced is cultured under conditions capable of allowing protein (AMP deaminase) coded by the nucleic acid to express, and thereby AMP deaminase can be produced. The medium can be appropriately used in accordance with a host to be used. For example, it is possible to use commercially available various media or media to which proline, leucine, thiamin, and the like, which are components necessary for growth of transformant, selection, and promoting the expression of protein are added.

From a culture solution or fungus body, which have been cultured for a predetermined time, a target protein (AMP deaminase) can be collected. In the case where the proteins are produced outside the fungus body, they can be collected from the culture solution and in the other cases, the proteins can be collected from the inside of the fungus body. When the proteins are collected from a culture solution, for example, they can be obtained by subjecting the culture supernatant to filtration, centrifugation so as to remove insoluble substances, followed by carrying out isolation and purification by combining salting out such as ammonium sulfate precipitation, dialysis, various chromatography, and the like. On the other hand, when the proteins are collected from the inside of the fungus body, for example, they can be obtained by crushing the fungus body by pressurizing treatment, ultrasonic treatment, followed by carrying out isolation and purification as mentioned above. Note here that the above-mentioned series of processes (crushing of fungus bodies, isolation, and purification) may be carried out after fungus bodies are collected from a culture solution in advance by filtration, centrifugation, and the like. Since AMP deaminase of the present invention is produced outside of the fungus body, isolation and purification is carried out relatively easily.

Hereinafter, the present invention will be described in detail with reference to Examples, but the present invention is not necessarily limited to these Examples.

Example 1

Purification of AMP Deaminase Derived from *Streptomyces murinus*

1. Materials and Methods

Strains to be used in the following experiments, a preparation method of an enzyme solution and a method for measuring the enzyme activity are as follows.

<Strains to be Used>

*Streptomyces murinus* IFO14802, *Streptomyces griseus* subsp. *griseus* JCM4681, *Streptomyces griseus* IFO3355 (NBRC3355), and *Streptomyces celluloflavus* IFO13780 (NBRC13780) are used. Note here that *Streptomyces murinus* IFO14802 is deposited with the following international depositary agency. International depositary agency Name: National Institute of Advanced Industrial Science and Technology, International Patent Organism Depositary Address: Chuo No. 6, 1-3, Higashi 1-chome, Tsukuba-shi, Ibaraki-ken, 305-8566, Japan Deposition date: Mar. 29, 2004

Deposition (accession) No.: FERM BP-08673

<Method of Preparing Enzyme Solution>

(1) Enzyme Solution Derived from *Aspergillus melleus*

"Deamizyme (50,000 u/mg product) (trade name)" that is a commercially available AMP deaminase agent from Amano Enzyme Inc. is diluted with water so as to obtain an enzyme solution.

(2) Enzyme Solution Derived from *Streptomyces murinus*

Solpee NY (2%), Meast P1G (0.5%), NaCl (0.3%), $KH_2PO_4$ (0.1%), food additive $MgSO_4$ (0.05%) and soluble starch (3%) were added so as to adjust to pH 5.7 and sterilized at 121° C. for 30 minutes. *Streptomyces murinus* IFO14802 was inoculated, and precultured for one day, main-cultured for 5 days at 27° C. so as to prepare a crude enzyme solution.

(3) Enzyme Solution Derived from *Streptomyces*

Soyaflour A (2%), NaCl (0.3%), $KH_2PO_4$ (0.1%), food addition $MgSO_4$ (0.05%) and soluble starch (3%) were added so as to adjust to pH 5.7 and sterilized at 121° C. for 30 minutes, which is inoculated, precultured for one day and main-cultured for 5 days at 27° C. Thus, a crude enzyme solution was prepared.

<Method of Measuring Enzyme Activity>

(1) Method of Measuring AMP Deaminase Activity

By using the decrease of $OD_{265}$ at the time of reaction as an index, the enzyme activity was measured. To 1.5 ml of solution obtained by mixing 0.017M 5'AMP-2Na and 1/15M phosphate buffer solution (pH 5.6) at the ratio of 1:2, 0.5 ml of sample solution was added so as to obtain a reaction solution, which was reacted at 37° C. for 15 minutes. Then, 2% perchloric acid solution was added so as to stop the reaction and 100 μl of the solution was taken out. Water was added to the solution so that the total amount was 5 ml. Then, $OD_{265}$ was measured. The value similarly measured at reaction time of 0 minute was defined as a blank. Under the above-mentioned conditions, a case where an absorbance difference is reduced by 0.001 during 60 minutes was defined as one unit.

(2) Method of Measuring Phosphatase Activity

To 1.5 ml of solution obtained by mixing 0.025M 5'IMP-2Na and 0.036M barbital sodium-hydrochloric acid buffer solution (pH 5.6) at the ratio of 1:2, 0.5 ml of sample solution was added so as to obtain a reaction solution, which was reacted at 37° C. for 30 minutes. After the reaction was completed, 200 μl of the solution was taken out, and 5 ml of 6% perchloric acid solution was added so as to stop the reaction. Amidol solution (0.05M, 0.25 ml) was added and mixed, followed by adding and mixing 0.25 ml of 0.067 M ammonium molybdate solution, and further adding and mixing 0.25 ml of water, which was allowed to stand in flowing water for 15 minutes. Then, $OD_{265}$ was measured. A value similarly measured at the reaction time of 0 minute was defined as a blank. Under the above-mentioned conditions, a case where an absorbance difference is reduced by 0.001 during 30 minutes was defined as one unit.

2. Results (1) Theremostability

Thermostability was compared between AMP deaminase produced by *Aspergillus melleus* and AMP deaminase produced by *Streptomyces murinus*. *Aspergillus melleus* and *Streptomyces murinus* were examined for the residual AMP deaminase activity (pH 5.6) after 1% enzyme solution prepared by the above-mentioned method was treated at a predetermined temperature. Note here that the treating temperatures were set to 30° C., 40° C., 50° C., 60° C., 65° C., 70° C., and 75° C. The treating time was set to 30 minutes.

The measurement results are shown in a graph of FIG. 1. FIG. 1 shows that AMP deaminase derived from *Streptomyces murinus* was extremely excellent in thermostability.

(2) Contaminated Phosphatase

The contaminated phosphatase activities concerning *Aspergillus melleus* and *Streptomyces murinus* were measured. The phosphatase activity/deaminase activity (P/D) calculated from the measurement results are summarized in FIG. 2. In *Aspergillus melleus*, the contamination activity was observed. On the other hand, in *Streptomyces murinus*, the phosphatase activity was not observed. That is to say, it was found that AMP deaminase produced by *Streptomyces murinus* had extremely low contaminated phosphatase activity.

(3) IMP Conversion Reaction

IMP conversion rate by HPLC of AMP deaminase produced by *Aspergillus melleus* and *Streptomyces murinus* was examined. Specifically, by using 1/15M phosphate buffer solution (pH 7.0), 1.1% AMP solution was prepared. To 5 ml of 1.1% AMP solution, 0.5 ml of enzyme solution was added and reacted at 50° C. for 4 hours. Thereafter, heat treatment at 100° C. was carried out for 10 minutes, filter filtration (0.45 µm) was carried out, and HPLC analysis was carried out.

Figure 3:
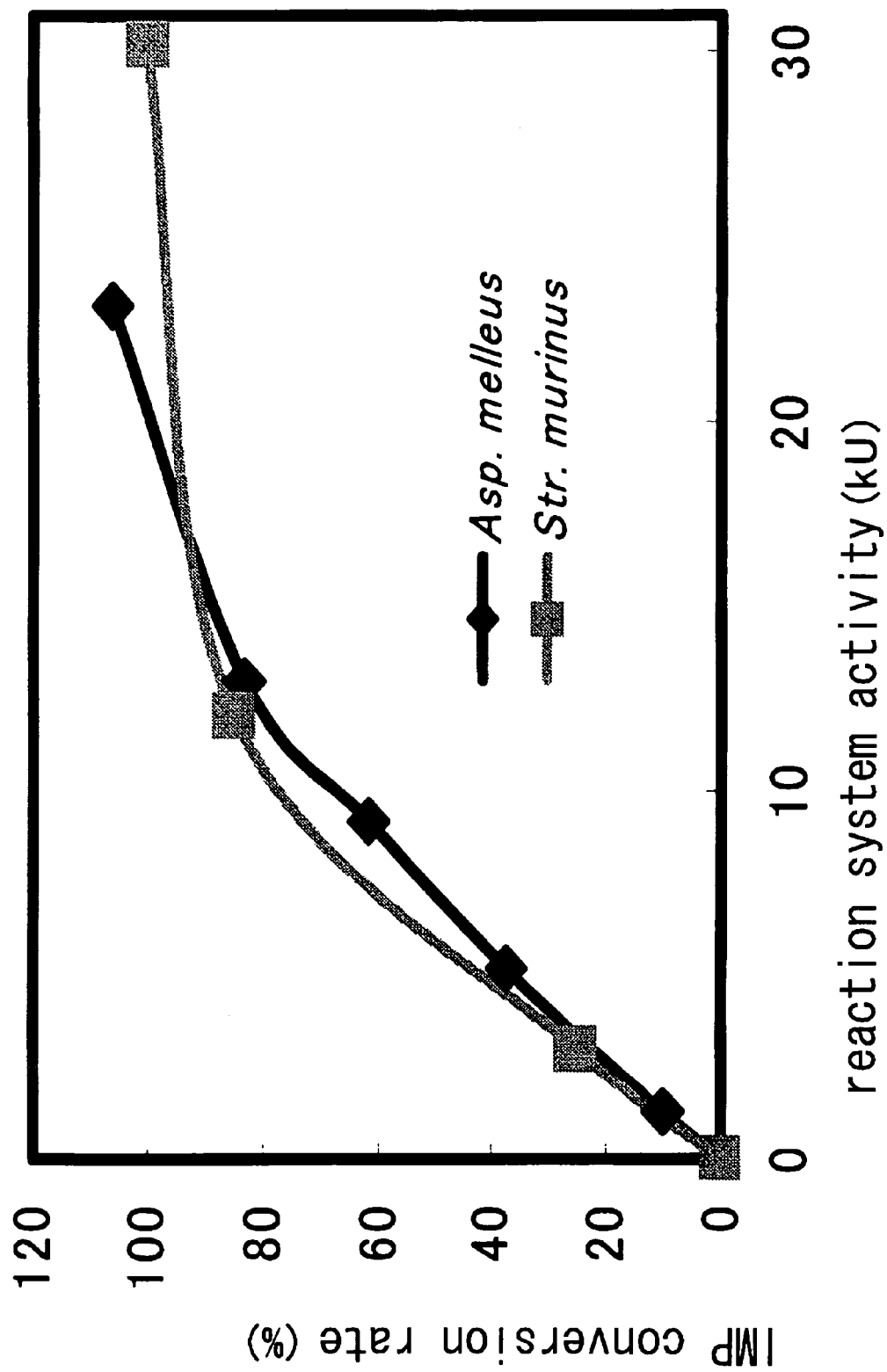
FIG. 3 is a graph showing the comparison of IMP conversion rate of AMP deaminases produced by *Aspergillus melleus* and *Streptomyces murinus*.

The measurement results are shown in FIG. 3. The IMP conversion rate (IMP conversion speed) of AMP deaminase produced by *Streptomyces murinus* was the same level as that of AMP deaminase produced by *Aspergillus melleus*. As mentioned above, since in *Streptomyces murinus* did not exhibit contaminated phosphatase activity, specification of the side product was carried out. As a result, the ratio of the side product (hypoxanthine) was smaller than the case of *Aspergillus* melleus (results are not shown).

(4) Feasibility Test

In order to confirm that AMP deaminase derived from *Streptomyces murinus* is effective in the actual production of yeast extract, the following tests (test 1 and test 2) were carried out.

a) Test 1

In test 1, similar to the current production method, treatment with nuclease and treatment with deaminase were carried out independently. Specifically, the treatment was carried out by the following procedure and the IMP conversion rate was calculated. Firstly, nuclease "AMANO" G (Amano Enzyme Inc., 0.1% w/w yeast solid) was added to yeast lysate (YL-15, 0.2%) and they were reacted with each other under the conditions at a temperature of 70° C. and pH 5 for 3 hours. Then, "Deamizyme (50,000 u/mg product) (trade name of Amano Enzyme Inc., 0.01 to 0.04% w/w yeast solid)" that is an AMP deaminase agent derived from the test enzyme (*Aspergillus melleus*), or a crude enzyme solution prepared from *Streptomyces murinus* was added and reacted with each other under the conditions at a temperature of 50° C. and pH 6 for 5 hours. Then, the reacted product was heat treated, and then subjected to HPLC analysis. Note here that added amount of AMP deaminase derived from *Streptomyces murinus* was set so that the activity value thereof became the same as that of "Deamizyme (50,000 u/mg product)" (trade name, Amano Enzyme Inc.)

b) Test 2

In test 2, treatment with nuclease and treatment with deaminase were carried out simultaneously. Specifically, the treatment was carried out by the following procedure and the IMP conversion rate was calculated. Firstly, nuclease "AMANO" G (Amano Enzyme Inc., 0.1% w/w yeast solid) and "Deamizyme (50,000 units) (trade name of Amano Enzyme Inc., 0.01 to 0.04% w/w yeast solid)" that is an AMP deaminase agent derived from the test enzyme (*Aspergillus melleus*) or a crude enzyme solution prepared by using *Streptomyces murinus* were added to yeast lysate (YL-15, 0.2%) and they were reacted with yeast lysate under the conditions at a temperature of 70° C. and pH5 for a predetermined time (3 hours or 5 hours). Then, the reacted product was heat treated, and then subjected to HPLC analysis. Note here that added amount of AMP deaminase derived from *Streptomyces murinus* was set so that the activity value thereof became the same as that of "Deamizyme (50,000 u/mg product)" (trade name, Amano Enzyme Inc.)

Figure 4:
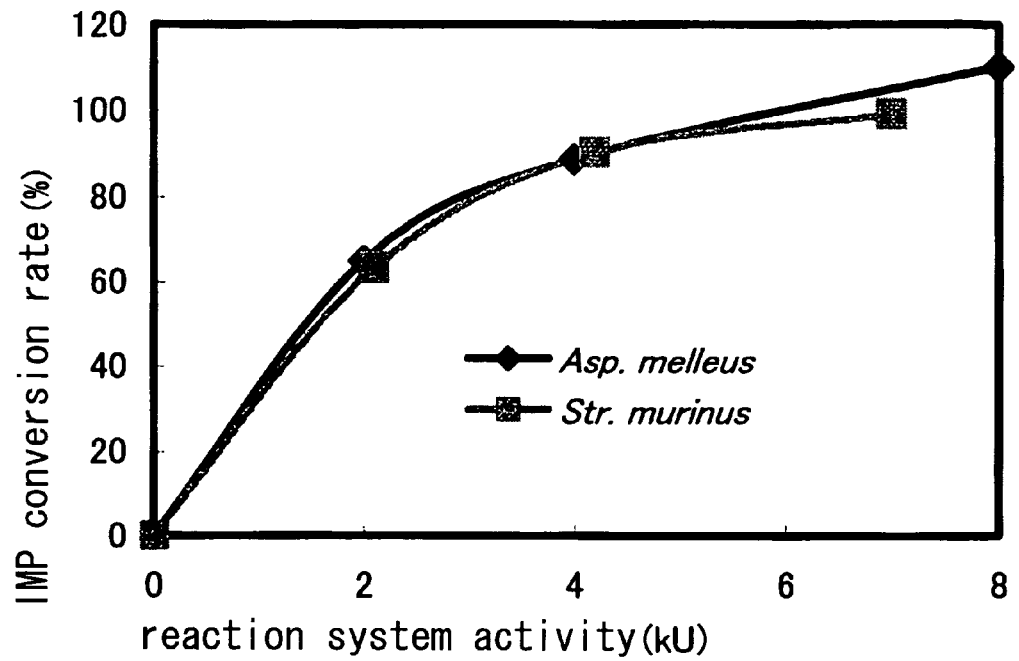
FIGS. 4 (*a*) and (*b*) are graphs showing the comparison of IMP conversion rate in a case where AMP deaminase derived from *Streptomyces murinus* is allowed to act in the production process of yeast extract.
Figure 4:
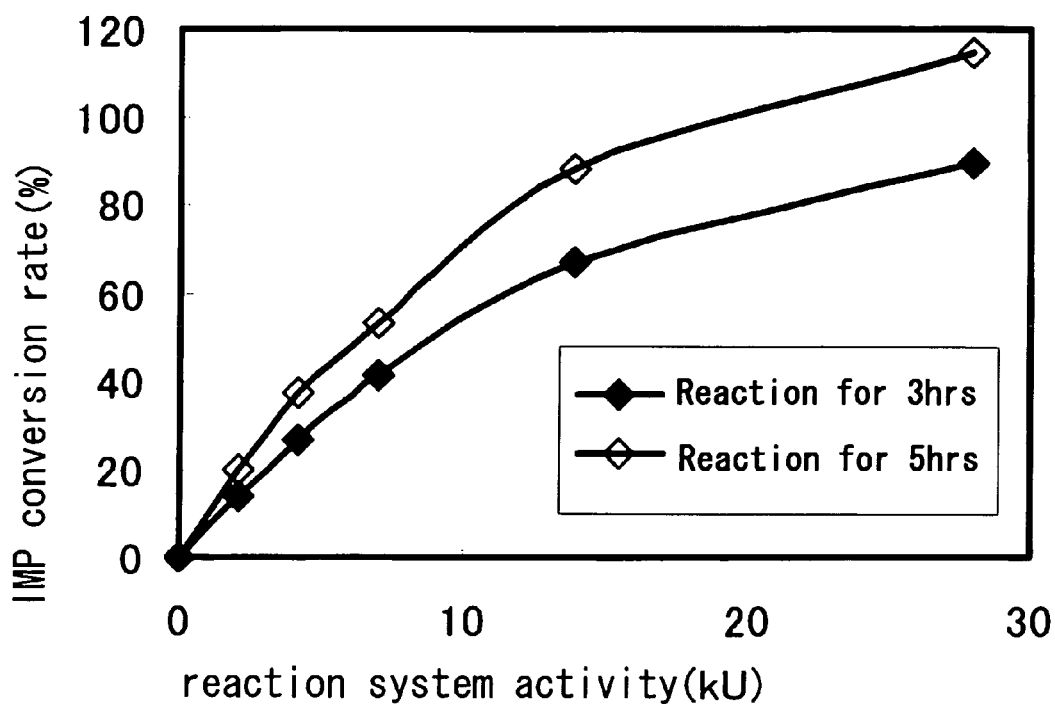

The results of test 1 are shown in FIG. 4 (*a*). As is apparent from FIG. 4 (*a*), AMP deaminase from *Streptomyces murinus* exhibits the equivalent IMP conversion rate to that of AMP deaminase derived from *Aspergillus melleus* (Deamzyme: 50,000 u/mg product).

On the other hand, the results of test 2 are shown in FIG. 4 (*b*). In this graph, "3 hrs" denotes the measurement results when AMP deaminase derived from *Streptomyces murinus* was allowed to act on simultaneously for 3 hours; and "5 hrs" denotes the measurement results when AMP deaminase derived from *Streptomyces murinus* was allowed to act simultaneously for 5 hours. Note here that no IMP was produced in the case where AMP deaminase derived from *Aspergillus melleus* (Deamzyme; 50,000 u/mg, product) was used (both in the reaction for 3 hours and 5 hours). As is apparent from FIG. 4 (*b*), when AMP deaminase derived from *Streptomyces murinus* was used, IMP was produced when it was allowed to act simultaneously with nuclease at high temperatures. Thus, it was confirmed that AMP deaminase derived from *Streptomyces murinus* was able to be reacted simultaneously with nuclease.

(5) Enzymological Property of AMP Deaminase Derived from *Streptomyces murinus*

Figure 5:
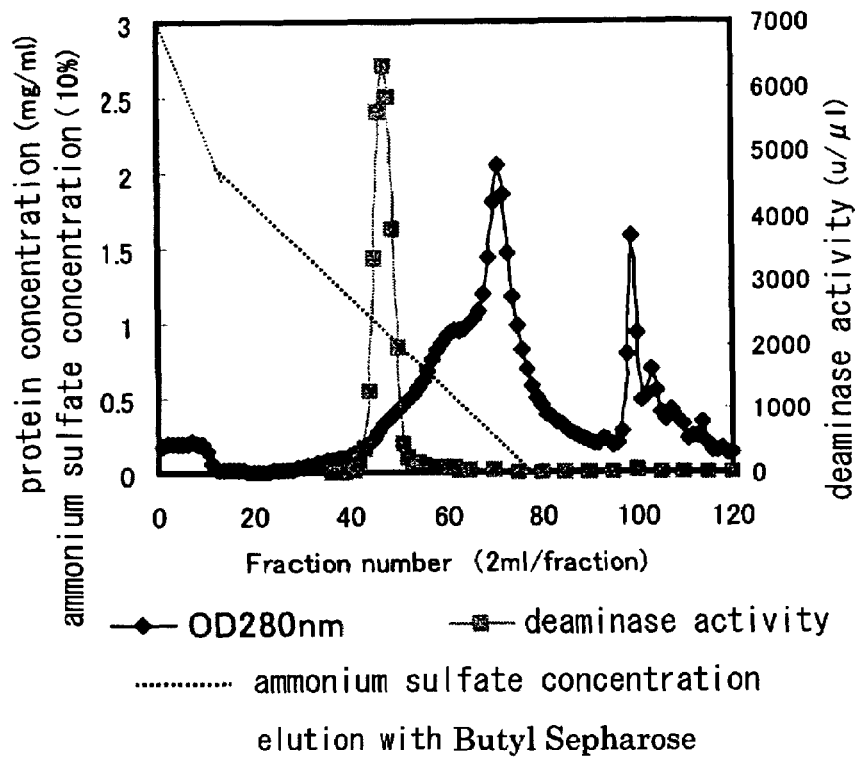
FIGS. 5 (*a*) and (*b*) are graphs showing chromatography results by the purification process of AMP deaminase derived from *Streptomyces murinus*.
Figure 5:
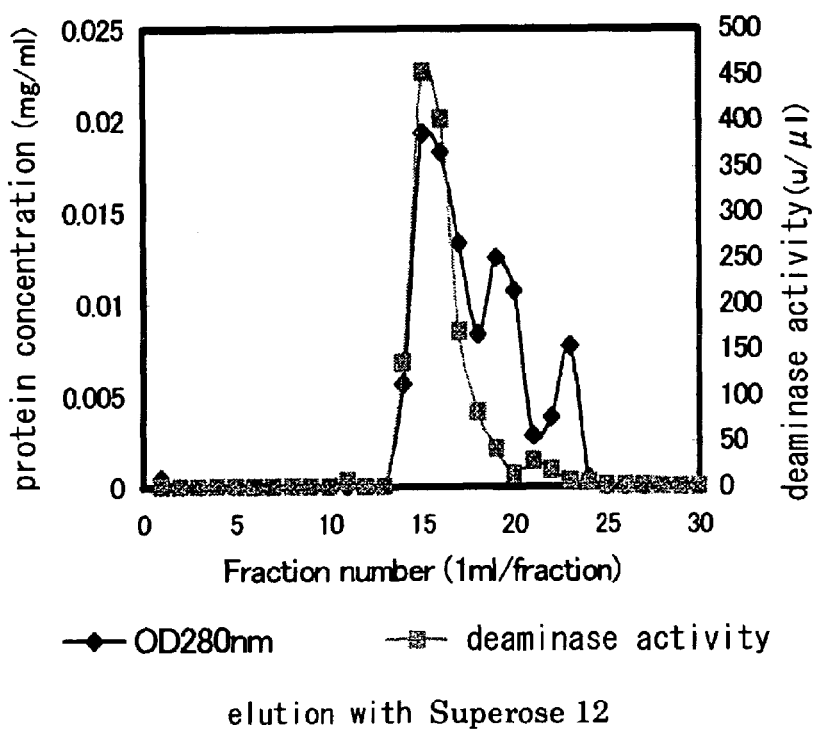
Figure 6:
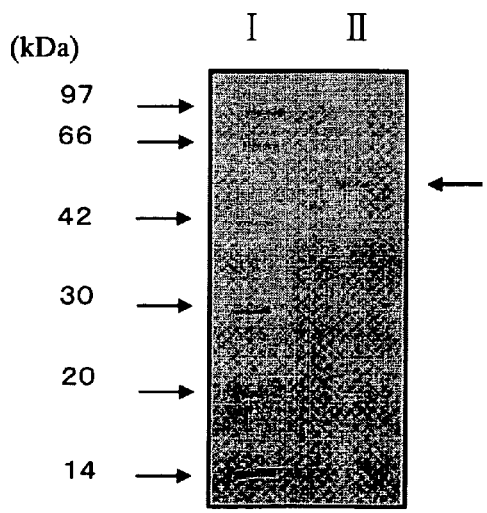
FIG. 6 (*a*) is a table summarizing total enzyme activity, total protein amount, specific activity, and yield in the purification process of AMP deaminase derived from *Streptomyces murinus*.

AMP deaminase derived from *Streptomyces murinus* has been attempted to be purified by the following procedures. Firstly, *Streptomyces murinus* (IFO14802) was cultured by the above-mentioned method and the produced enzyme was concentrated two times with ultrafiltration membrane (AIP1010). Water was added to the concentrated solution, which was further concentrated so as to remove low molecular fractions. Then, the product was lyophilized so as to obtain a crude enzyme. This crude enzyme was dissolved in purified water and subjected to ammonium sulfate fractionation by using saturated ammonium sulfate (48%). The precipitated fraction was dissolved in 20 mM KPB (pH 7.0) so as to obtain an enzyme solution. The obtained enzyme solution was allowed to pass through HiPrep™16/10 ButylFF (Pharmacia Corporation) that had been equilibrated with 20 mM KPB (pH 7.0) containing 30% ammonium sulfate, followed by eluting at a concentration gradient of 300%~0% by 20 mM KPB (pH 7.0) containing ammonium sulfate (30%~0%). Thereafter, they were concentrated and the active fraction was subjected to gel filtration by using Superose 12 column (Pharmacia Corporation) so as to be eluted with 50 mM KPB (pH 7.0) containing 150 mM NaCl. Active fractions (fraction 15 and 16) were collected so as to obtain purified enzyme. Note here that the results of chromatography by using HiPrep™16/10 ButylFF is shown in FIG. 5(a); and the results of chromatography by using Superose 12 is shown in FIG. 5(b). Furthermore, the total activity amount, the total protein amount, specific activity, and yield in each stage are shown in FIG. 6 (a). The specific activity at the final stage came to be 96 times as that of the crude enzyme.

Purified enzyme was subjected to SDS-PAGE (CBB staining), and the purity of protein was confirmed. The results of SDS-PAGE are show in FIG. 6 (b). Lane II shows a sample lane (purified enzyme). Lane II shows a single band, showing that the purity of the purified enzyme is high. Note here that lane I shows bands of protein molecular weight markers. Bands of phosphorylase b (M.W. 97,400), bovine serum albumin (M.W. 66,267), aldolase (M.W. 42,400), carbonic anhydrase (M.W. 30,000), trypsin inhibitor (M.W. 20,100), and lysozyme (M.W. 14,400) are shown sequentially from the side of high molecular weight.

Figure 7:
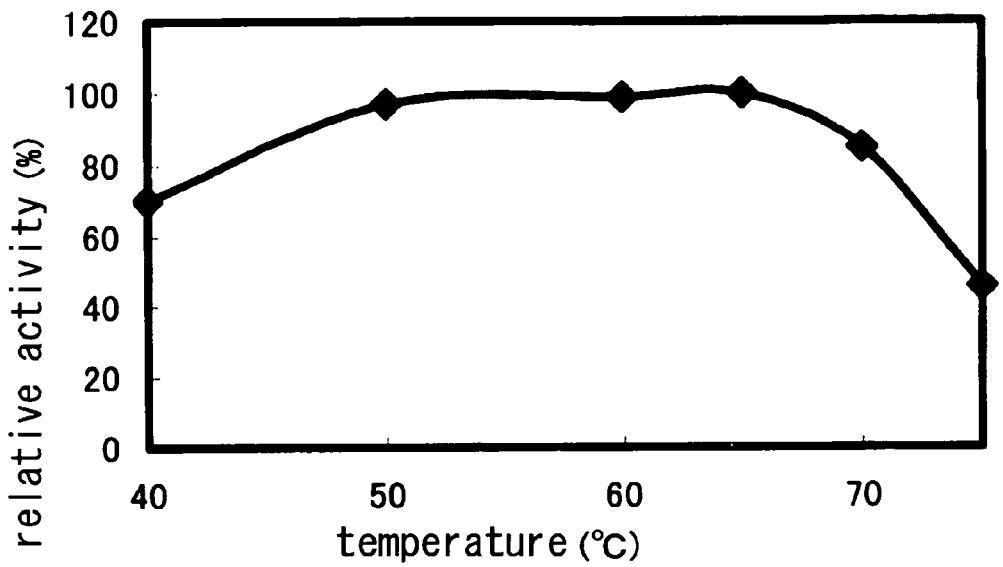
FIG. 7 (*a*) is a graph showing a relation between a reaction temperature and activity of AMP deaminase derived from *Streptomyces murinus*.
Figure 7:
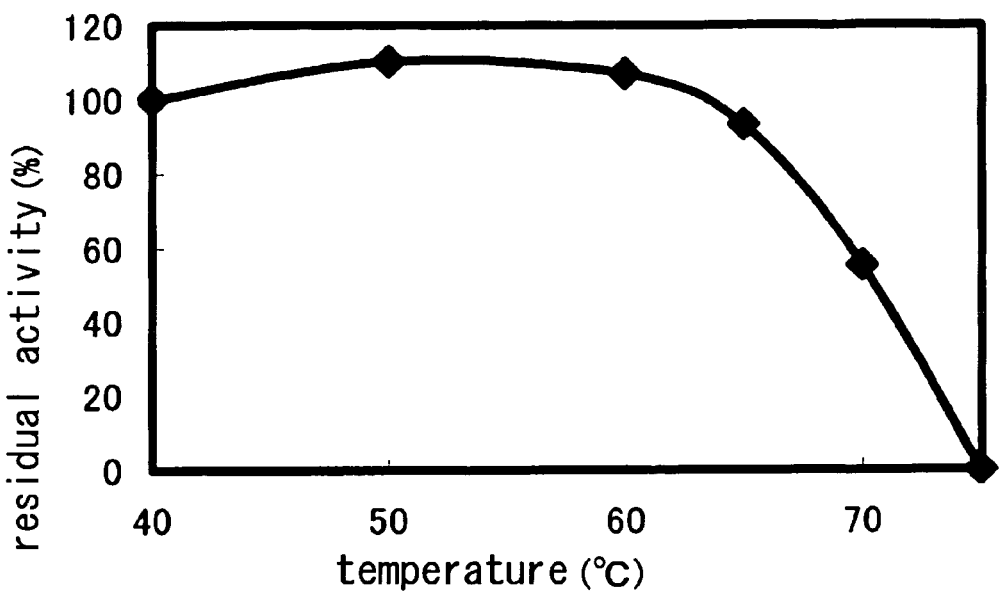

The relation between the reaction temperature and activity of the obtained purified enzyme was examined. The measurement results are shown in FIG. 7(a). A graph of FIG. 7 (a) shows the relative activity (%) when the activity value in the reaction at 65° C. is defined as 100%. As is apparent from the graph of FIG. 7 (a), high activity is observed in the wide range from 40° C. to 70° C. Furthermore, even in the case where the reaction temperature is 75° C., about 50% activity is found. Thus, it is shown that the enzyme acts favorably under the wide range of temperatures.

Subsequently, the thermostability of the enzyme was examined by the following procedure. An enzyme solution (0.15 ml) containing 2.8 μg protein (total amount) was adjusted to pH 5.6 by using acetate buffer (pH 5.0), and then treated for 30 minutes at each temperature (40° C., 50° C., 60° C., 65° C., 70° C., and 75° C.). Then, the residual activity (percent with respect to the enzyme activity in the case where the treatment was not carried out) was measured. The measurement results are shown in FIG. 7 (b). At 65° C. or less, about 90% or more of activity is maintained. Furthermore, also when the treatment is carried out at 70° C., about 55% of the activity is maintained. Thus, it was found that the enzyme had extremely excellent thermostability.

Figure 8:
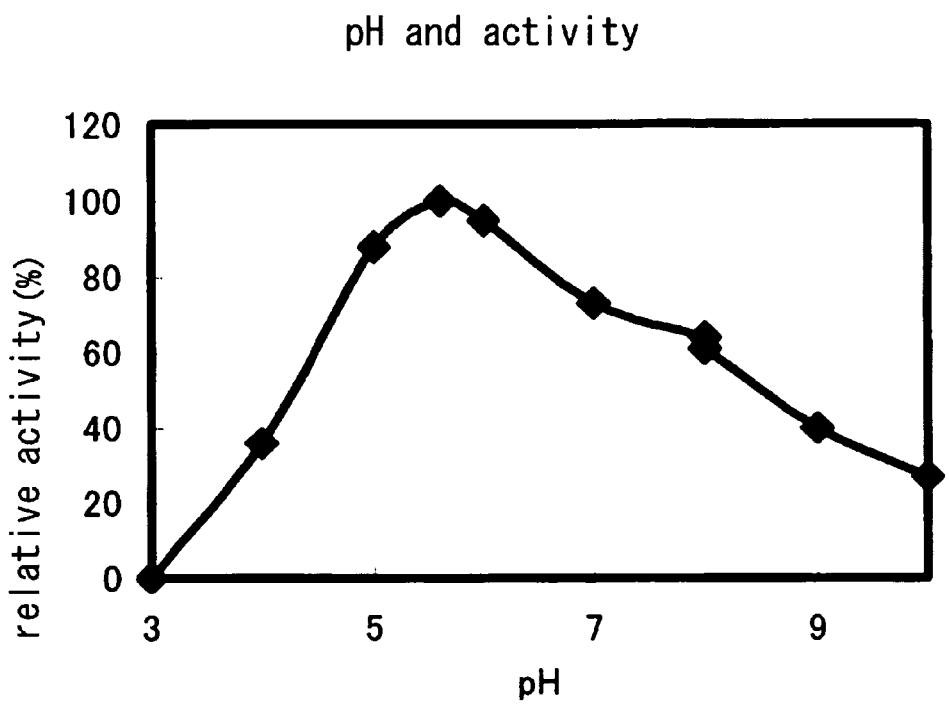
FIG. 8 (*a*) is a graph showing a relation between pH and activity of AMP deaminase derived from *Streptomyces murinus*.
Figure 8:
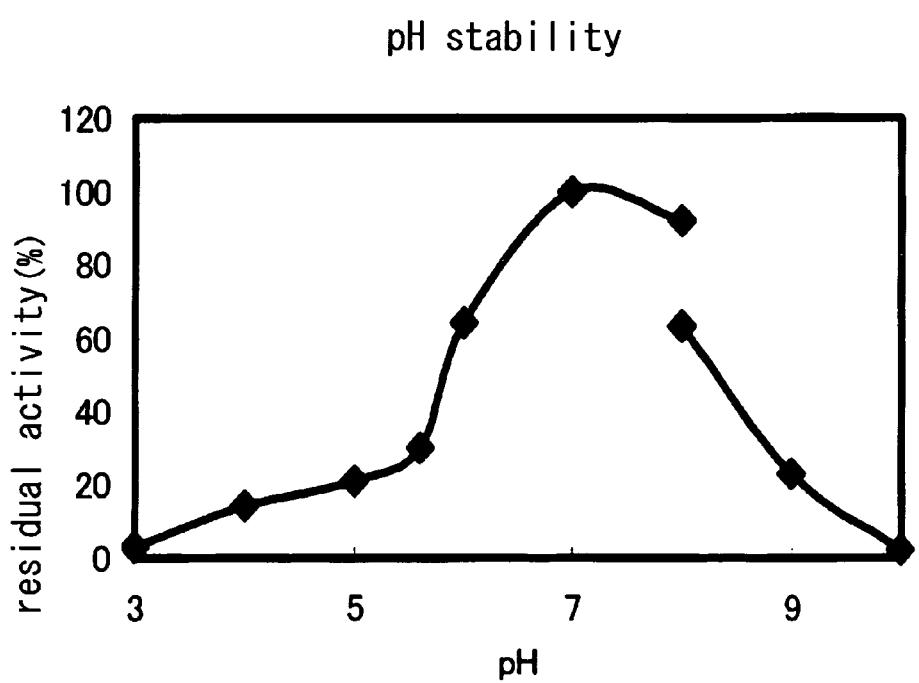

Next, the relation between pH and activity of the obtained purified enzyme was examined. The measurement results are shown in FIG. 8(a). A graph of FIG. 8 (a) shows the relative activity (%) when the activity value obtained in the reaction at pH 5.6 is defined as 100%. In the wide range of pH from about 4.5 to about 8.5, relatively high activity is observed. In the range of pH from about 5.0 to about 8.0, 70% or more of the reaction property is observed. Furthermore, it is shown that even in the case where pH is 9.0, about 40% of reactivity is obtained.

Next, pH stability of the enzyme was examined by the following procedure. An enzyme solution (0.15 ml) containing 2.8 μg protein (total amount) was adjusted to pH 3 to 8 by using McIlvaine buffer solution, and to pH 8 to 10 by using Atkins-pantin buffer solution. The solution was then allowed to stand at 30° C. for 30 minutes. Thereafter, the residual activity (percent with respect to the enzyme activity in the case where the treatment was carried out in pH 7.0) was measured. The measurement results are shown in FIG. 8 (b). It is shown that in the range of pH from about 6.0 to about 8.5, relatively high activity is maintained, and in the range of pH from about 6.5 to about 8.0, about 80% or more of activity is maintained.

(6) Substrate Specificity of AMP Deaminase Derived from *Streptomyces murinus*

It is reported that adenosine deaminase derived from *Streptomyces aureofaciens* has a wide range of substrate property, for example, catalytic ability of AMP (non-patent document 2). Taken this into consideration, in order to confirm whether deaminase derived from *Streptomyces murinus* obtained in the above-mentioned method is AMP-deaminase or adenosine-deaminase, the substrate specificity was investigated. The results are shown in FIG. 9. Note here that the relative activity, when the enzyme activity with respect to 5' AMP is defined as 100% is represented. The enzyme acted on 5' AMP most favorably. Furthermore, the enzyme also acted on 3'AMP, 5'dAMP, ADP, ATP, Adenosine and 3'5'-cyclic AMP, but the enzyme did not act on 2'AMP, adenine at all. In particular, the enzyme acted on 5'dAMP, ADP and ATP favorably. From the above-mentioned results, it was confirmed that the deaminase derived from *Streptomyces murinus* obtained by the above-mentioned method was AMP deaminase. Furthermore, it was determined that the enzyme was able to be employed preferably in a reaction using 5'dAMP, ADP and ATP as a substrate.

(7) Enzymological Property of AMP Deaminase Derived from *Streptomyces murinus*

Figure 10:
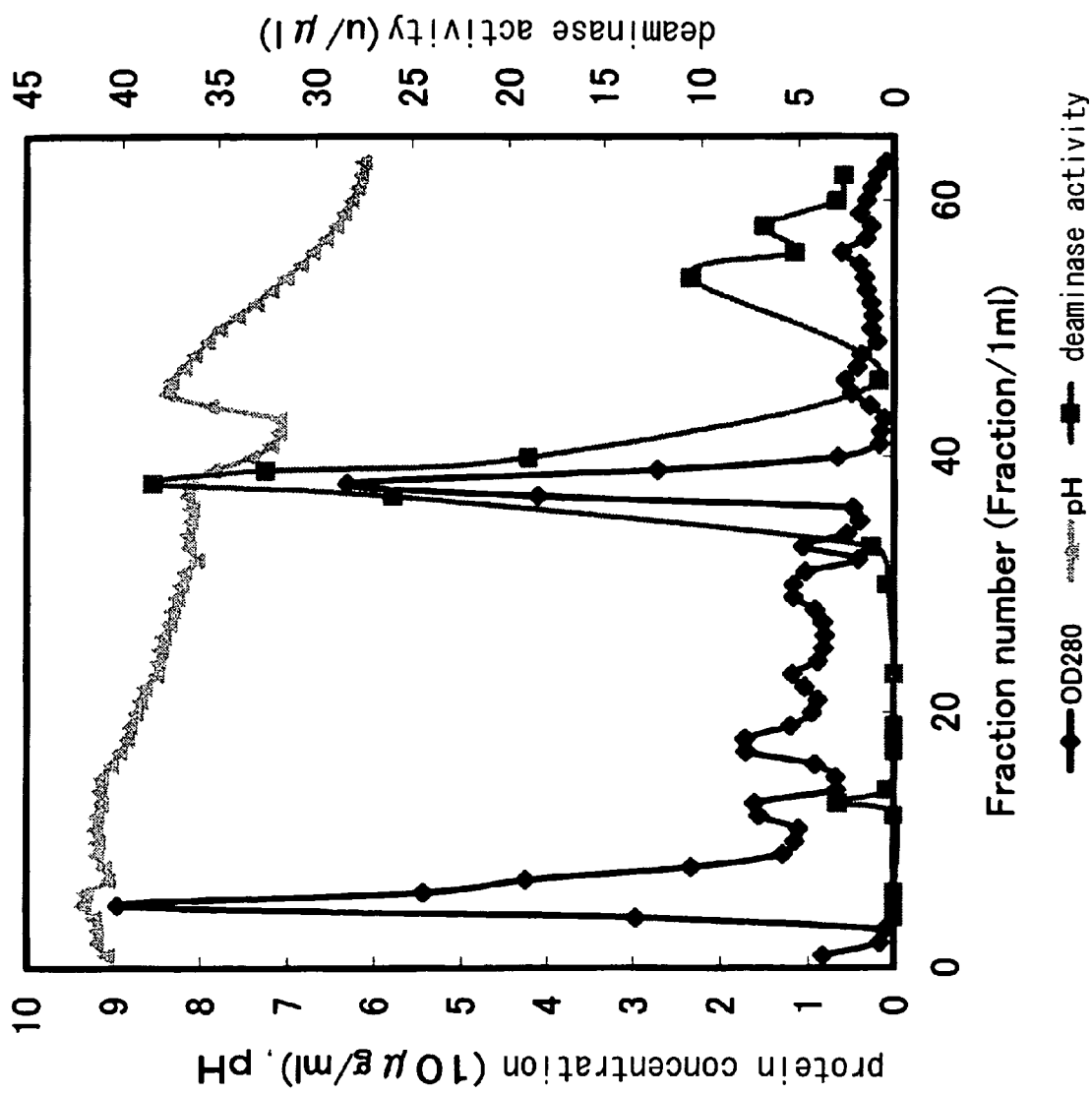
FIG. 10 is a graph showing results of chromatofocusing analysis of AMP deaminase derived from *Streptomyces murinus*.

In order to obtain an isoelectric point of AMP deaminase derived from *Streptomyces murinus* obtained by the above-mentioned method, chromatofocusing was carried out. By using MonoP column (Pharmacia), a starting buffer (Start Buffer) and an elution buffer (Poly buffer 96) were adjusted to pH 4.0 with 0.075M Tris acetate buffer (pH9.3) and with hydrochloric acid, respectively. The final amount was made to 100 ml. Furthermore, Pre-gradient with 3 ml, gradient elution with 30 ml and elution with 30 ml were carried out. The results of the chromatofocusing is shown in FIG. 10. From the results, it was thought that at least two isozymes were present (pI 8.12, 7.02), but the isoelectric point of main fraction was 8.12. Various properties, including the isoelectric point obtained from the above-mentioned results, of AMP deaminase derived from *Streptomyces murinus*, are shown in FIG. 11. As shown in this table, AMP deaminase derived from *Streptomyces murinus* had a molecular weight of about 48,000±2,000 in gel filtration (while molecular weight was 60,000±3,000 in SDS-PAGE). The optimum pH was around 5.6, the optimum temperature was about 65° C., the isoelectric point was 8.12, Km value was 0.95 mM and Vmax was $3.5 \times 10^7$ μmol/min/mg.

(8) Search of AMP Deaminase Producing Strain from the Genus *Streptomyces*

Since the above-mentioned investigation showed that *Streptomyces murinus*, which was one of the *Streptomyces* of the genus *Streptomyces*, produced thermal resistant AMP deaminase, it was expected that thermal resistant AMP deaminase might be produced from the other strain of the genus *Streptomyces*. Then, in the genus *Streptomyces* in the stored strains of Amano Enzyme Inc., screening of AMP deaminase producing strain was carried out. As a result, a strain capable of producing AMP deaminase was found in three strains, that is, *Streptomyces griseus* subsp. *griseus*, *Streptomyces griseus*, and *Streptomyces celluloflavus*. The thermostability and substrate specificity of AMP deaminase produced form these three strains were investigated. The results are shown in FIG. 12. In the thermostability test, a crude enzyme solution obtained by culture was used, and the treatment was carried out under the conditions at 65° C. for 30 minutes. Furthermore, the residual activity was measured when the activity obtained when treatment was not carried out was defined as 100%. With respect to the substrate specificity (specificity with respect to adenosine), the relative activity with respect to the activity value when AMP was used as a substrate was defined as 100%.

As is apparent from FIG. 12, the above-mentioned three strains had more excellent thermostability than deaminase derived from *Aspergillus melleus* did. This suggested that deaminase produced by *Streptomyces* of the genus *Streptomyces* generally tended to have high thermostability. Note here that it was confirmed that deaminase produced by the above-mentioned three strains acted on AMP more favorably than adenosine did.

Example 2

Identification of AMP Deaminase Derived from *Streptomyces murinus*

1. Analysis of Amino Acid Sequence

*Streptomyces murinus* IFO 14802 was cultured in accordance with the procedures in the above-mentioned Examples so as to obtain a purified enzyme. However, purification was stopped at the purification by Butyl Sepharose column by using HiPrep™16/10 ButylFF (Pharmacia). Fraction samples were subjected to SDS-PAGE by using gel PAG Mini "DAIICHI" 10/20 (Daiichi Pure Chemicals Co., Ltd.). Gel after electrophoresis was transferred to a PVDF membrane by using Towbin buffer solution (25 mM Tris, 192 mM glycine, and 5% methanol) containing 0.01% SDS as a buffer solution. The transferring operation was carried out by using a buffer tank type transferring device under the conditions at constant voltage of 20V, at a temperature of 4° C. for 18 hours. After transfer, CBB (Coomassie Brilliant Blue R 250) (Fluka) staining was carried out, and a band corresponding to the enzyme was cut out for use in a sample for analyzing N-terminal amino acid sequence. Similarly, gel after electrophoresis was stained with CBB and a band corresponding to the enzyme was cut out for use in a sample for analyzing the inside amino acid sequence. The amino acid sequence of these samples were analyzed and the analyzed results are shown in FIG. 13.

2. Extraction of Genome DNA from *Streptomyces murinus* IFO14802

In accordance with the procedure in the above-mentioned Example, *Streptomyces murinus* IFO14802 was cultured, and the cultured solution was filtered by using a Buechner funnel and a Nutsche filtering flask so as to obtain a fungus body. The fungus body (1 g) was suspended in 10 ml of TE (10 mM Tris-HCl (pH 8.0) and 1 mM EDTA) solution containing 4 mg/ml lysozyme (Roche Diagnostics), and 2 mg/ml Achromopeptitase (Wako Pure Chemical Industries) and was subjected to bacteriolysis at 30° C. for one hour. To the suspension, 2.4 ml of 0.5 mM EDTA solution was added, and 260 µl of 10 mg/ml Pronase E (Kaken Kagaku) was added and further subjected to bacteriolysis at 30° C. for 5 minutes. Then, 1.4 ml of 10% SDS solution was added, mixed up and down, and incubated at 37° C. for two hours. Phenol (12 ml), which had been equilibrated with a TE solution containing 0.1 M NaCl, was added and stirred for five minutes. Thereafter, 12 ml of chloroform was added and stirred for further five minutes. Then, centrifugation (at 1,500 g at room temperature for five minutes) was carried out so as to obtain the supernatant. This operation was repeated twice. To the obtained supernatant, 72 µl of 10 mg/ml RNase A (SIGMA ALDRICH JAPAN) was added and incubated at 37° C. for one hour. Five M NaCl (4.5 ml) was added and mixed, then 11.25 ml of 30% polyethylene glycol 6000 (Wako Pure Chemical Industries) solution was added and mixed, and allowed to stand at 4° C. overnight. Precipitated genome DNA was spooled out by using a Pasteur pipette, then washed with 70% ethanol and air-dried. Thereafter, the genome DNA was dissolved in 1 ml of TE solution so as to obtain about 1 mg/ml of genome DNA solution.

3. Design of Synthetic Primer

By taking the analysis results of the above-mentioned internal amino acid sequence into consideration, the below-mentioned synthetic primers (Invitrogen) were designed.

Primer IS-F 5'-TTC GGI GAG GTI ACI GCI CGI CAY MG-3' (SEQ ID NO: 6) Amino acid sequence, N-terminus-F G B V T A R H R G-C-terminus (SEQ ID NO: 25), Primer IS-R 3'-CTY CGI CTR CTG CCI CTG CGI CTC AA-5' (SEQ ID NO: 7) Amino acid sequence, N-terminus-B A D D G D A B F R-C-terminus (SEQ ID NO: 26).

4. Production of Probe for Southern Hybridization and Colony Hybridization

A PCR reaction was carried out by using the above-mentioned genome DNA derived from *Streptomyces murinus* IFO14802 as a template. By using TaKaRa LA Taq™ with GC buffer (Takara Shuzo Co., Ltd.), 2 µM of the above-mentioned synthetic primers IS-F and IS-R and 50 ng of genome DNA as a template were added to a reaction system. As the reaction, incubation at 96° C. for 3 minutes was carried out, then a cycle of incubation at 96° C. for 45 seconds, 66° C. for one minute and 72° C. for 3 minutes was repeated 35 cycles, and finally incubation at 72° C. for 10 minutes was carried out. After agarose electrophoresis was carried out, about 240 bp of DNA fragment, which had been specifically amplified by using GENECLEAN™III (BIO101), was extracted. The extracted DNA fragments were subcloned to pGEM™-T Easy (Promega), followed by extracting the insertion DNA fragment again. Then, DIG label was added by using DIG High Prime (Roche Diagnostics) and a probe of an AMP deaminase gene was obtained.

5. Southern Hybridization

Figure 14:
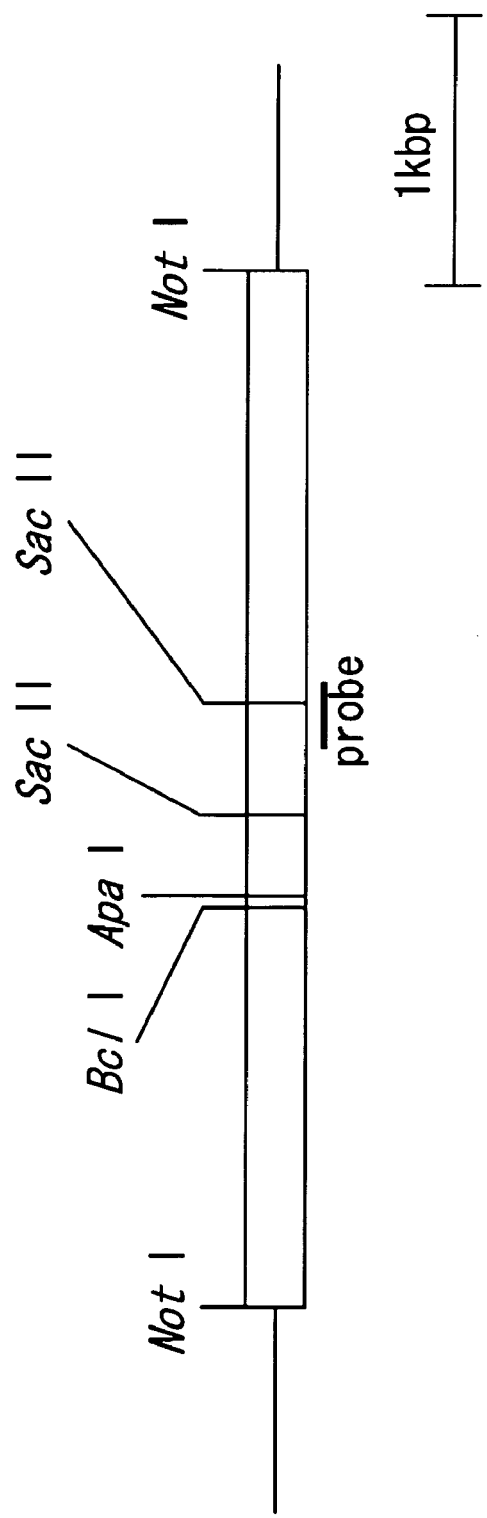
FIG. 14 shows a restriction map of AMP deaminase derived from *Streptomyces murinus*.

Agarose electrophoresis was carried out, in which 6 µg of genome DNA that had been completely digested with arbitrary restriction enzyme was applied for each lane. The DNA was treated with 0.25N HCl solution for 30 minutes, neutralized with buffer used for electrophoresis and then was blotted to Zeta-Probe™ membrane (Bio-Rad) by alkaline blotting using 0.4N NaOH solution. Transcription was carried out by using 2016 VacuGene (Pharmacia LKB Biotechnology) at degree of vacuum of 50 cm·H$_2$O for 90 minutes. After blotting, the membrane was washed with 2×SSC (NaCl 0.3M, sodium citrate 33.3 mM) solution and air-dried, followed by incubating at 80° C. for 30 minutes, and DNA was immobilized to the membrane. The immobilized membrane was subjected to Southern hybridization by using the above-mentioned probe. The detection was carried out by using DIG Nucleic Acid Detection Kit (Roche Diagnostics). Thus, a restriction map of the enzyme gene was produced (FIG. 14).

6. Colony Hybridization

Genome DNA (12 µg) was completely digested by using a restriction enzyme Not I (Takara Shuzo Co., Ltd) and then subjected to agarose electrophoresis so as to cut out a DNA fragment having a DNA chain length of 3.8 kbp. Then, extraction was carried out by using GENECLEAN™III (BIO 101) so as to obtain an insert for producing a library. At the same time, pBluescriptII KS(+) (Stratagene) was completely digested by using Not I (Takara Shuzo Co., Ltd) and then dephosphorylated by using Alkaline Phosphatase (Takara Shuzo Co., Ltd) so as to obtain a vector for producing a library. The insert and vector were ligated by using Ligation Kit ver. 2 (Takara Shuzo Co., Ltd) and transformed into an *Escherichia coli* DH5 strain competent cell (TOYOBO CO., LTD) by Hanahan method (J Mol Biol. 1983 Jun. 5; 166(4): 557-80, Hanahan D., Studies on transformation of *Escherichia coli* with plasmids). The obtained clones were planted on a LA plate (ampicillin (SIGMA ALDRICH JAPAN) 100 µg/ml) so that about 500 colonies per one plate were formed and incubated at 37° C. overnight so as to grow the colonies. The grown colonies (total number of about 9500) were lifted to Nylon Membranes for Colony and Plaque Hybridization (Roche Diagnostics) and DNA was immobilized on the membrane. Colony hybridization was carried out by using the aforementioned probe and a colony showing a strong signal was detected by using DIG Nucleic Acid Detection Kit (Roche Diagnostics). The above-mentioned operations were carried out according to the protocol attached to the used reagent. The thus obtained clone was named pSAD and defined as a clone containing an AMP deaminase gene derived from *Streptomyces murinus* IFO 14802.

7. Analysis of Nucleotide Sequence of AMP Deaminase Gene

Firstly, the analysis of nucleotide sequence was started from the outside of the insert by using M13 Primer M4 and M13 Primer RV (Takara Shuzo Co., Ltd). DNA fragments used for the isolated clone and the probe were subjected to the analysis of nucleotide sequence again by designing a synthetic primer (SIGMA Genosys) based on the sequence of the enzyme gene that had been clarified from the results of the analysis. By primer walking in which these operations were repeated, a full-length DNA sequence was analyzed. The analysis of nucleotide sequence was carried out by using BigDye™ Terminator v3.1 Cycle Sequencing Kit and dGTP BigDye™ Terminator v3.0 Cycle Sequencing Ready Reaction Kit (Applied Biosystems Japan). For analysis, ABI PRISM™ 310 Genetic Analyzer (Applied Biosystems Japan) was used. Synthetic primers used for the sequence analysis were shown below.

```
MAD-F1:  5'-AAGCAACTCGCCGACCAG-3'   (SEQ ID NO: 8)

MAD-F2:  5'-TGGTCCATGCAGGACTTC-3'   (SEQ ID NO: 9)

MAD-F3:  5'-CTGGAGAACTACAGCCTC-3'   (SEQ ID NO: 10)

MAD-F4:  5'-CAGATCCTCGGCGTCAAG-3'   (SEQ ID NO: 11)

MAD-F5:  5'-CTCCAGTACGCCTTCCTG-3'   (SEQ ID NO: 12)

MAD-F6:  5'-GTCGGGTCCTGGACACCG-3'   (SEQ ID NO: 13)

MAD-F7:  5'-TATACCGTCCGGTAGGTC-3'   (SEQ ID NO: 14)

MAD-F8:  5'-GGACAGGAAGACGGACAC-3'   (SEQ ID NO: 15)

MAD-F9:  5'-GATTGGCCGAGAAGTACG-3'   (SEQ ID NO: 16)

MAD-R1:  5'-TGGTCGGCGAGTTGCTTG-3'   (SEQ ID NO: 17)

MAD-R2:  5'-CAGGGACAGGACACTGAG-3'   (SEQ ID NO: 18)

MAD-R3:  5'-GATGTCGACATGGCCCTG-3'   (SEQ ID NO: 19)

MAD-R4:  5'-CCCAGTCGATCGCGTGAG-3'   (SEQ ID NO: 20)

MAD-R5:  5'-TGGTCGTTCCGTGAAGGC-3'   (SEQ ID NO: 21)

MAD-R6:  5'-CTCGAACGCCGCGAACGC-3'   (SEQ ID NO: 22)

MAD-R7:  5'-CTGGGTGTGCGCGATGTC-3'   (SEQ ID NO: 23)

MAD-R8:  5'-CACCATCATCGCCACCTG-3'   (SEQ ID NO: 24)
```

All nucleotide sequences identified as a result of the analysis were shown in FIGS. 21 to 22 and FIGS. 25 to 26. Furthermore, by annotation using homology search and motif search, a promoter region, a coding region (SEQ ID NO: 4), and a terminator region were clarified (FIGS. 21 to 22). The sequence of the promoter region is shown in FIG. 27, the sequence of the coding region is shown in FIG. 28, and the sequence of the terminator region is shown in FIG. 29, respectively. Furthermore, a deduced amino acid sequence is shown in FIG. 23 (which does not contain signal peptide, SEQ ID NO: 1) and FIG. 24 (which contains signal peptide, SEQ ID NO: 2).

8. Obtaining of Vector pIJ702 for *Streptomyces*

*Streptomyces lividans* 3131 (ATCC 35287) carrying plasmid pIJ702 was cultured at 30° C. for two days under the following medium conditions.

YEME Medium+0.5% Glycine+50 µg/ml Thiostrepton (Wako Pure Chemical Industries)

| | |
|---|---|
| yeast extract | 3 g |
| peptone | 5 g |
| malt extract | 3 g |
| magnesium chloride | 1 g |
| glucose | 10 g |
| saccharose | 340 g |
| glycine | 5 g |
| 50 mg/ml thiostrepton solution (dimethylsulfoxide solution) | 1 ml/L (pH 7.0) |

Cultured medium (200 ml) was centrifuged (at 12,000 g at 4° C. for 10 minutes). The obtained fungus body was suspended in 10 ml of TE-Sucrose (50 mM Tris-HCl (pH 8.0), 10 mM EDTA and 25% Sucrose). Next, 2 ml of TE-Sucrose containing 30 mg/ml of lysozyme (Sigma Aldrich Japan K.K.) and 4 ml of 0.25 mM EDTA solution were added and incubated at 37° C. for 30 minutes. After incubation, 2 ml of 20% SDS solution was added, further 5 ml of 5M NaCl solution was added, gently stirred, and then incubated at 0° C. overnight. Next, to the supernatant obtained by centrifugation (at 100,000 g at 4° C. for 40 minutes), 30% polyethylenegly-col 6000 (Wako Pure Chemical Industries) solution was added so that the final concentration became 10%. Then the solution was incubated 0° C. for 4.5 hours. Thereafter, the solution was centrifuged (at 900 g at 4° C. for 5 minutes) and the obtained precipitations were dissolved in a TE solution containing 50 mM NaCl. Then, 16.8 g of cesium chloride and 1.2 ml of solution prepared by dissolving ethidium bromide in a TE solution so that the concentration became 10 mg/ml were added. The mixed solution was centrifuged (at 1,300 g at room temperature for 15 minutes) so as to remove residues. Thereafter, centrifugation (at 230,000 g at 20° C. for 12 hours) was carried out again. After centrifugation, a plasmid DNA layer was obtained under ultraviolet irradiation. Next, extraction was carried out by using a TE solution saturated with butanol so as to remove ethidium bromide. This extraction was repeated three times. The obtained plasmid DNA solution was subjected to dialysis by using TE as an external solution of dialysis at 4° C. overnight. Thereafter, extraction treatment with a TE solution saturated phenol was carried out once and extraction treatment with chloroform isoamyl alcohol was carried out twice. Next, 1/10 volume of 3M sodium acetate (pH 5.2) solution and two volume of ethanol were added and allowed to stand at −80° C. for 30 minutes. Thereafter, precipitations were collected by centrifugation (at 12,000 g at 4° C. for 15 minutes), washed with 70% ethanol and dried. This was dissolved in 200 µl of TE solution. The final amount of DNA that had been obtained by the above-mentioned operation was about 10 µg.

9. Construction of Shuttle Vector pSV1

Figure 15:
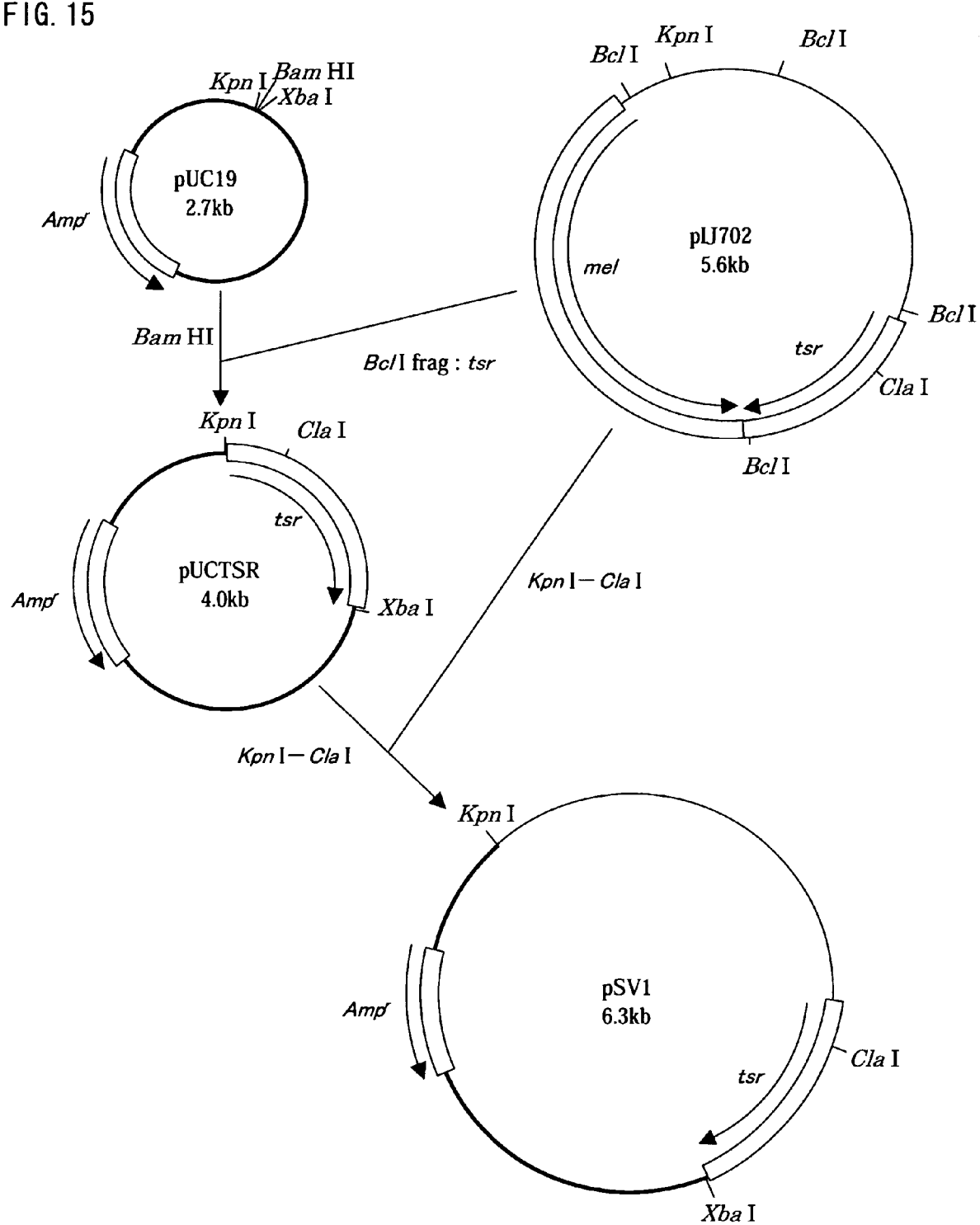
FIG. 15 shows a construction procedure of shuttle vector pSV1.

Firstly, a DNA fragment obtained by digesting *Escherichia coli* vector pUC19 (Takara Shuzo Co., Ltd) with restriction enzyme Bam HI and a DNA fragment containing a thiostrepton resistant gene (tsr) obtained by digesting *Streptomyces* vector pIJ702 with Bcl I (Takara Shuzo Co., Ltd) were prepared. These were ligated to each other by using DNA Ligation Kit Ver.2 (Takara Shuzo Co., Ltd) so as to produce pUCTSR. Next, a DNA fragment (long fragment) obtained by digesting pUCTSR with Kpn I and Cla I (Takara Shuzo Co., Ltd) and a DNA fragment (short fragment) obtained by digesting pIJ702 with Kpn I and Cla I (Takara Shuzo Co., Ltd) were prepared and they were ligated to each other by using DNA Ligation Kit Ver.2 (Takara Shuzo Co., Ltd), followed by transformation to *Escherichia coli* DH 5 strain (TOYOBO Co., Ltd.). A plasmid, in which pUC19 fragment and a pIJ 702 fragment carried by the thus obtained transformant were ligated to each other, was made to be a shuttle vector pSV1, which was used for the later operation (FIG. 15).

10. Construction of Expression Vector pSVSAD

Figure 16:
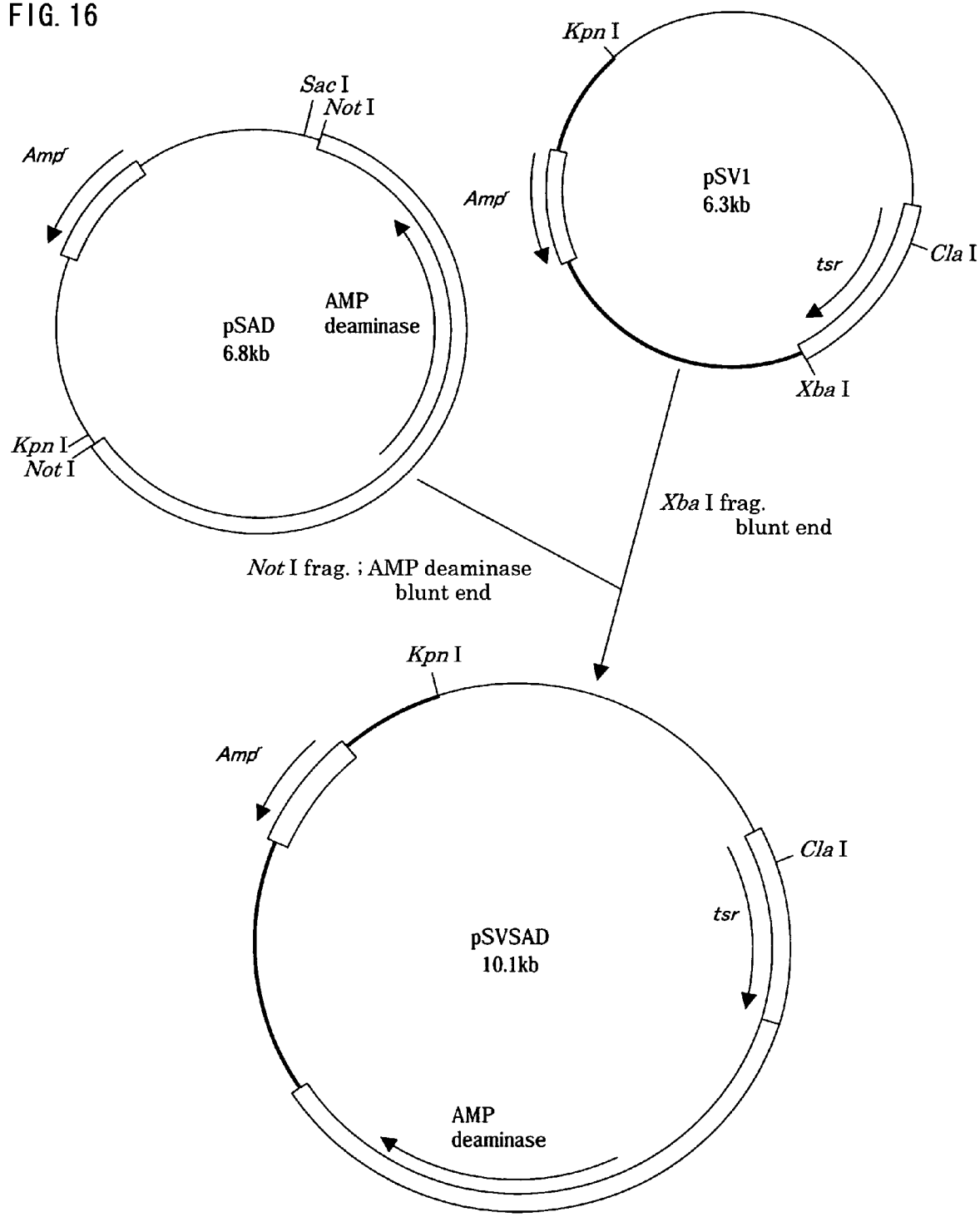
FIG. 16 shows a construction procedure of AMP deaminase expression vector pSVSAD.

The gene fragment was prepared by digesting pSAD carrying an AMP deaminase gene with restriction enzyme Not I (Takara Shuzo Co., Ltd). Furthermore, a vector fragment was prepared by digesting shuttle vector pSV1 with restriction enzyme Xba I. Both fragments were blunted at their ends by using DNA Blunting Kit (Takara Shuzo Co., Ltd) and made to be an insert fragment and a vector fragment, respectively. A vector fragment derived from pSV1 was further subjected to dephosphorylation treatment by using Alkaline Phosphatase (Takara Shuzo Co., Ltd). The insert and vector were ligated to each other by using DNA Ligation Kit Ver.2 (Takara Shuzo Co., Ltd), and thereafter transformed to *Escherichia coli* DH5 strain (TOYOBO Co., Ltd.). The thus obtained plasmid was made to be an expression vector pSVSAD for use in transformation (FIG. 16).

11. Preparation of *Streptomyces lividans* TK24 Protoplast

*Streptomyces lividans* TK24 is a strain having resistance against streptomycin derived from *Streptomyces lividans* 66 and it was provided by D. A. Hopwood (John Innes Institute, Colney Lane, Norwich NR47UH, U. K.). *Streptomyces lividans* TK24 was cultured using a YEME medium (0.5% glycine) at 30° C. for two days. The 200 ml of cultured medium was centrifuged (at 1,300 g at room temperature for 10 minutes). The obtained fungus body was suspended in 72 ml of 0.35 M saccharose solution. Then, this suspension was centrifuged (at 1,300 g at room temperature for 10 minutes) and the fungus body was suspended again in 60 ml of P buffer solution containing 1 mg/ml of lysozyme (Sigma Aldrich Japan K.K.). The suspension was incubated at 30° C. for 2.5 hours. The suspension after incubation was filtrated with absorbent cotton so as to remove residues. Then, the resultant filtrate was centrifuged (at 1,300 g at room temperature for 10 minutes) and the sediment was washed with 25 ml of P buffer solution. This washing was repeated twice and precipitation was suspended in 1 ml of P buffer solution to obtain a protoplast suspension.

| P buffer solution | |
|---|---|
| TES [N-Tris(hydroxymethyl)methyl-2-aminoethane sulphonic acid] | 5.73 g |
| Saccharose | 103 g |
| Magnesium chloride | 2.03 g |
| Potassium sulfate | 0.5 g |
| Calcium chloride | 3.68 g |
| Trace element solution | 2 ml/L |
| | (pH 7.4) |

Note here that 1% monobasic potassium phosphate solution was prepared separately, which was added in the amount of 1 ml per 100 ml P buffer solution immediate before use.

| Trace element solution | |
|---|---|
| Zinc chloride | 40 mg |
| Ferric chloride | 200 mg |
| Cupric chloride | 10 mg |
| Manganese chloride | 10 mg |
| Sodium tetraborate | 10 mg |
| Ammonium molybdate | 10 mg/L |

12. Transformation of *Streptomyces lividans* TK24

Each of the following solutions was mixed so that the total amount became 121 µl.

| | |
|---|---|
| TE solution containing AMP deaminase expression plasmid pSVSAD (4 µg) | 1 µl |
| *Streptomyces lividans* TK24 protoplast | 100 µl |
| 0.35 M saccharose solution | 20 µl |

Then, 1.5 ml of P buffer solution containing 20% polyethylene glycol 1000 was added and gently mixed by pipetting. The mixture was allowed to stand for two minutes at room temperature. The mixture was centrifuged (at 1,700 g at room temperature for 10 minutes) to collect precipitate. Protoplast obtained as precipitate was washed twice with P buffer solution. The pellet was resuspended in 0.3 ml of buffer solution P, and then 100 µl each of the suspension was dropped on an R-2 medium. Then, the R-2 top agarose medium that had been kept warm at 55° C. was poured into the plate in the amount of 3 ml/plate so that protoplast was dispersed over the entire plate. The plate was dried in a clean bench for two hours until the top agarose was solidified. After drying, the plate was cultured at 30° C. for 16 hours. Then, 3 ml of R-2 top agarose medium containing 200 µg/ml thiostrepton was added to the plate so as to cover the surface of the plate, followed by drying for two hours. The plate was cultured for further four days at 30° C. so as obtain a transformant (SAD-1) having a thiostrepton resistant property.

The R-2 medium was produced by preparing the following R-2/A and R-2/B separately and combining them. A medium containing agar was R-2 plate and a medium containing agarose was R-2 top agarose medium. When a plate medium was produced, R-2/A and R-2/B were mixed and furthermore, 1% $KH_2PO_4$ was mixed at the ratio of 1 ml per 200 ml of the final volume.

| R-2/A | |
|---|---|
| Potassium Sulfate | 0.5 g |
| Magnesium Chloride | 20.2 g |
| Calcium Chloride | 5.9 g |
| Glucose | 20.0 g |
| Proline | 6.0 g |
| Casamino Acid | 0.2 g |
| Trace Element Solution | 4.0 ml |
| Agar | 44.0 g/L or agarose 5.0 g/L |

| R-2/B | |
|---|---|
| TES | 11.5 g |
| Yeast Extracts | 10.0 g |
| Saccharose | 203 g/L (pH 7.4) |

13. Culture of Transformant

In accordance with the procedure of the above-mentioned Example (<Preparation method of enzyme solution>), Solpee N.Y. (2%), Meast P1G (0.5%), KH$_2$PO$_4$ (0.1%), MgSO$_4$ (0.05%) and soluble starch (3%) were added so as to adjust to pH 5.7 and sterilized at 121° C. for 30 minutes. Transformant SAD-1 and a host strain *Streptomyces lividans* TK24 of transformation was inoculated, pre-cultured for two days and cultured for five days at 30° C. A part of the culture supernatant was collected and used as a sample for measuring the AMP deaminase activity.

14. Measurement of AMP Deaminase Activity

The enzyme activity of the sample obtained above was measured in accordance with the method show in Example (<Method of measuring enzyme activity>). To 1.5 ml of solution obtained by mixing 0.017M 5'AMP-2Na and 1/15M phosphate buffer solution (pH 5.6) at the ratio of 1:2, 0.5 ml of sample solution was added so as to obtain a reaction solution, which was reacted at 37° C. for 15 minutes. After 15 minutes, 2% perchloric acid solution was added so as to stop the reaction and 100 μl of the solution was taken out. Water was added to the solution so that the total amount was 5 ml. Then, OD$_{265}$ was measured. The value similarly measured at reaction time of 0 minute was defined as a blank. Under the below-mentioned conditions, a case where an absorbance difference is reduced by 0.001 during 60 minutes was defined as one unit. The measurement result is shown in FIG. 17. Note here that a culture supernatant obtained after *Streptomyces lividans* TK24 had been cultured under the same conditions was made to be a control.

As show in FIG. 17, a culture supernatant of transformant SAD-1 exhibited a high AMP deaminase activity. The results confirmed that an AMP deaminase gene was successfully obtained. In addition, it was shown that an AMP deaminase production system was actually constructed by using the gene.

15. Thermostability of AMP Deaminase Derived from Transformant (SAD-1)

The thermostability of AMP deaminase produced by transformant (SAD-1) was measured. Culture supernatant of SAD-1 prepared by the above-mentioned method was treated at a predetermined temperature, and the residual AMP deaminase activity was measured (pH 5.6). Note here that treatment temperature was 30° C., 40° C., 50° C., 60° C., 65° C., 70° C., and 75° C. Furthermore, the treatment time was 30 minutes.

Figure 18:
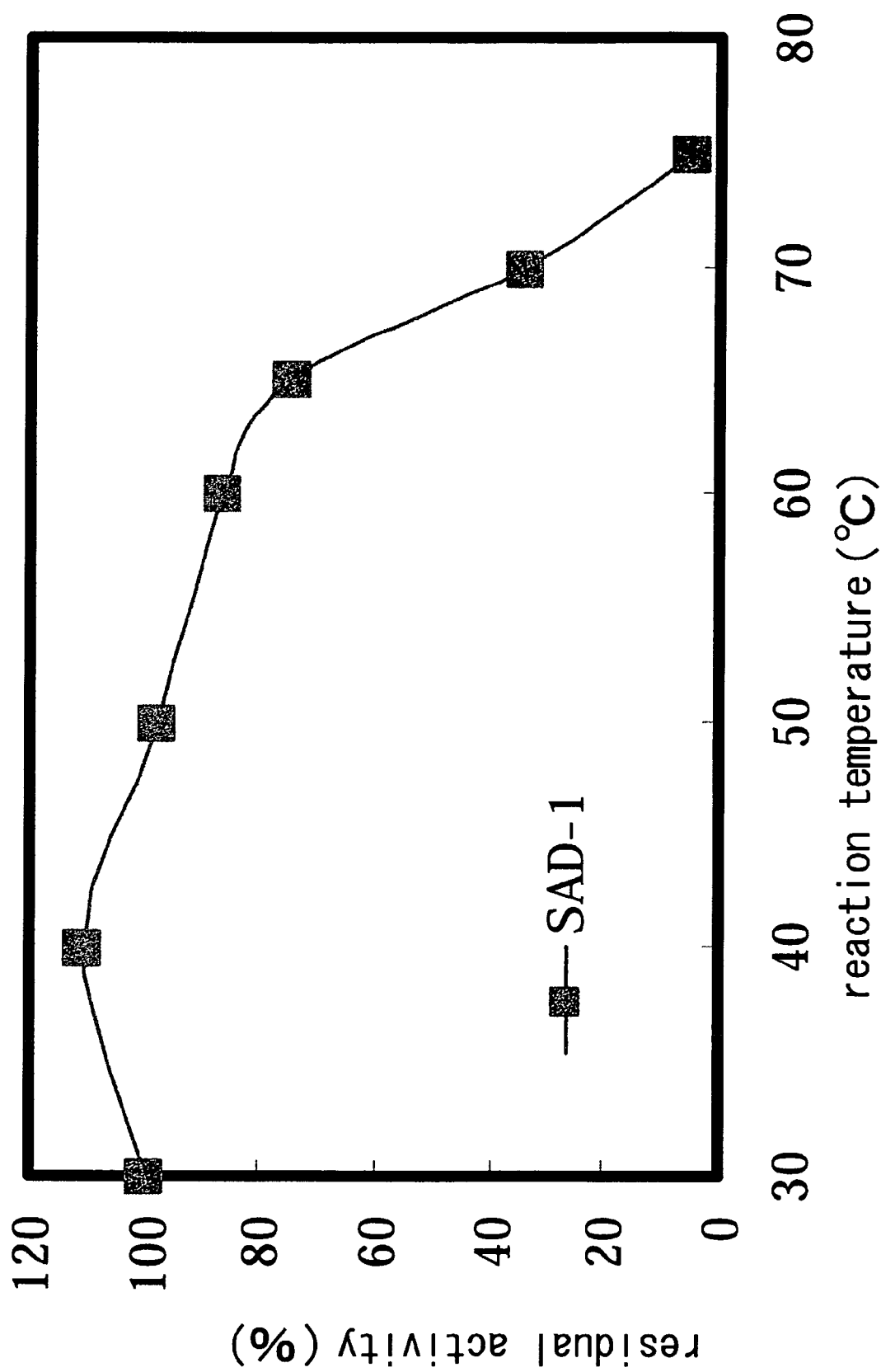
FIG. 18 is a graph showing thermostability of AMP deaminase produced by transformant (SAD-1). The abscissa represents a reaction temperature and the ordinate represents residual deaminase activity (%).

The measurement result is shown a graph of FIG. 18. It is found that the thermostability similar to that of AMP deaminase derived from *Streptomyces murinus* shown in FIG. 1 was exhibited.

16. Substrate Specificity of AMP Deaminase Derived from Transformant (SAD-1)

In order to determine whether the deaminase derived from transformant (SAD-1) obtained as mentioned above was AMP deaminase or Adenosine-deaminase, the substrate specificity was investigated. The results are shown in FIG. 19. Note here that relative activities when the enzyme activity with respect to 5' AMP was defined as 100% are represented. The enzyme acted on 5' AMP most favorably. Furthermore, the enzyme also acted on 3'-AMP, 5'-dAMP, ADP, ATP, Adenosine and 3'5'-cyclic AMP, but did not act on 2'-AMP and adenine at all. In particular, the enzyme acted on 5'-dAMP, ADP and ATP favorably. From the above-mentioned results, it was confirmed that deaminase derived from transformant (SAD-1) was similar to AMP deaminase derived from *Streptomyces murinus* and it was AMP deaminase. Furthermore, it was determined that the enzyme can be preferably used with respect to the reaction using 5'-dAMP, ADP and ATP as a substrate.

17. Confirmation of Production of AMP Deaminase Derived from Transformant (SAD-1)

Figure 20:
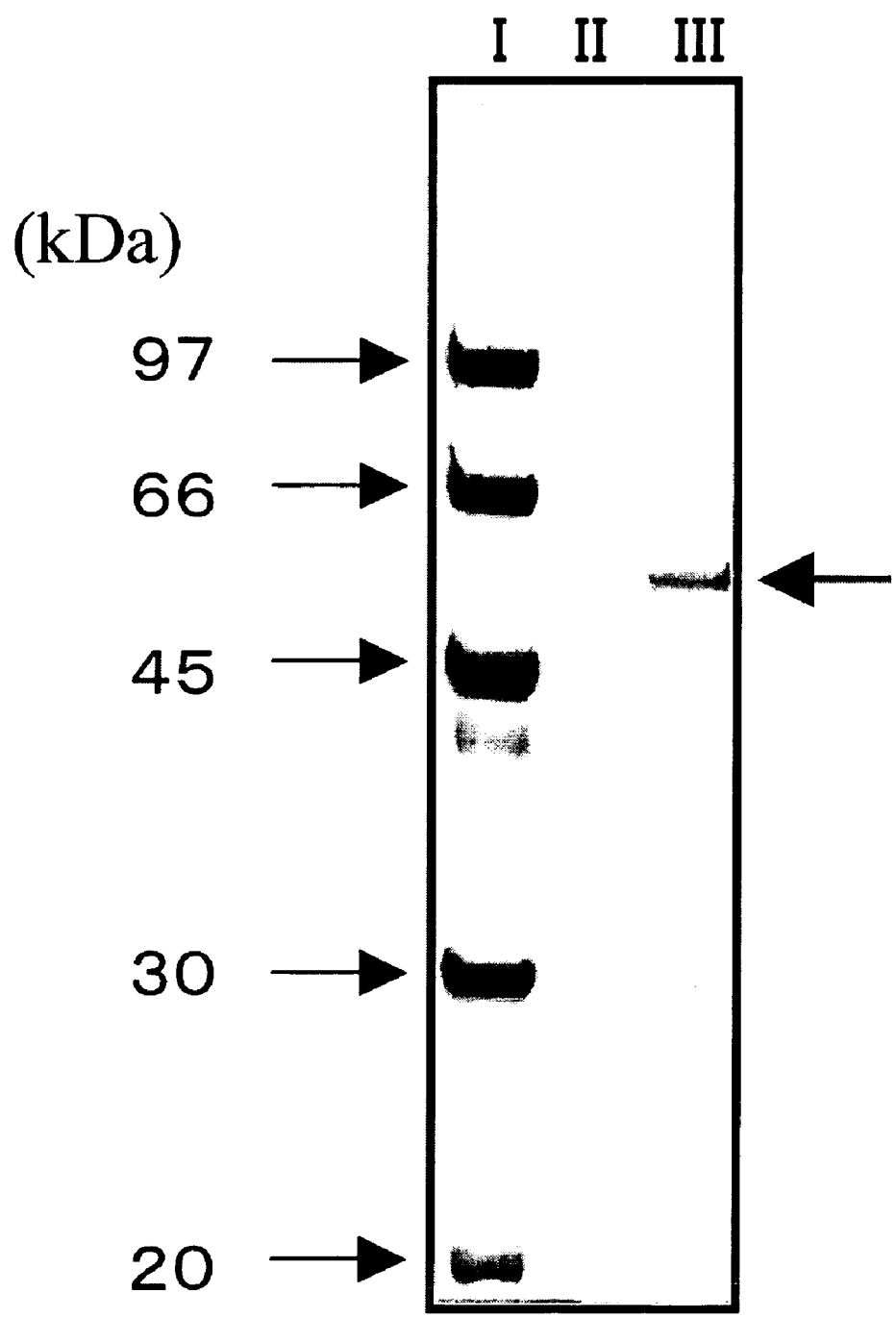
FIG. 20 shows results of analysis of AMP deaminase derived from transformant (SAD-1) by SDS-PAGE (CBB staining). Lane II is a control sample lane (culture supernatant of host), and lane III is a sample lane (culture supernatant of transformant). Lane I shows bands of protein molecular weight marker. Phosphorylase b (M.W. 97,000), bovine serum albumin (M.W. 66,000), ovalbumin (M.W. 45,000), carbonic anhydrase (M.W. 30,000), trypsin inhibitor (M.W. 20,100) bands are shown from the side of the high molecular weight.

The culture supernatant of SAD-1 was subjected to SDS-PAGE (CBB staining) so as to confirm that the enzyme was produced by a transformant. The result of SDS-PAGE is shown in FIG. 20. Lane II shows a control (culture supernatant of host bacteria). Lane III shows a culture supernatant of transformant (SAD-1). In lane III, band that is not observed in lane II is present, showing that new enzyme protein is produced by transformation. In lane I, a band of the protein molecular weight marker is shown. Phosphorylase b (M.W. 97,000), bovine serum albumin (M.W. 66,000), ovalbumin (M.W. 45,000), carbonic anhydrase (M.W. 30,000), trypsin inhibitor (M.W. 20,100) bands are shown from the side of the high molecular weight.

As mentioned above, the present inventors have succeeded in cloning a gene encoding AMP deaminase derived from *Streptomyces murinus*. Furthermore, they have succeeded in obtaining a transformant in which the gene was introduced by using a transformation system of *Streptomyces* and confirmed the expression of the gene. These results enabled the enzyme to be produced as a recombinant. Therefore, the stable supply of the enzymes can be realized. Furthermore, improvement of the productivity of the enzyme by gene recombination and improvement of the enzyme itself can be realized. For example, the following (1) to (3) can be provided: (1) improvement of productivity by the use of a promoter exhibiting a high productivity; (2) production of a highly productive transformant by the use of a highly productive strain as a host and construct of a highly productive system using the same; and (3) improvement of productivity, improvement of stability and/or improvement of substrate specificity by modifying a nucleotide sequence and amino acid sequence.

INDUSTRIAL APPLICABILITY

AMP deaminase of the present invention has excellent thermostability. Therefore, the AMP deaminase is suitably used for applications in which a reaction at high temperature is desired. For example, AMP deaminase of the present invention can be used as an enzyme for enhancing the taste in the production of yeast extract or an enzyme for producing a seasoning agent, 5'-inosinic acid.

On the other hand, by using characteristics that AMP deaminase acts on a substrate other than AMP, AMP deaminase of the present invention can be used in various reactions using a substrate such as ADP, ATP, 5'dAMP as a starting material.

The present invention is not limited to the description of the above embodiments and Examples. A variety of modifications, which are within the scopes of the following claims and which are achieved easily by a person skilled in the art, are included in the present invention.

All of the articles, publication of unexamined patent application, and Patent Gazette cited herein are hereby incorporated by reference.

The invention claimed is:

1. An isolated AMP deaminase having the amino acid sequence of SEQ ID NO: 1 comprising the following characteristics:
   (1) action
   catalyzing a reaction of acting on 5'-nucleotide including adenosine as a component so as to deaminate the 5'-nucleotide;
   (2) substrate specificity
   acting on 5'-AMP, 5'-dAMP, ADP, ATP, and 3', 5'-cyclic AMP, which are 5'-nucleotides including adenosine as a component, and acting on 5'-AMP most favorably;
   (3) optimum temperature
   having an optimum temperature of around 65° C.;
   (4) temperature stability being stable at a temperature of 65° C. or less;
   (5) optimum pH
   having an optimum pH of around 5.6;
   (6) pH stability
   being stable at pH 6.0 to pH 8.5; and
   (7) molecular weight
   having a molecular weight of 48,000±2,000 in gel filtration and 60,000±3,000 in SDS-PAGE.

2. The isolated AMP according to claim 1, wherein said 5'-nucleotide including adenosine as a component is 5'-adenylic acid.

3. The isolated AMP deaminase according to claim 1, wherein the AMP deaminase is purified from Streptomyces.

4. The isolated AMP deaminase according to claim 3, wherein the Streptomyces belongs to the genus Streptomyces.

5. The isolated AMP deaminase according to claim 3, wherein the *Streptomyces* is *Streptomyces murinus*.

6. An isolated AMP deaminase consisting of the following (a) or (b):
 (a) a protein having the amino acid sequence of SEQ ID NO:1;
 (b) a protein having an amino acid sequence obtained by deleting, substituting, inserting or adding one to 25 amino acids in the amino acid sequence of SEQ ID NO:1, and functioning as AMP deaminase.

* * * * *